US007928213B2

(12) United States Patent
Prussak et al.

(10) Patent No.: US 7,928,213 B2
(45) Date of Patent: Apr. 19, 2011

(54) NUCLEIC ACIDS ENCODING CHIMERIC CD154 POLYPEPTIDES

(75) Inventors: Charles E. Prussak, San Diego, CA (US); Thomas J. Kipps, Rancho Santa Fe, CA (US); Mark J. Cantwell, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 258 days.

(21) Appl. No.: 12/389,904

(22) Filed: Feb. 20, 2009

(65) Prior Publication Data

US 2010/0297695 A1 Nov. 25, 2010

Related U.S. Application Data

(62) Division of application No. 10/154,759, filed on May 23, 2002, now Pat. No. 7,495,090.

(51) Int. Cl.

| | |
|---|---|
| *C12N 15/62* | (2006.01) |
| *C12N 15/12* | (2006.01) |
| *C12N 15/00* | (2006.01) |
| *C12N 15/63* | (2006.01) |

(52) U.S. Cl. .................... 536/23.4; 536/23.1; 536/23.5; 435/252.3; 435/320.1; 435/455

(58) Field of Classification Search ........................ None
See application file for complete search history.

(56) References Cited

U.S. PATENT DOCUMENTS

| | | | |
|---|---|---|---|
| 5,716,805 | A | 2/1998 | Srinivasan et al. |
| 5,817,516 | A | 10/1998 | Kehry et al. |
| 5,861,310 | A | 1/1999 | Freeman et al. |
| 5,962,406 | A | 10/1999 | Armitage et al. |
| 6,451,759 | B1 | 9/2002 | Kang et al. |
| 6,544,523 | B1 | 4/2003 | Chu |
| 7,070,771 | B1 | 7/2006 | Kipps et al. |
| 7,495,090 | B2 | 2/2009 | Prussak et al. |
| 2002/0022017 | A1 | 2/2002 | Yu |
| 2004/0209295 | A1 | 10/2004 | Schwabe et al. |
| 2005/0158831 | A1 | 7/2005 | Kornbluth |

FOREIGN PATENT DOCUMENTS

| | | | |
|---|---|---|---|
| EP | 0 317 641 | A1 | 5/1989 |
| EP | 0 675 200 | A1 | 10/1995 |
| EP | 1 016 721 | A1 | 7/2000 |
| WO | WO 91/02540 | A1 | 3/1991 |
| WO | WO 93/08207 | A1 | 4/1993 |
| WO | WO 94/04680 | A1 | 3/1994 |
| WO | WO 94/17196 | A1 | 8/1994 |
| WO | WO 95/14487 | A1 | 6/1995 |
| WO | WO 95/18819 | A1 | 7/1995 |
| WO | WO 95/32627 | A1 | 12/1995 |
| WO | WO 96/14876 | A1 | 5/1996 |
| WO | WO 96/18413 | A1 | 6/1996 |
| WO | WO 96/22370 | A1 | 7/1996 |
| WO | WO 98/21232 | A2 | 5/1998 |
| WO | WO 98/21232 | A3 | 5/1998 |
| WO | WO 98/26061 | A2 | 6/1998 |
| WO | WO 98/26061 | A3 | 6/1998 |

OTHER PUBLICATIONS

Addison, Christina L. et al., "Intratumoral injection of an adenovirus expressing interleukin 2 induces regression and immunity in a murine breast cancer model", *Proc. Natl. Acad. Sci. U.S.A.*, 92:8522-8526 (1995).

Alderson et al., "CD40 expression by human monocytes: Regulation by cytokines and activation of monocytes by the ligand for CD40", J. *Exp. Med.*, 178:669-674 (1993).

Ali, Munaf et al., "The use of DNA viruses as vectors for gene therapy", *Gene Therapy*, 1:367-384 (1994).

Ali, Stuart Alvaro et al., "PCR-Ligation-PCR Mutagenesis: A Protocol for Creating Gene Fusions and Mutations", *Bio Techniques*, 18:746-750 (1995).

Armitage et al., "CD40 ligand is a T cell growth factor", *Eur. J. Immunol.*, 23:2326-2331 (1993).

Armitage, Richard J. et al., "Molecular and biological characterization of a murine ligand for CD40", *Nature*, 357:80-82 (1992).

Aruffo et al., "The CD40 ligand, gp39, is defective in activated T cells from patients with X-linked hyper-Igfvl syndrome", *Cell*, 72:291-300 (1993).

Attwood, T.K., "The Babel of Bioinformatics", *Science*, 290:471-473 (2000).

Banchereau et al., "The CD40 antigen and its ligand", *Annual Review Immunol.*, 12:881-922 (1994).

Banchereau, Jacques et al., "Long-Term Human B Cell Lines Dependent on Interleukin-4 and Antibody to CD40", *Science*, 251:70-72 (1991).

Berman, Joan W. et al., "Gene transfer in lymphoid cells: Expression of the Thy-1,2 antigen by Thy-1.1 BW5147 lymphoma cells transfected with unfractionated cellular DNA", *Proc. Natl. Acad. Sci. USA*, 81:7176-7179 (1984).

Black et al., "A metalloproteinase disintegrin that releases tumour-necrosis factor-alpha from cells", *Nature*, 385(6618):729-33 (1997).

(Continued)

*Primary Examiner* — Phillip Gambel
(74) *Attorney, Agent, or Firm* — DLA Piper LLP (US)

(57) ABSTRACT

The present invention provides for an isolated polynucleotide sequence encoding a chimeric CD154, comprising a first nucleotide sequence encoding an extracellular subdomain of non-human CD154, preferably murine CD154, that replaces a cleavage site of human CD154, and a second nucleotide sequence encoding an extracellular subdomain of human CD154 that binds to a human CD154 receptor. The present invention also provides for the chimeric CD154 that is encoded by the above-described polynucleotide sequence, an expression vector and a genetic vector comprising the polynucleotide sequence, a host cell comprising the expression vector or the genetic vector, a process for producing the chimeric CD154, and methods for utilizing the expression vectors and genetic constructs containing the chimeric CD154 polynucleotide sequences.

17 Claims, 46 Drawing Sheets

OTHER PUBLICATIONS

Figure 1:
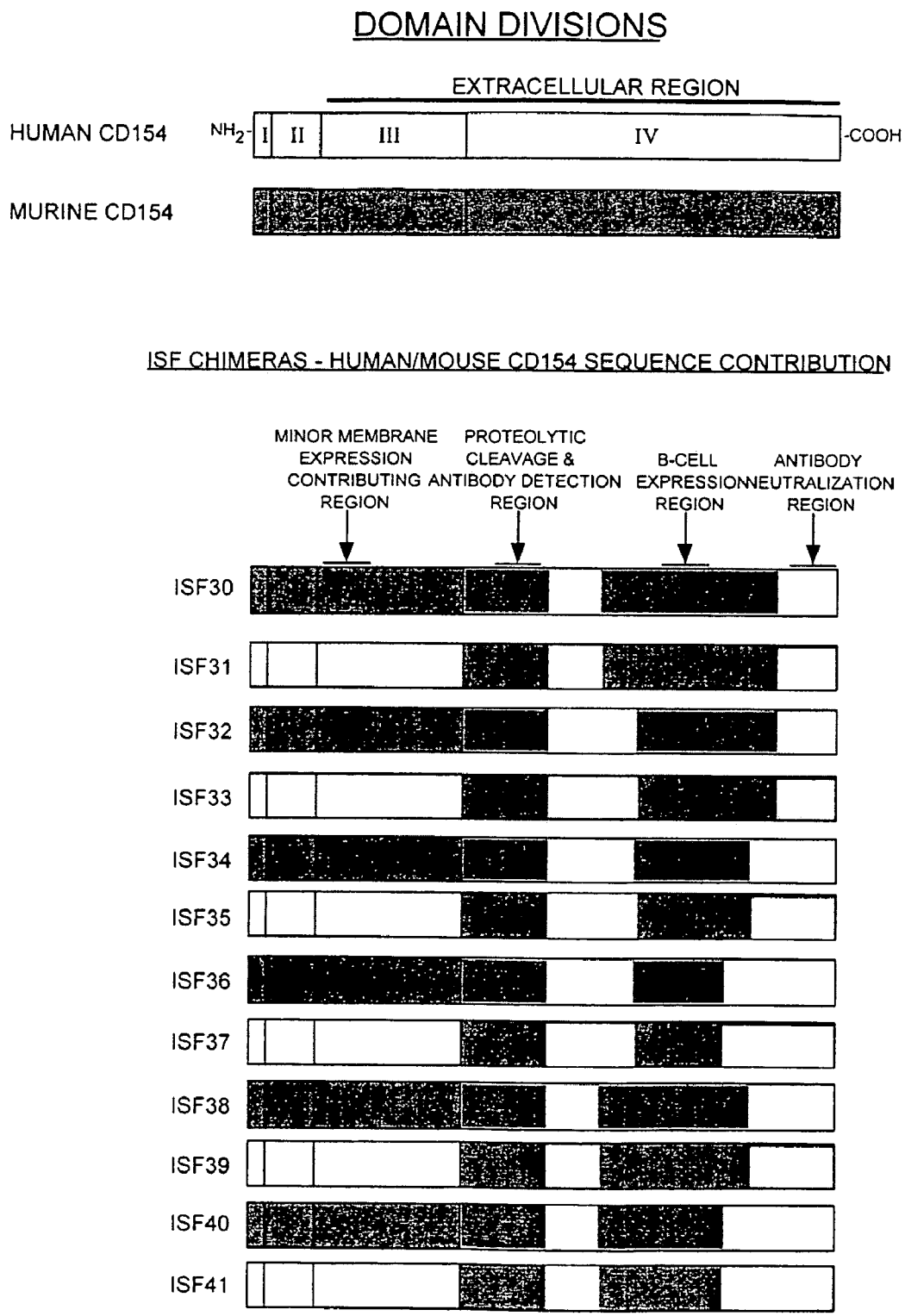

Blieden, Timothy M. et al., "Class-I MHC Expression in the Mouse Lung Carcinoma, Line 1: A Model for Class-I Inducible Tumors", *Int. J. Cancer Supp.*, 6:82-89 (1991).

Boles, Eckhard et al., "A rapid and highly efficient method for PCR-based site-directed mutagenesis using only one new primer", *Curr. Genet.*, 28:197-198 (1995).

Boris-Lawrie, Kathleen A. et al., "Recent advances in retrovirus vector technology", *Current Opinion in Genetics and Development*, 3:102-109 (1993).

Brody, Steven L. et al., "Adenovirus-mediated in Vivo Gene Transfer", *Ann. N. Y. Acad. Sci.*, 716:90-103 (1994).

Cadwell, R. Craig et al., "Randomization of Genes by PCR Mutagenesis", *PCR Methods and Applications*, 2:28-33 (1992).

Cantwell et al., "Acquired CD40-ligand deficiency in chronic lymphocytic leukemia", *Nat. Med.*, 3:984-989 (1997).

Cantwell et al., "Membrane-Stabilizing Chimeric Tumor Necrosis Factor for Gene Therapy of B Cell Malignancies", *Blood*, 98(11 Part 1):423a (2001).

Cantwell, M.J. et al., "CD95 and FAS-ligand expression and apoptosis in rheumatoid arthritis", *Arthritis and Rheumatism*, 39(9), Suppl.:287 (1996).

Cantwell, Mark J. et al., "Adenovirus Vector Infection of Chronic Lymphocytic Leukemia B Cells", *Blood*, 88:4676-4683 (1996).

Carter, Barrie J., "Adeno-associated virus vectors", *Current Opinion in Biotechnology*, 3:533-539 (1992).

Castle et al., "Regulation of expression of the ligand for CD40 on T helper lymphocytes", *J. Immunol.*, 151:1777-1788 (1993).

Clark, Edward A. et al., "Activation of human B cells mediated through two distinct cell surface differentiation antigens, Bp35 and Bp50", *Proc. Natl. Acad. Sci. U.S.A.*, 83:4494-4498 (1986).

Cooper, Mark J., "Noninfectious Gene Transfer and Expression Systems for Cancer Gene Therapy", *Seminars in Oncology*, 23:172-187 (1996).

Cosman, David et al., "Cloning, sequence and expression of human interleukin-2 receptor", *Nature*, 312:768-771 (1984).

Danko, Istvan et al., "Direct gene transfer into muscle", *Vaccine*, 12:1499.1502 (1994).

Davis, Heather L. et al., "Direct Gene Transfer into Skeletal Muscle in Vivo: Factors Affecting Efficiency of Transfer and Stability of Expression", *Human Gene Therapy*, 4:151-159 (1993).

Deans, Robert J. et al., "Expression of an immunoglobulin heavy chain gene transfected into lymphocytes", *Proc. Natl. Acad. Sci. USA*, 81:1292-1296 (1984).

Decoster et al., "Generation and biological characterization of membrane-bound, uncleavable murine tumor necrosis factor", *J. Biol. Chem.*, 270(31):18473-8 (1995).

DeMatteo, Ronald P. et al., "Gene Transfer to the Thymus", *Annals of Surgery*, 222:229-242 (1995).

Dilloo et al., "CD40 ligand induces an antileukemia immune response in vivo", *Blood*, 90:1927-1933 (1997).

Evans, Christopher et al., "Clinical Trial to Assess the Safety, Feasibility, and Efficacy of Transferring a Potentially Anti-Arthritic Cytokine Gene to Human Joints with Rheumatoid Arthritis", *Human Gene Therapy*, 7:1261-1280 (1996).

Fanslow, William C. et al., "Structural characteristics of CD40 ligand that determine biological function", *Seminars in Immunology*, 6:267-278 (1994).

Felgner, Philip L. et al., "Improved Cationic Lipid Formulations for in Vivo Gene Therapy", *Ann. N. Y. Acad. Sci.*, 772:126-139 (1995).

Fisher, Lisa J. et al., "In vivo and ex vivo gene transfer to the brain", *Current Opinion in Neurobiology*, 4:735-741 (1994).

Flotte, T. R. et al., "Adeno-associated virus vectors for gene therapy", *Gene Therapy*, 2:357-362 (1995).

Furth, Priscilla A. et al., "Gene Transfer into Mammalian Cells by Jet Injection", *Hybridoma*, 14:149-152 (1995).

Galle, Peter R. et al., "Involvement of the CD95 (APO-1/Fas) Receptor and Ligand in Liver Damage", *J. Exp. Med.*, 182:1223-1230 (1995).

Glorioso, J. C. et al., "Development and application of herpes simplex virus vectors for human gene therapy", *Annu. Rev. Microbiol.*, 49:675-710 (1995).

Goldspiel, Barry R. et al., "Human gene therapy", *Clinical Pharmacy*, 12:488-505 (1993).

Graham, Frank L. et al., "Manipulation of Adenovirus Vectors", *Methods in Molecular Biology*, 7(11):109-128 (1991).

Grewal et al., "CD40 and CD154 in cell-mediated immunity", *Annual Review of Immunology*, 16:111-135 (1998).

Hengge, Ulrich R. et al., "Expression of Naked DNA in Human, Pig, and Mouse Skin", *Journal of Clinical Investigation*, 97:2911-2916 (1996).

Henkel, Thomas et al., "Functional Analysis of Mutated cDNA Clones by Direct Use of PCR Products in in Vitro Transcription/Translation Reactions", Analytical Biochemistry, 214:351-352 (1993).

Hermann et al., "Expression of a 32-kDa ligand for the CD40 antigen on activated human T lymphocytes", *Eur. J. Immunol.*, 23:961-964 (1993).

Hirano et al., "Inhibition of human breast carcinoma growth by a soluble recombinant human CD40 ligand", *Blood*, 93: 2999-3007 (.1999).

Hollenbaugh, Diane et al., "The human T cell 'antigen gp39, a member of the TNF gene family, is a ligand for the CD40 receptor: expression of a soluble form of gp39 with B cell co-stimulatory activity", *The EMBO Journal*, 11:4313-4321 (1992).

Horton, Robert M., "PCR-mediated Recombination and Mutagenesis", *Molecular Biotechnology*, 3:93-99 (1995).

Jolly, Douglas, "Viral vector systems for gene therapy", *Cancer Gene Therapy*, 1:51-64 (1994).

Kass-Eisler, Alyson et al., "Prospects for Gene Therapy with Direct Injection of Polynucleotides", *Ann. N. Y. Acad. Sci.*, 772:232-240 (1995).

Kato et al., "Gene transfer of C40-ligand induces autologous immune recognition of chronic lymphocytic leukemia B cells", *J.Clin. Invest.*, 101:1133-1141 (1998).

Kato et al., "Adenovirus-mediated gene transfer of CD40-ligand induces autologous immune recognition of chronic lymphocytic leukemia B cells", *Blood*, 90: Abstract No. 1157 (1997).

Kikuchi et al., "Anti-tumor immunity induced by in vivo adenovirus vector-mediated expression of CD40 ligand in tumor cells", *Hum. Gene Then.*, 10:1375-1387 (1999).

Kipps, Thomas J. et al., "New developments in flow cytometric analyses of lymphocyte markers", *Laboratory Immunology II*, 12:237-275 (1992).

Koc, Omer N. et al., "Transfer of Drug Resistance Genes Into Hematopoietic Progenitors to Improve Chemotherapy Tolerance", *Seminars in Oncology*, 23:46-65 (1996).

Kohn, Donald B., "The current status of gene therapy using hematopoietic stem cell", *Current Opinion in Pediatrics*, 7:56-63 (1995).

Korthauer et al., "Defective expression of T-cell CD40 ligand causes X-linked immunodeficiency with hyper-IgM", *Nature*, 361:539-541 (1993).

Kouskoff, Valerie et al., "Organ-Specific Disease Provoked by Systemic Autoimmunity", *Cell*, 87:811-822 (1996).

Kunkel, Thomas A. et al., "Rapid and Efficient Site-Specific Mutagenesis without Phenotypic Selection", *Methods in Enzymology*, 154:367-382 (1987).

Kunkel, Thomas A., "Rapid and efficient site-specific mutagenesis without phenotypic selection", *Proc. Natl. Acad. Sci. USA*, 82:488-492 (1985).

Laman et al., "Functions of CD40 and its ligand, gp39 (CD4OL)", *Crit. Rev. Immunol.*, 16:59-108 (1996).

Lederman et al., "T-BAM/CD40-L on helper T lymphocytes augments lymphokine-induced B cell Ig isotype switch recombination and rescues B cells from programmed cell death", *Journal of Immunology*, 152:2163-2171, 1994.

Lu, Li et al., "Stem cells from bone marrow, umbilical cord blood and peripheral blood for clinical application: current status and future application", *Critical Reviews in Oncology/Hematology*, 22:61-78 (1996).

Mackey et al., "The role of CD40/CD154 interactions in the priming, differentiation, and effector function of helper and cytotoxic T cells", *Journal of Leukocyte Biology*, 63:418-428 (1998).

Majumder, Kumud et al., "Background-minimized Cassette Mutagenesis by PCR Using Cassette-specific Selection Markers: A Useful General Approach for Studying Structure-Function Relationships of Multisubstrate Enzymes", *PCR Methods and Applications*, 4:212-218 (1995).

Morris et al., "Incorporation of an isoleucine zipper motif enhances the biological activity of soluble CD4OL (CD154)", *The Journal of Biological Chemistry*, 274:418-423 (1999).

Morrison, Hilary G. et al., "A PCR-Based Strategy for Extensive Mutagenesis of a Target DNA Sequence", *BioTechniques*, 14:454-457 (1993).

Moss et al., "Cloning of a disintegrin metalloproteinase that processes precursor tumour-necrosis factor-alpha", *Nature*, 385(6618):733-6 (1997).

Mueller et al., "Noncleavable transmembrane mouse tumor necrosis factor-alpha (TNFalpha) mediates effects distinct from those of wild-type TNFalpha in vitro and in vivo", *J. Biol. Chem.*, 274(53):38112-8 (1999).

Nadler, Lee M., "The Malignant Lymphomas", *Harrison's Principles of Internal Medicine*, Wilson et al., eds., McGraw-Hill, New York, Chapter 302, pp. 1599-1612, (1991).

Nagase, H. et al., "Human Matrix Metalloproteinase Specificity Studies Using Collagen Sequence-Based Synthetic Peptides", *Biopolymers (Peptide Science)*, 40:399-416 (1996).

Nakajima et al., "Antitumor effect of CD40 ligand: elicitation of local and systemic antitumor responses by IL-12 and B7", *J. Immunol.*, 161:1901-1907 (1998).

Okayama, Hiroto and Paul Berg, "A cDNA Cloning Vector That Permits Expression of cDNA Inserts in Mammalian Cells", *Molecular and Cellular Biology*, 3:280-289 (1983).

Peitsch, Manuel C. et al., "A 3-D model for the CD40 ligand predicts that it is a compact trimer similar to the tumor necrosis factors", *International Immunology*, 5:233-238 (1993).

Perez et al., "Nonsecretable cell surface mutant of tumor necrosis factor TNF kills by cell-to-cell contact", *Cell*, 63(2):251-258(1990).

Pietravalle et al., "Cleavage of membrane-bound CD40 ligand is not required for inducing B cell proliferation and differentiation", *Eur. J. Immunol.*, 26:725-7 (1996).

Prentice, Howard et al., "Ischemic/Reperfused Myocardium Can Express Recombinant Protein Following Direct DNA or Retroviral Injection", *J. Mol. Cell Cardiol.*, 28:133-140 (1996).

Randrianarison-Jewtoukoff, Voahangy et al., "Recombinant Adenoviruses as Vaccines", *Biologicals*, 23:145-157 (1995).

Ranheim et al., "Activated T cells induce expression of B7/BB1 on normal or leukemic B cells through a CD40-dependent signal", *J. Exp. Med.*, 177:925-935 (1993).

Ranheim et al., "Tumor necrosis factor-alpha facilitates induction of CD80 (B7-1) and CD54 on human B cells by activated T cells: complex regulation by IL-4, IL-10, and CD40L", *Cell Immunol.*, 161:226-235 (1995).

Raper, Steven E. et al., "Safety and Feasibility of Liver-Directed Ex Vivo Gene Therapy for Homozygous Familial Hypercholesterolemia", *Annals of Surgery*, 223:111-126 (1996).

Rassenti, Laura Z. et al., "Lack of Allelic Exclusion in B Cell Chronic Lymphocytic Leukemia", *J. Exp. Med.*, 185:1435-1445 (1997).

Raz, Eyal et al., "Systemic immunological effects of cytokine genes injected into skeletal muscle", *Proc. Natl. Acad. Sci. U.S.A.*, 90:4523-4527 (1993).

Roy et al., "The regulation of the expression of gp39, the CD40 ligand, on normal and cloned CD4+ cells", *J. Immunol.*, 151:2497-2510 (1993).

Russell, S. J., "Replicating Vectors for Gene Therapy of Cancer: Risks, Limitations and Prospects", *European Journal of Cancer*, 30A:1165-1171 (1994).

Russell, Stephen J., "Replicating vectors for cancer therapy: a question of strategy", *Seminars in Cancer Biology*, 5:437-443 (1994).

Sambrook, J. et al., "Standard Protocol for Calcium Phosphate-mediated Transfection of Adherent Cells", *Molecular Cloning. A Laboratory Manual*, 2d edition, Chapter 16:33-37 (1989).

Sato, Ken et al., "An aggressive nasal lymphoma accompanied by high levels of soluble Fas ligand", *British Journal of Haematology*, 94:379-382 (1996).

Schultze, Joachim L. et al., "Autologous Tumor Infiltrating T Cells Cytotoxic for Follicular Lymphoma Cells Can Be Expanded in Vitro", *Blood*, 89:3806-3816 (1997).

Shaughnessy, Elizabeth et al., "Parvoviral Vectors for the Gene Therapy of Cancer", *Seminars in Oncology*, 23:159-171 (1996).

Skolnick et al., "From genes to protein structure and function: novel applications of computational approaches in the genomic era", *Trends in Biotech.*, 18(1):34-39 (2000).

Smith, K. T. et al., "Gene delivery systems for use in gene therapy: an overview of quality assurance and safety issues", *Gene Therapy*, 3:190-200 (1996).

Smith, Matthew M. et al., "Rapid Identification of Highly Active and Selective Substrates for Stromelysin and Matrilysin Using Bacteriophage Peptide Display Libraries", *The Journal of Biological Chemistry*, 270:6440-6449 (1995).

Soubrane, C. et al., "Direct Gene Transfer of a Plasmid Carrying the Herpes Simplex Virus-Thymidine Kinase Gene (HSV-TK) in Transplanted Murine Melanoma: In Vivo Study", *European Journal of Cancer*, 32A:691-695 (1996).

Spessot, Robert, "Cloning of the Herpes Simplex Virus ICP4 Gene in an Adenovirus Vector: Effects on Adenovirus Gene Expression and Replication", *Virology*, 168:378-387 (1989).

Srivastava, Arun, "Parvovirus-Based Vectors for Human Gene Therapy", *Blood Cells*, 20:531-538 (1994).

Stappert, Jorg et al., "A PCR method for introducing mutations into cloned DNA by joining an internal primer to a tagged flanking primer", *Nucleic Acids Research*, 20:624 (1992).

Sugaya, Susumu et al., "Inhibition of Tumor Growth by Direct Intratumoral Gene Transfer of Herpes Simplex Virus Thymidine Kinase Gene with DNA-Liposome Complexes", *Human Gene Therapy*, 7:223-230 (1996).

Tang et al., "Length of the linking domain of human pro-tumor necrosis factor determines the cleavage processing", *Biochemistry*, 35(25):8226-33 (1996).

Tesselaar, Kiki et al., "Characterization of Murine CD70, the Ligand of the TNF Receptor Family Member CD27", *The Journal of Immunology*, 159:4959-4965 (1997).

Tessier, Daniel C. et al., "PCR-Assisted Large Insertion/Deletion Mutagenesis", *BioTechniques*, 15:498-501 (1993).

Thomas, J. Alero et al., "Epstein-Barr Virus-Associated Lymphoproliferative Disorders in Immunocompromised Individuals", *Advances in Cancer Research*, Woude et al., eds., Academic Press, Inc., 57:329-380 (1991).

Tolstoshev, Paul, "Gene therapy, concepts, current trials and future directions", *Annu. Rev. Pharmacol. Toxicol.*, 33:573-596 (1993).

Tracey, Kevin J. et al., "Tumor Necrosis Factor: A Pleiotropic Cytokine and Therapeutic [sic] Target", Annu. Rev. Med., 45:491-503 (1994).

Vallejo, Abbe N. et al., "In Vitro Synthesis of Novel Genes: Mutagenesis and Recombination by PCR", *PCR Methods and Applications*, 4:S123-S130 (1994).

van Oers, M. H. J. et al., "Expression and Release of CD27 in Human B-Cell Malignancies", *Blood*, 82:3430-3436 (1993).

Vilardaga, J. P. et al., "Improved PCR Method for High-Efficiency Site-Directed Mutagenesis Using Class 2S Restriction Enzymes", *BioTechniques*, 18:604-606 (1995).

Vile, R. G. et al., "Retroviruses as vectors", British Medical Bulletin, 51:12-30 (1995).

Vile, R.G. et al., "Targeting of cytokine gene expression to malignant melanoma cells using tissue specific promoter sequences", *Annals of Oncology*, 5 Suppl 4:S59-S65 (1994).

Wierda et al. "CD40-ligand (CD154) gene therapy for chronic lymphocytic leukemia", *Blood*, 96:2917-2924 (2000).

Wierda et al., "Infection of B-cell lymphoma with adenovirus vector encoding CD40-ligand (CD154) induces phenotypic changes that allow for autologous immune recognition", *Blood*, 90: Abstract No. 2280, 1997.

Wiley, James A. et al., "Exogenous CD40 Ligand Induces a Pulmonary Inflammation Response", *Journal of Immunology*, 158:2932-2938 (1997).

Woll, P. J. et al., "Gene therapy for lung cancer", *Annals of Oncology*, 6 Suppl. 1:S73-S77 (1995).

Yee, Jiing-Kuan et al., "Generation of High-Tier Pseudotyped Retroviral Vectors with Very Broad Host Range", *Methods in Cell Biology*, Chapter 5, 43:99-112 (1994).

Yellin et al., "T lymphocyte T Cell-B Cell-activating molecule/CD40-L molecules induce normal B Cells or chronic lymphocytic leukemia B cells to express CD80 (B7/BB-1) and enhance their costimulatory activity", *J. Immun.* 153:666-674 (1994).

Yovandich, Jason et al., "Gene Transfer to Synovial Cells by Intra-Articular Administration of Plasmid DNA", *Human Gene Therapy*, 6:603-610 (1995).

Zhang, Haidi et al., "Amelioration of Collagen-induced Arthritis by CD95 (Apo-1/Fas)-ligand Gene Transfer", *J. Clin. Invest.*, 100:1951-1957 (1997).

Figure 1. ISF Domain Composition

Figure 2:
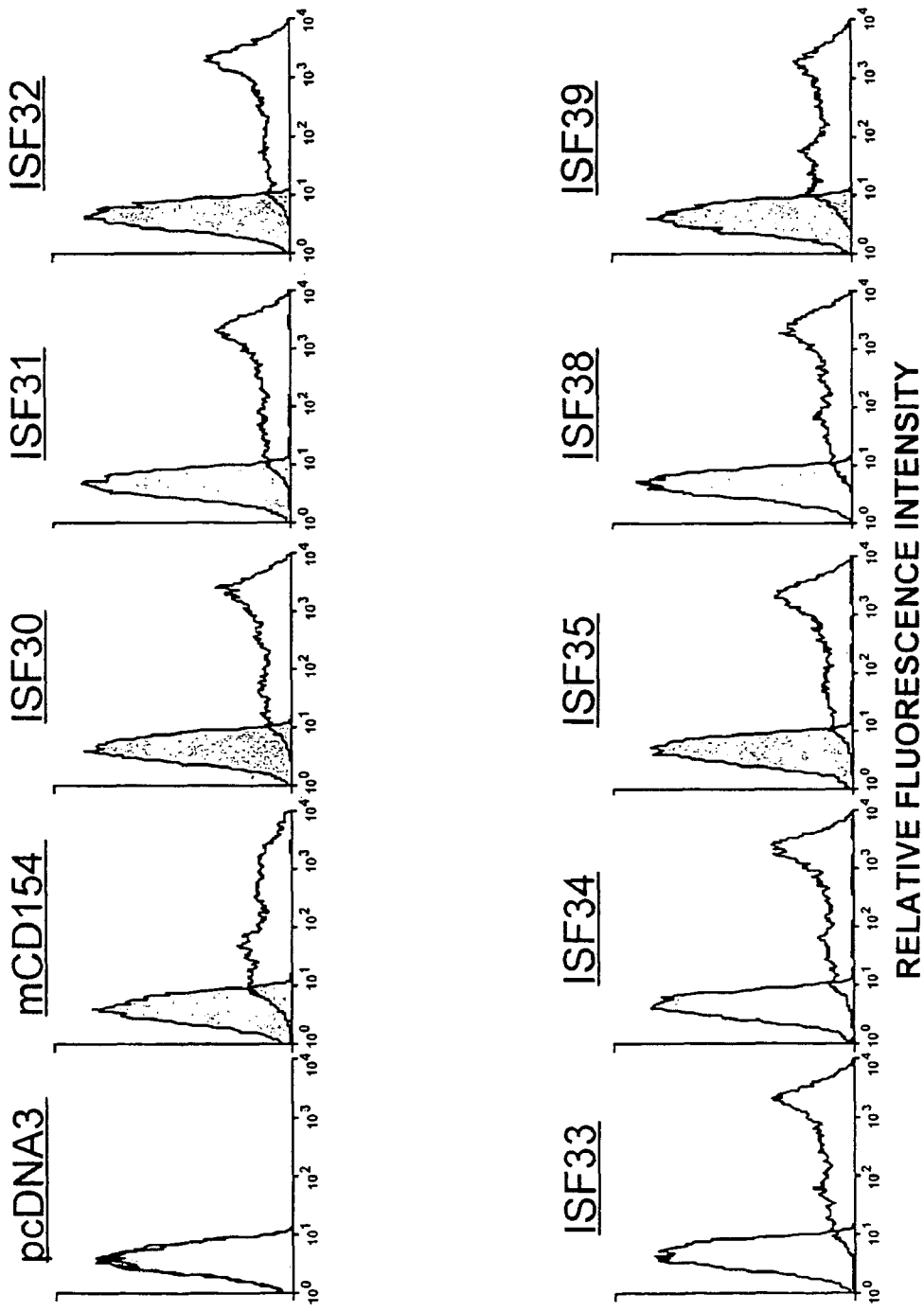

Figure 2. ISF Expression by HeLa Cells

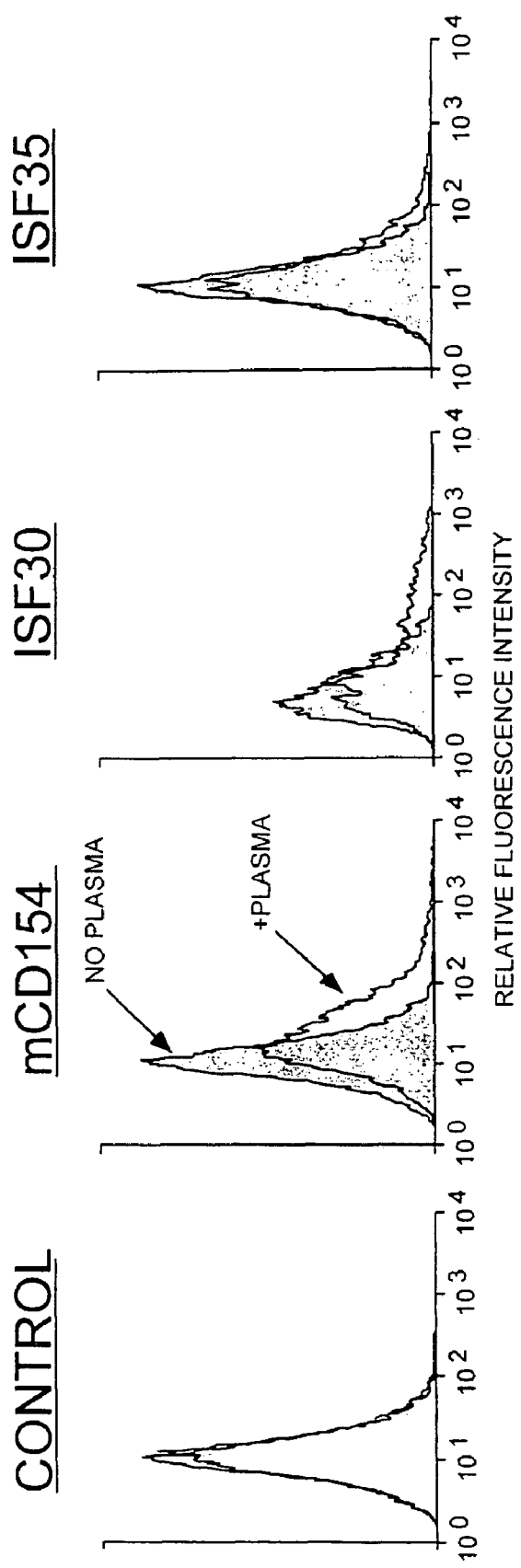
Figure 5. CD154-Specific Antibody Binding to ISF Constructs

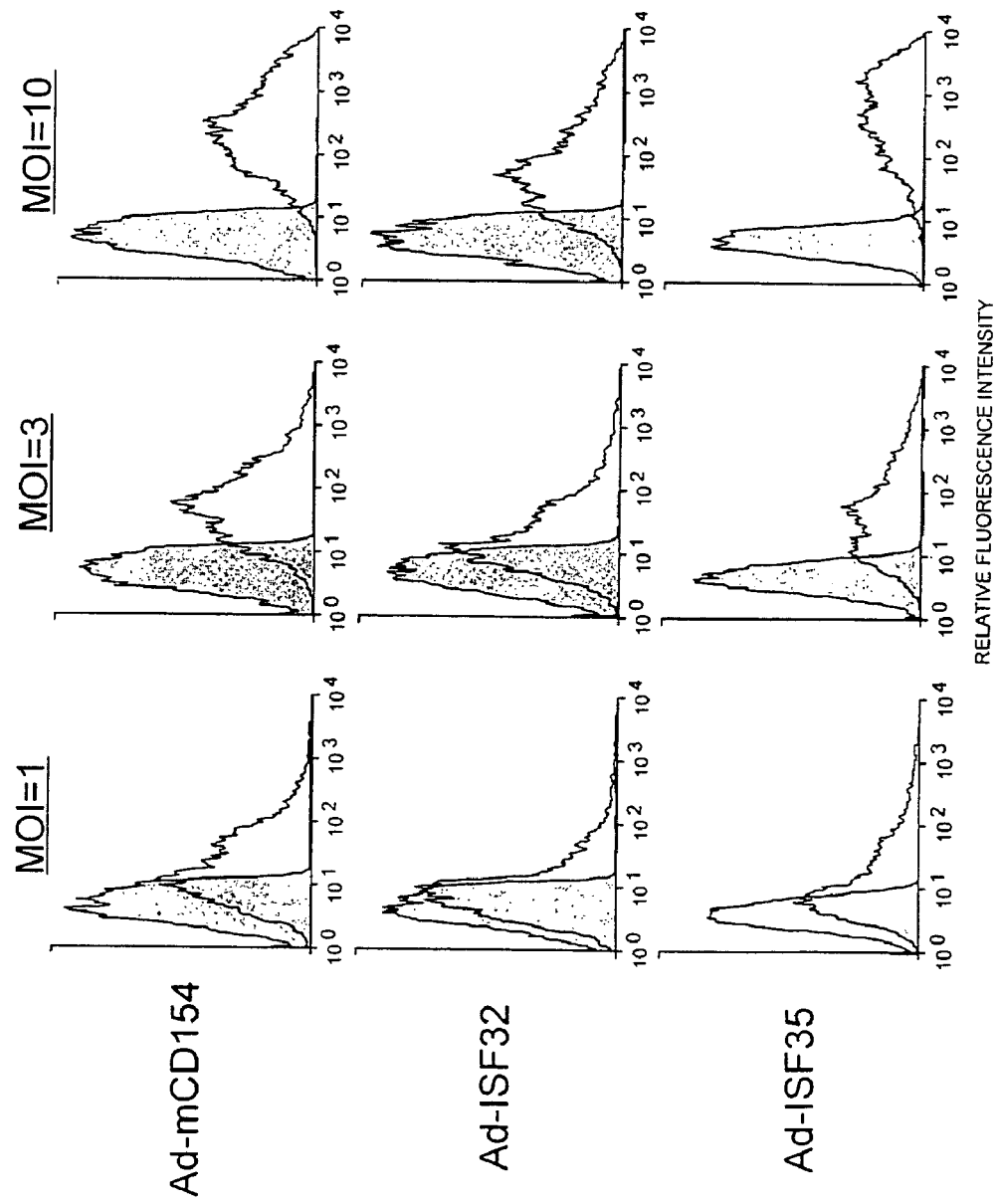
Figure 6. Ad-ISF Infection of HeLa Cells

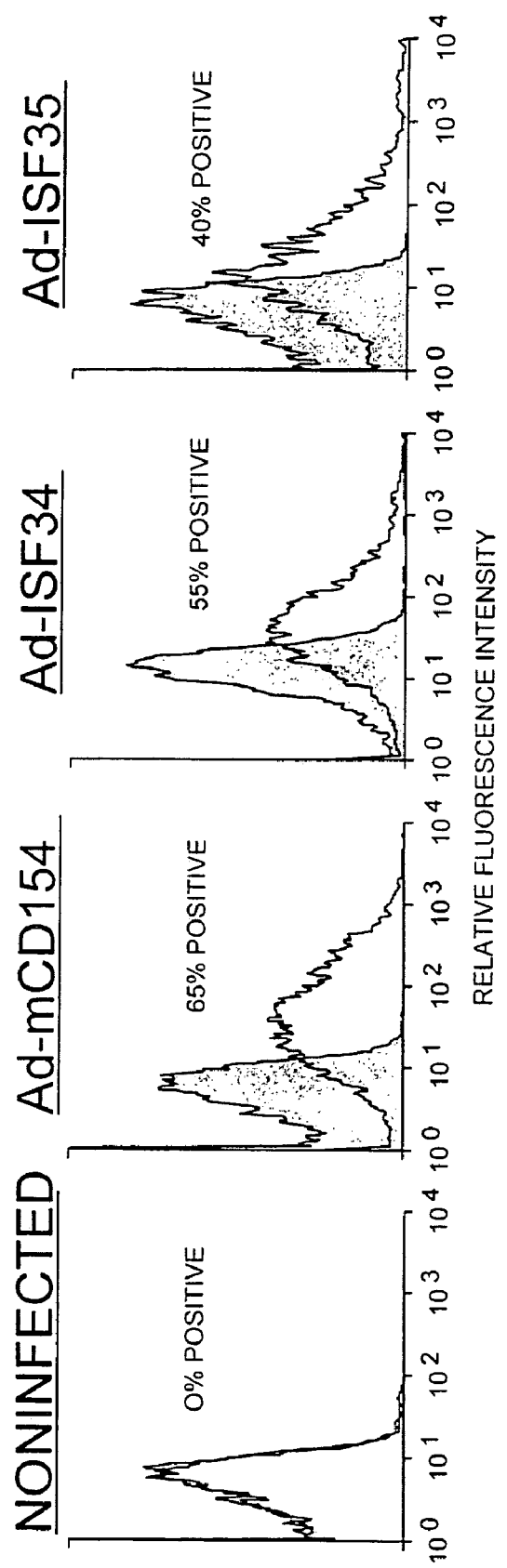
Figure 7. Ad-ISF Infection of CLL B Cells

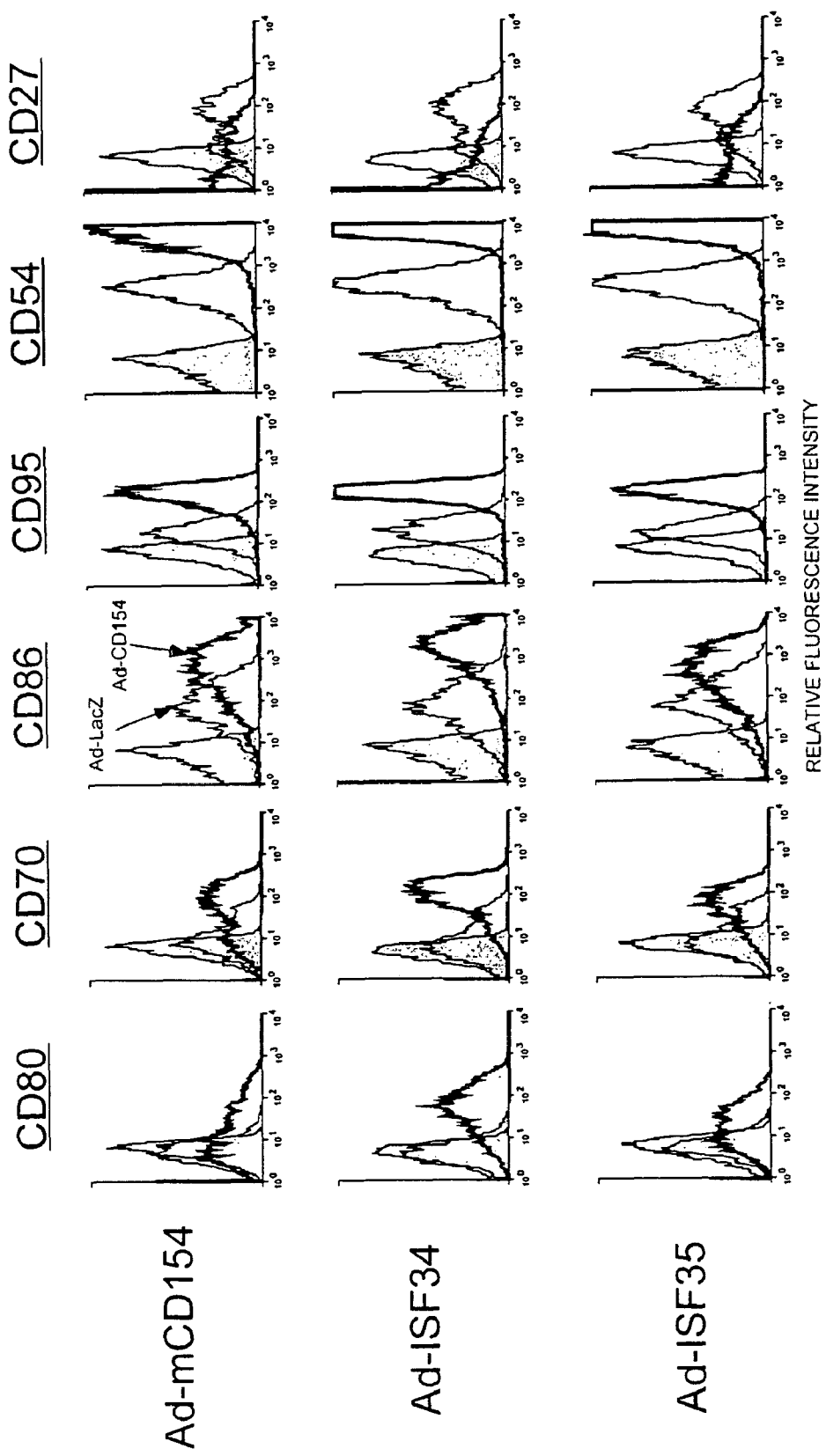
Figure 8. Ad-ISF Infected CLL Cell Activation

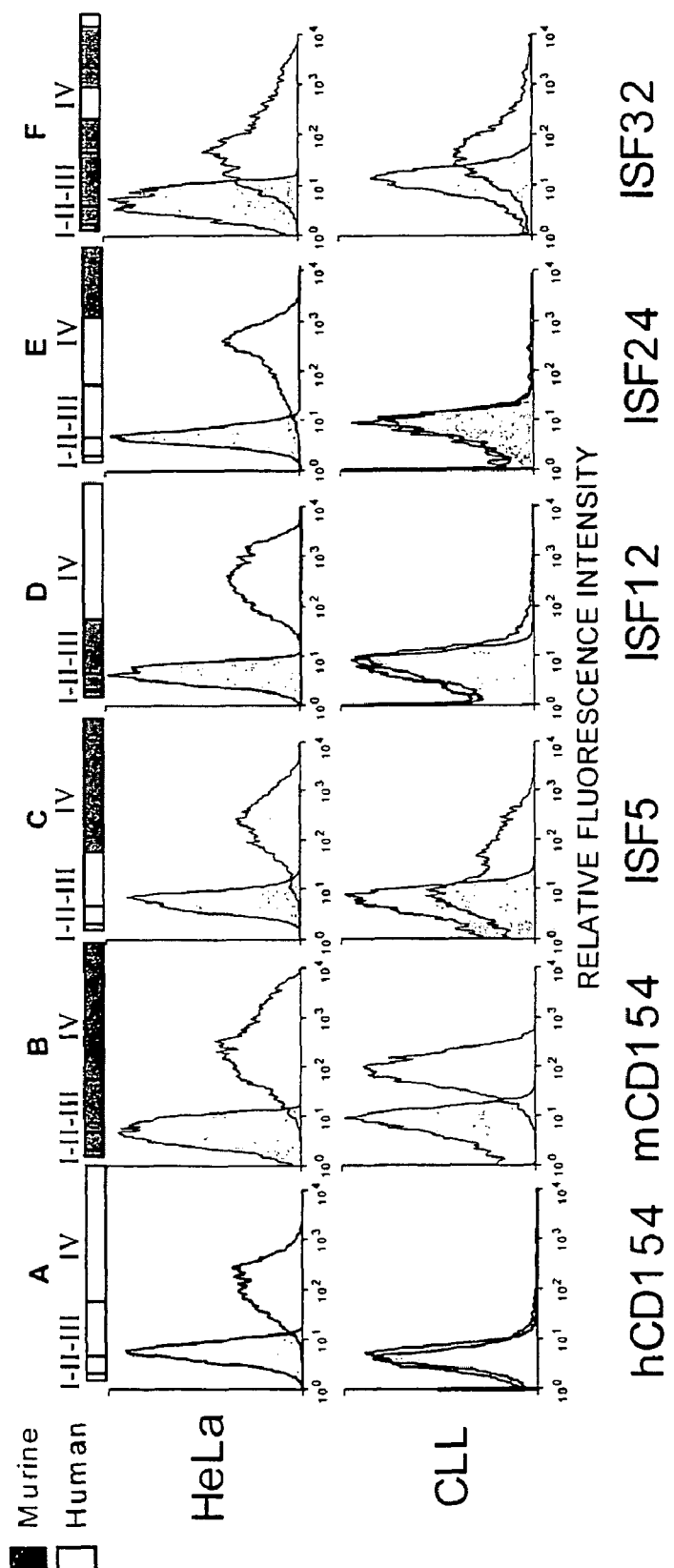
Figure 9. Mapping of The Regulatory Element Allowing for ISF Expression in CD40-positive Cells to Domain IV of CD154

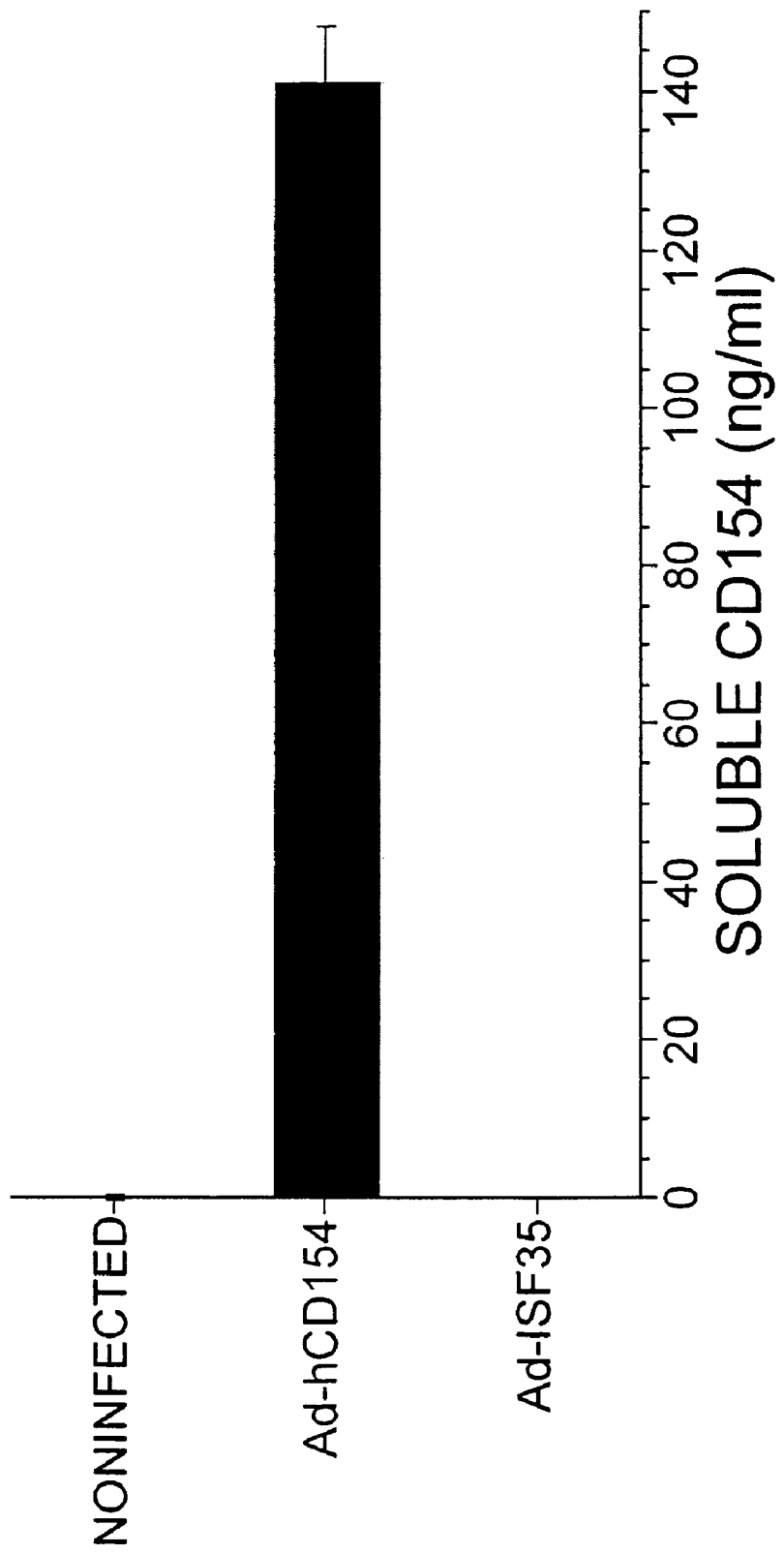
Figure 10. Resistance of ISF to Cleavage Into Soluble CD154

Figure 11(a): ISF30 Nucleotide Sequence Alignment With Human CD154

```
85.9% identity in 786 nt overlap; score: 2921 E(10,000): 2.7e-235

10         20         30         40         50         60
ISF30    ATGATAGAAACATACAGCCAACCTTCCCCCAGATCCGTGGCAACTGGACTTCCAGCGAGC
         ::::: ::::::::::::  :::: ::: :::: : ::: :::::::::  ::   :::
HUMAN    ATGATCGAAACATACAACCAAACTTCTCCCCGATCTGCGGCCACTGGACTGCCCATCAGC
              10         20         30         40         50         60

70         80         90        100        110        120
ISF30    ATGAAGATTTTTATGTATTTACTTACTGTTTTCCTTATCACCCAAATGATTGGATCTGTG
         ::::: ::::::::::::::::::::::::: ::::::::::: ::::::::  :  :
HUMAN    ATGAAAATTTTTATGTATTTACTTACTGTTTTTCTTATCACCCAGATGATTGGGTCAGCA
              70         80         90        100        110        120

130        140        150        160        170        180
ISF30    CTTTTTGCTGTGTATCTTCATAGAAGATTGGATAAGGTCGAAGAGGAAGTAAACCTTCAT
         :::::::::::::::::::::::::::: ::::: ::: : ::::: :::  :: :::::
HUMAN    CTTTTTGCTGTGTATCTTCATAGAAGGTTGGACAAGATAGAAGATGAAAGGAATCTTCAT
             130        140        150        160        170        180

190        200        210        220        230        240
ISF30    GAAGATTTTGTATTCATAAAAAAAGCTAAAGAGATGCAACAAAGGAGAAGGATCTTTATCC
         :::::::::::::::::: :  : :::::::::::::::::  :::::::::  ::::::
HUMAN    GAAGATTTTGTATTCATGAAAAACGATACAGAGATGCAACACAGGAGAAAGATCCTTATCC
             190        200        210        220        230        240

250        260        270        280        290        300
ISF30    TTGCTGAACTGTGAGGAGATGAGAAGGCAATTTGAAGACCTTGTCAAGGATATAACGTTA
         ::  ::::::::::::::::  : ::: :: ::::::: : ::::  ::::::::: ::::
HUMAN    TTACTGAACTGTGAGGAGATTAAAAGCCAGTTTGAAGGCTTTGTGAAGGATATAATGTTA
             250        260        270        280        290        300

310        320        330        340        350
ISF30    AACAAAGAAGAGA---AAAAAGAAAAACAGCTTTGAAATGCAAAGAGGTGATGAGGATCCT
         ::::::::  ::::    : ::::::::::::::::::::::::::  :::::: : :::::
HUMAN    AACAAAGAGGAGACGAAGAAAGAAAAACAGCTTTGAAATGCAAAAGGTGATCAGAATCCT
             310        320        330        340        350        360

360        370        380        390        400        410
ISF30    CAAATTGCAGCACACGTTGTAAGCGAAGCCAACAGTAATGCAGCATCCGTTCTACAGTGG
         :::::::: :::::: ::   :::: :: :::: ::::: :: ::::`:: ::::::::::
HUMAN    CAAATTGCGGCACATGTCATAAGTGAGGCCAGCAGTAAAACAACATCTGTGTTACAGTGG
             370        380        390        400        410        420

420        430        440        450        460        470
ISF30    GCCAAGAAAGGATATTATACCATGAAAAGC AACTTGGTAACCCTGGAAAATGGAAACAG
         :: : :::::::: :: ::::::: :  :  : :::::::::::::::::::::::::::::
HUMAN    GCTGAAAAAGGATACTACACCATGAGCAAC AACTTGGTAACCCTGGAAAATGGAAACAG
             430        440        450        460        470        480

480        490        500        510        520        530
ISF30    CTGACGGTTAAAAGACAAGGACTCTATTATATCTATGCTCAAGTCACCTTCTGCTCTAAT
         ::::: ::::::::::::::::::::::::::::::::: :::::::::::::: :: :::
HUMAN    CTGACCGTTAAAAGACAAGGACTCTATTATATCTATGCCCAAGTCACCTTCTGTTCCAAT
             490        500        510        520        530        540

540        550        560        570        580        590
ISF30    CGGGAGCCTTCGAGTCAACGCCCATTCATCGTCGGCCTCTGGCTGAAGCCCAGCAGTGGA
         ::::: :::::::::::::: :::::: :: : :::::: :: :::: :: :  : :: ::
HUMAN    CGGGAAGCTTCGAGTCAAGCTCCATTTATAGCCAGCCTCTGCCTAAAGTCCCCCGGTAGA
             550        560        570        580        590        600

600        610        620        630        640        650
ISF30    TCTGAGAGAATCTTACTCAAGGCGGCAAATACCCACAGTTCCTCCCAGCTTTGCGAGCAG
         :  :::::::::::::::::::  :: ::::::::::::::: :: :: ::::: ::::::
HUMAN    TTCGAGAGAATCTTACTCAGAGCTGCAAATACCCACAGTTCGCCAAACCTTGCGGGCAA
             610        620        630        640        650        660

660        670        680        690        700        710
ISF30    CAGTCTGTTCACTTGGGCGGAGTGTTTGAATTACAACCAGGTGCTTCGGTGTTTGTCAAT
         :: ::  ::::::::::::::: ::::::: ::::::::::::::::::::::::::::::
HUMAN    CAATCCATTCACTTGGGAGGAGTATTTGAATTGCAACCAGGTGCTTCGGTGTTTGTCAAT
             670        680        690        700        710        720

720        730        740        750        760        770
ISF30    GTGACTGATCCAAGCCAAGTGAGCCATGGCACTGGCTTCACGTCCTTTGGCTTACTCAAA
         ::::::::::::::::::::::::::::::::::::::::::::::::::::::::::::
HUMAN    GTGACTGATCCAAGCCAAGTGAGCCATGGCACTGGCTTCACGTCCTTTGGCTTACTCAAA
             730        740        750        760        770        780

780
ISF30    CTCTGA
         ::::::
HUMAN    CTCTGA
```

Figure 11(b): ISF30 Nucleotide Sequence Alignment With Murine CD154

```
97.1% identity in 783 nt overlap; score: 3708 E(10,000): 6.4e-301

10         20         30         40         50         60
ISF30   ATGATAGAAACATACAGCCAACCTTCCCCCAGATCCGTGGCAACTGGACTTCCAGCGAGC
        ::::::::::::::::::::::::::::::::::::::::::::::::::::::::::::
MURINE  ATGATAGAAACATACAGCCAACCTTCCCCCAGATCCGTGGCAACTGGACTTCCAGCGAGC
               10         20         30         40         50         60

70         80         90        100        110        120
ISF30   ATGAAGATTTTTATGTATTTACTTACTGTTTTCCTTATCACCCAAATGATTGGATCTGTG
        ::::::::::::::::::::::::::::::::::::::::::::::::::::::::::::
MURINE  ATGAAGATTTTTATGTATTTACTTACTGTTTTCCTTATCACCCAAATGATTGGATCTGTG
               70         80         90        100        110        120

130        140        150        160        170        180
ISF30   CTTTTTGCTGTGTATCTTCATAGAAGATTGGATAAGGTCGAAGAGGAAGTAAACCTTCAT
        :::::::::::::::::::::::::::::::::::::::::::::::::::::::::::
MURINE  CTTTTTGCTGTGTATCTTCATAGAAGATTGGATAAGGTCGAAGAGGAAGTAAACCTTCAT
              130        140        150        160        170        180

190        200        210        220        230        240
ISF30   GAAGATTTTGTATTCATAAAAAAGCTAAAGAGATGCAACAAAGGAGAAGGATCTTTATCC
        ::::::::::::::::::::::::::::::::::::::::::::::::::::::::::::
MURINE  GAAGATTTTGTATTCATAAAAAAGCTAAAGAGATGCAACAAAGGAGAAGGATCTTTATCC
              190        200        210        220        230        240

250        260        270        280        290        300
ISF30   TTGCTGAACTGTGAGGAGATGAGAAGGCAATTTGAAGACCTTGTCAAGGATATAACGTTA
        ::::::::::::::::::::::::::::::::::::::::::::::::::::::::::::
MURINE  TTGCTGAACTGTGAGGAGATGAGAAGGCAATTTGAAGACCTTGTCAAGGATATAACGTTA
              250        260        270        280        290        300

310        320        330        340        350        360
ISF30   AACAAAGAAGAGAAAAAAGAAAACAGCTTTGAAATGCAAAGAGGTGATGAGGATCCTCAA
        ::::::::::::::::::::::::::::::::::::::::::::::::::::::::::::
MURINE  AACAAAGAAGAGAAAAAAGAAAACAGCTTTGAAATGCAAAGAGGTGATGAGGATCCTCAA
              310        320        330        340        350        360

370        380        390        400        410        420
ISF30   ATTGCAGCACACGTTGTAAGCGAAGCCAACAGTAATGCAGCATCCGTTCTACAGTGGGCC
        ::::::::::::::::::::::::::::::::::::::::::::::::::::::::::::
MURINE  ATTGCAGCACACGTTGTAAGCGAAGCCAACAGTAATGCAGCATCCGTTCTACAGTGGGCC
              370        380        390        400        410        420

430        440        450        460        470        480
ISF30   AAGAAAGGATATTATACCATGAAAAGCAACTTGGTAACCCTGGAAAATGGGAAACAGCTG
        :::::::::::::::::::::::::::::::::::::  :::::::::::::::::::::
MURINE  AAGAAAGGATATTATACCATGAAAAGCAACTTGGTAATGCTTGAAAATGGGAAACAGCTG
              430        440        450        460        470        480

490        500        510        520        530        540
ISF30   ACGGTTAAAAGACAAGGACTCTATTATATCTATGCTCAAGTCACCTTCTGCTCTAATCGG
        :::::::::: ::::::::::::::::::: ::::::: :::::::::::::::::::::
MURINE  ACGGTTAAAAGAGAAGGACTCTATTATGTCTACACTCAAGTCACCTTCTGCTCTAATCGG
              490        500        510        520        530        540

550        560        570        580        590        600
ISF30   GAGCCTTCGAGTCAACGCCCATTCATCGTCGGCCTCTGGCTGAAGCCCAGCAGTGGATCT
        ::::::::::::::::::::::::::::::::::::::::::::::::::::: ::::::
MURINE  GAGCCTTCGAGTCAACGCCCATTCATCGTCGGCCTCTGGCTGAAGCCCAGCATTGGATCT
              550        560        570        580        590        600

610        620        630        640        650        660
ISF30   GAGAGAATCTTACTCAAGGCGGCAAATACCCACAGTTCCTCCCAGCTTTGCGAGCAGCAG
        ::::::::::::::::::::::::::::::::::::::::::::::::::::::::::::
MURINE  GAGAGAATCTTACTCAAGGCGGCAAATACCCACAGTTCCTCCCAGCTTTGCGAGCAGCAG
              610        620        630        640        650        660

670        680        690        700        710        720
ISF30   TCTGTTCACTTGGGCGGAGTGTTTGAATTACAACCAGGTGCTTCGGTGTTTGTCAATGTG
        ::::::::::::::::::::::::::::::::::: :::::: ::: :::::::  ::::
MURINE  TCTGTTCACTTGGGCGGAGTGTTTGAATTACAAGCTGGTGCTTCTGTGTTTGTCAACGTG
              670        680        690        700        710        720

730        740        750        760        770        780
ISF30   ACTGATCCAAGCCAAGTGAGCCATGGCACTGGCTTCACGTCCTTTGGCTTACTCAAACTC
        ::::  :::::::::::: ::   :::: :  :::::::  ::: :::::::::::::::
MURINE  ACTGAAGCAAGCCAAGTGATCCACAGAGTTGGCTTCTCATCTTTTGGCTTACTCAAACTC
              730        740        750        760        770        780

ISF30   TGA
        :::
MURINE  TGA
```

Figure 12(a): ISF32 Nucleotide Sequence Alignment With Human CD154

```
86.3% identity in 786 nt overlap; score: 2948 E(10,000): 1.5e-237

10        20        30        40        50        60
ISF32   ATGATAGAAACATACAGCCAACCTTCCCCCAGATCCGTGGCAACTGGACTTCCAGCGAGC
        :::: :::::::::::: :::: ::::  ::: ::::  ::: ::::::::  :   :::
HUMAN   ATGATCGAAACATACAACCAAACTTCTCCCCGATCTGCGGCCACTGGACTGCCCATCAGC
               10        20        30        40        50        60

70        80        90       100       110       120
ISF32   ATGAAGATTTTTATGTATTTACTTACTGTTTTCCTTATCACCCAAATGATTGGATCTGTG
        ::::: :::::::::::::::::::::::::::  :::::::::: :::::::: :: :
HUMAN   ATGAAAATTTTTATGTATTTACTTACTGTTTTTCTTATCACCCAGATGATTGGGTCAGCA
               70        80        90       100       110       120

130       140       150       160       170       180
ISF32   CTTTTTGCTGTGTATCTTCATAGAAGATTGGATAAGGTCGAAGAGGAAGTAAACCTTCAT
        ::::::::::::::::::::::::::::  :::: :::  ::::: :::   :::::::
HUMAN   CTTTTTGCTGTGTATCTTCATAGAAGGTTGGACAAGATAGAAGATGAAAGGAATCTTCAT
              130       140       150       160       170       180

190       200       210       220       230       240
ISF32   GAAGATTTTGTATTCATAAAAAAGCTAAAGAGATGCAACAAAGGAGAAGGATCTTTATCC
        :::::::::::::::::  ::::  ::  :::::::::::: ::::::::: :::::::
HUMAN   GAAGATTTTGTATTCATGAAAACGATACAGAGATGCAACACAGGAGAAAGATCCTTATCC
              190       200       210       220       230       240

250       260       270       280       290       300
ISF32   TTGCTGAACTGTGAGGAGATGAGAAGGCAATTTGAAGACCTTGTCAAGGATATAACGTTA
        :: :::::::::::::::::: : :::  :: :::::  :::: :::::::::::  ::::
HUMAN   TTACTGAACTGTGAGGAGATTAAAAGCCAGTTTGAAGGCTTTGTGAAGGATATAATGTTA
              250       260       270       280       290       300

310       320       330       340       350
ISF32   AACAAAGAAGAGA---AAAAAGAAAACAGCTTTGAAATGCAAAGAGGTGATGAGGATCCT
        :::::::: ::::   : ::::::::::::::::::::::::::  ::::: :: :::::
HUMAN   AACAAAGAGGAGACGAAGAAAGAAAACAGCTTTGAAATGCAAAAAGGTGATCAGAATCCT
              310       320       330       340       350       360

360       370       380       390       400       410
ISF32   CAAATTGCAGCACACGTTGTAAGCGAAGCCAACAGTAATGCAGCATCCGTTCTACAGTGG
        ::::::::: ::::::: :  :::: :: ::::::::: ::  :::: :::: ::::::::
HUMAN   CAAATTGCGGCACATGTCATAAGTGAGGCCAGCAGTAAAACAACATCTGTGTTACAGTGG
              370       380       390       400       410       420

420       430       440       450       460       470
ISF32   GCCAAGAAAGGATATTATACCATGAAAAGC AACTTGGTAACCCTGGAAAATGGGAAACAG
        ::  :  :::::::: ::  :::::::  :  ::::::::::::::::::::::::::::
HUMAN   GCTGAAAAAGGATACTACACCATGAGCAAC AACTTGGTAACCCTGGAAAATGGGAAACAG
              430       440       450       460       470       480

480       490       500       510       520       530
ISF32   CTGACGGTTAAAAGACAAGGACTCTATTATATCTATGCTCAAGTCACCTTCTGCTCTAAT
        :::::  :::::::::::::::::::::::::::::::  :::::::::::::: :: :::
HUMAN   CTGACCGTTAAAAGACAAGGACTCTATTATATCTATGCCCAAGTCACCTTCTGTTCCAAT
              490       500       510       520       530       540

540       550       560       570       580       590
ISF32   CGGGAGGCTTCGAGTCAAGCCCCATTCATC GTCGGCCTCTGGCTGAAGCCCAGCAGTGGA
        :::::  ::::::::::::   :::  ::    :::::::::  :::    ::: :: :
HUMAN   CGGGAAGCTTCGAGTCAAGCTCCATTTATA GCCAGCCTCTGCCTAAAGTCCCCCGGTAGA
              550       560       570       580       590       600

600       610       620       630       640       650
ISF32   TCTGAGAGAATCTTACTCAAGGCGGCAAATACCCACAGTTCCTCCAGCTTTGCGAGCAG
        :  :::::::::::::::::::  ::::::::::::::::::::: :::::: :::: :::
HUMAN   TTCGAGAGAATCTTACTCAGAGCTGCAAATACCCACAGTTCCGCCAAACCTTGCGGGCAA
              610       620       630       640       650       660

660       670       680       690       700       710
ISF32   CAGTCTGTT CACTTGGGCGGAGTGTTTGAATTACAACCAGGTGCTTCGGTGTTTGTCAAT
        ::  :::: ::::: :::::  :::  ::  ::::::::::::::::::::::::::::
HUMAN   CAATCCATT CACTTGGGAGGAGTATTTGAATTGCAACCAGGTGCTTCGGTGTTTGTCAAT
              670       680       690       700       710       720

720       730       740       750       760       770
ISF32   GTGACTGATCCAAGCCAAGTGAGCCATGGCACTGGCTTCACGTCCTTTGGCTTACTCAAA
        :::::::::::::::::::::::::::::::::::::::::::: :::::::::::::::
HUMAN   GTGACTGATCCAAGCCAAGTGAGCCATGGCACTGGCTTCACGTCCTTTGGCTTACTCAAA
              730       740       750       760       770       780

780
ISF32   CTCTGA
        ::::::
HUMAN   CTCTGA
```

Figure 12(b): ISF32 Nucleotide Sequence Alignment With Murine CD154
96.7% identity in 783 nt overlap; score: 3681 E(10,000): 1.1e-298

```
              10         20         30         40         50         60
ISF32   ATGATAGAAACATACAGCCAACCTTCCCCCAGATCCGTGGCAACTGGACTTCCAGCGAGC
        ::::::::::::::::::::::::::::::::::::::::::::::::::::::::::::
MURINE  ATGATAGAAACATACAGCCAACCTTCCCCCAGATCCGTGGCAACTGGACTTCCAGCGAGC
              10         20         30         40         50         60

70         80         90        100        110        120
ISF32   ATGAAGATTTTTATGTATTTACTTACTGTTTTCCTTATCACCCAAATGATTGGATCTGTG
        ::::::::::::::::::::::::::::::::::::::::::::::::::::::::::::
MURINE  ATGAAGATTTTTATGTATTTACTTACTGTTTTCCTTATCACCCAAATGATTGGATCTGTG
              70         80         90        100        110        120

130        140        150        160        170        180
ISF32   CTTTTTGCTGTGTATCTTCATAGAAGATTGGATAAGGTCGAAGAGGAAGTAAACCTTCAT
        ::::::::::::::::::::::::::::::::::::::::::::::::::::::::::::
MURINE  CTTTTTGCTGTGTATCTTCATAGAAGATTGGATAAGGTCGAAGAGGAAGTAAACCTTCAT
             130        140        150        160        170        180

190        200        210        220        230        240
ISF32   GAAGATTTTGTATTCATAAAAAAGCTAAAGAGATGCAACAAAGGAGAAGGATCTTTATCC
        ::::::::::::::::::::::::::::::::::::::::::::::::::::::::::::
MURINE  GAAGATTTTGTATTCATAAAAAAGCTAAAGAGATGCAACAAAGGAGAAGGATCTTTATCC
             190        200        210        220        230        240

250        260        270        280        290        300
ISF32   TTGCTGAACTGTGAGGAGATGAGAAGGCAATTTGAAGACCTTGTCAAGGATATAACGTTA
        ::::::::::::::::::::::::::::::::::::::::::::::::::::::::::::
MURINE  TTGCTGAACTGTGAGGAGATGAGAAGGCAATTTGAAGACCTTGTCAAGGATATAACGTTA
             250        260        270        280        290        300

310        320        330        340        350        360
ISF32   AACAAAGAAGAGAAAAAAGAAAACAGCTTTGAAATGCAAAGAGGTGATGAGGATCCTCAA
        ::::::::::::::::::::::::::::::::::::::::::::::::::::::::::::
MURINE  AACAAAGAAGAGAAAAAAGAAAACAGCTTTGAAATGCAAAGAGGTGATGAGGATCCTCAA
             310        320        330        340        350        360

370        380        390        400        410        420
ISF32   ATTGCAGCACACGTTGTAAGCGAAGCCAACAGTAATGCAGCATCCGTTCTACAGTGGGCC
        ::::::::::::::::::::::::::::::::::::::::::::::::::::::::::::
MURINE  ATTGCAGCACACGTTGTAAGCGAAGCCAACAGTAATGCAGCATCCGTTCTACAGTGGGCC
             370        380        390        400        410        420

430        440        450        460        470        480
ISF32   AAGAAAGGATATTATACCATGAAAAGCAACTTGGTAACCCTGGAAAATGGGAAACAGCTG
        :::::::::::::::::::::::::::::::::::::::: ::  :::::::::::::::
MURINE  AAGAAAGGATATTATACCATGAAAAGCAACTTGGTAATGCTTGAAAATGGGAAACAGCTG
             430        440        450        460        470        480

490        500        510        520        530        540
ISF32   ACGGTTAAAAGACAAGGACTCTATTATATCTATGCTCAAGTCACCTTCTGCTCTAATCGG
        :::::::::::: ::::::::::::::::: ::::  :::::::::::::::::::::::
MURINE  ACGGTTAAAAGAGAAGGACTCTATTATGTCTACACTCAAGTCACCTTCTGCTCTAATCGG
             490        500        510        520        530        540

550        560        570        580        590        600
ISF32   GAGGCTTCGAGTCAAGCCCCATTCATCGTCGGCCTCTGGCTGAAGCCCAGCAGTGGATCT
        ::: :::::::::::: :::::::::::::::::::::::::::::::::::  ::::::
MURINE  GAGCCTTCGAGTCAACGCCCCATTCATCGTCGGCCTCTGGCTGAAGCCCAGCATTGGATCT
             550        560        570        580        590        600

610        620        630        640        650        660
ISF32   GAGAGAATCTTACTCAAGGCGGCAAATACCCACAGTTCCTCCCAGCTTTGCGAGCAGCAG
        ::::::::::::::::::::::::::::::::::::::::::::::::::::::::::::
MURINE  GAGAGAATCTTACTCAAGGCGGCAAATACCCACAGTTCCTCCCAGCTTTGCGAGCAGCAG
             610        620        630        640        650        660

670        680        690        700        710        720
ISF32   TCTGTTCACTTGGGCGGAGTGTTTGAATTACAACCAGGTGCTTCGGTGTTTGTCAATGTG
        ::::::::::::::::::::::::::::::::  ::::::::  : :::::::::: :::
MURINE  TCTGTTCACTTGGGCGGAGTGTTTGAATTACAAGCTGGTGCTTCTGTGTTTGTCAACGTG
             670        680        690        700        710        720

730        740        750        760        770        780
ISF32   ACTGATCCAAGCCAAGTGAGCCATGGCACTGGCTTCACGTCCTTTGGCTTACTCAAACTC
        :::::  :::::::::::::::  :::   :  ::::::::  :  ::::::::::::::
MURINE  ACTGAAGCAAGCCAAGTGATCCACAGAGTTGGCTTCTCATCTTTTGGCTTACTCAAACTC
             730        740        750        760        770        780

ISF32   TGA
        :::
MURINE  TGA
```

Figure 13(a): ISF34 Nucleotide Sequence Alignment With Human CD154

```
86.4% identity in 786 nt overlap; score: 2957 E(10,000): 2.7e-238

10        20        30        40        50        60
ISF34    ATGATAGAAACATACAGCCAACCTTCCCCCAGATCCGTGGCAACTGGACTTCCAGCGAGC
         :::::  :::::::::  :::: ::::  :::  : ::: :::::::::: :::  :::
HUMAN    ATGATCGAAACATACAACCAAACTTCTCCCCGATCTGCGGCCACTGGACTGCCCATCAGC
                 10        20        30        40        50        60

70        80        90       100       110       120
ISF34    ATGAAGATTTTTATGTATTTACTTACTGTTTTCCTTATCACCCAAATGATTGGATCTGTG
         ::::: :::::::::::::::::::::::::: :::::::::: :::::::::: :: :
HUMAN    ATGAAAATTTTTATGTATTTACTTACTGTTTTTCTTATCACCCAGATGATTGGGTCAGCA
                 70        80        90       100       110       120

130       140       150       160       170       180
ISF34    CTTTTTGCTGTGTATCTTCATAGAAGATTGGATAAGGTCGAAGAGGAAGTAAACCTTCAT
         ::::::::::::::::::::::::: ::::: :::  :::::: :::   ::  ::::::
HUMAN    CTTTTTGCTGTGTATCTTCATAGAAGGTTGGACAAGATAGAAGATGAAAGGAATCTTCAT
                130       140       150       160       170       180

190       200       210       220       230       240
ISF34    GAAGATTTTGTATTCATAAAAAAGCTAAAGAGATGCAACAAAGGAGAAGGATCTTTATCC
         :::::::::::::::: ::::: ::: :: :::::::::: ::::::: :::: ::::::
HUMAN    GAAGATTTTGTATTCATGAAAACGATACAGAGATGCAACACAGGAGAAAGATCCTTATCC
                190       200       210       220       230       240

250       260       270       280       290       300
ISF34    TTGCTGAACTGTGAGGAGATGAGAAGGCAATTTGAAGACCTTGTCAAGGATATAACGTTA
         :: :::::::::::::::::: ::  ::::: ::::::: ::::::::::::::: ::::
HUMAN    TTACTGAACTGTGAGGAGATTAAAAGCCAGTTTGAAGGCTTTGTGAAGGATATAATGTTA
                250       260       270       280       290       300

310       320       330       340       350
ISF34    AACAAAGAAGAGA---AAAAAGAAAACAGCTTTGAAATGCAAAGAGGTGATGAGGATCCT
         :::::::: ::::   : :::::::::::::::::::::::::::::::::  :: :::::
HUMAN    AACAAAGAGGAGACGAAGAAAGAAAACAGCTTTGAAATGCAAAAAGGTGATCAGAATCCT
                310       320       330       340       350       360

360       370       380       390       400       410
ISF34    CAAATTGCAGCACACGTTGTAAGCGAAGCCAACAGTAATGCAGCATCCGTTCTACAGTGG
         :::::::: ::::: :::: :::: ::::: ::::::  :::: ::: :: ::::::::
HUMAN    CAAATTGCGGCACATGTCATAAGTGAGGCCAGCAGTAAAACAACATCTGTGTTACAGTGG
                370       380       390       400       410       420

420       430       440       450       460       470
ISF34    GCCAAGAAAGGATATTATACCATGAAAAGCAACTTGGTAACCCTGGAAAATGGGAAACAG
         ::  :::::::::::  :: ::::::::   ::::::::::::::::::::::::::::
HUMAN    GCTGAAAAAGGATACTACACCATGAGCAACAACTTGGTAACCCTGGAAAATGGGAAACAG
                430       440       450       460       470       480

480       490       500       510       520       530
ISF34    CTGACGGTTAAAAGACAAGGACTCTATTATATCTATGCTCAAGTCACCTTCTGCTCTAAT
         :::: ::::::::::::::::: :::::::::::::::  :::::::::::::: :::::
HUMAN    CTGACCGTTAAAAGACAAGGACTCTATTATATCTATGCCCAAGTCACCTTCTGTTCCAAT
                490       500       510       520       530       540

540       550       560       570       580       590
ISF34    CGGGAGGCTTCGAGTCAAGCCCCATTCATC GTCGGCCTCTGGCTGAAGCCCAGCAGTGGA
         ::::: ::::::::::::::: :::::: :  : ::::::: :: :: :::  : ::
HUMAN    CGGGAAGCTTCGAGTCAAGCTCCATTTATA GCCAGCCTCTGCCTAAAGTCCCCCGGTAGA
                550       560       570       580       590       600

600       610       620       630       640       650
ISF34    TCTGAGAGAATCTTACTCAAGGCGGCAAATACCCACAGTTCCTCCCAGCTTTGCGAG CAG
         : ::::::::::::::: :::  ::::::::::::::::: :: ::::  :::::: ::
HUMAN    TTCGAGAGAATCTTACTCAGAGCTGCAAATACCCACAGTTCCGCCAAACCTTGCGGG CAA
                610       620       630       640       650       660

660       670       680       690       700       710
ISF34    CAGTCTATTCACTTGGGCGGAGTGTTTGAATTACAACCAGGTGCTTCGGTGTTTGTCAAT
         :: :: ::::::::::: ::::: ::::::: :::::::::::::::::::::::::::
HUMAN    CAATCCATTCACTTGGGAGGAGTATTTGAATTGCAACCAGGTGCTTCGGTGTTTGTCAAT
                670       680       690       700       710       720

720       730       740       750       760       770
ISF34    GTGACTGATCCAAGCCAAGTGAGCCATGGCACTGGCTTCACGTCCTTTGGCTTACTCAAA
         ::::::::::::::::::::::::::::::::::::::::::::::::::::::::::
HUMAN    GTGACTGATCCAAGCCAAGTGAGCCATGGCACTGGCTTCACGTCCTTTGGCTTACTCAAA
                730       740       750       760       770       780

780
ISF34    CTCTGA
         ::::::
HUMAN    CTCTGA
```

Figure 13(b): ISF34 Nucleotide Sequence Alignment With Murine CD154

```
96.6% identity in 783 nt overlap; score: 3672 E(10,000): 6.4e-298

10        20        30        40        50        60
ISF34   ATGATAGAAACATACAGCCAACCTTCCCCCAGATCCGTGGCAACTGGACTTCCAGCGAGC
        ::::::::::::::::::::::::::::::::::::::::::::::::::::::::::::
MURINE  ATGATAGAAACATACAGCCAACCTTCCCCCAGATCCGTGGCAACTGGACTTCCAGCGAGC
              10        20        30        40        50        60

70        80        90       100       110       120
ISF34   ATGAAGATTTTTATGTATTTACTTACTGTTTTCCTTATCACCCAAATGATTGGATCTGTG
        ::::::::::::::::::::::::::::::::::::::::::::::::::::::::::::
MURINE  ATGAAGATTTTTATGTATTTACTTACTGTTTTCCTTATCACCCAAATGATTGGATCTGTG
              70        80        90       100       110       120

130       140       150       160       170       180
ISF34   CTTTTTGCTGTGTATCTTCATAGAAGATTGGATAAGGTCGAAGAGGAAGTAAACCTTCAT
        ::::::::::::::::::::::::::::::::::::::::::::::::::::::::::::
MURINE  CTTTTTGCTGTGTATCTTCATAGAAGATTGGATAAGGTCGAAGAGGAAGTAAACCTTCAT
             130       140       150       160       170       180

190       200       210       220       230       240
ISF34   GAAGATTTTGTATTCATAAAAAAGCTAAAGAGATGCAACAAAGGAGAAGGATCTTTATCC
        ::::::::::::::::::::::::::::::::::::::::::::::::::::::::::::
MURINE  GAAGATTTTGTATTCATAAAAAAGCTAAAGAGATGCAACAAAGGAGAAGGATCTTTATCC
             190       200       210       220       230       240

250       260       270       280       290       300
ISF34   TTGCTGAACTGTGAGGAGATGAGAAGGCAATTTGAAGACCTTGTCAAGGATATAACGTTA
        ::::::::::::::::::::::::::::::::::::::::::::::::::::::::::::
MURINE  TTGCTGAACTGTGAGGAGATGAGAAGGCAATTTGAAGACCTTGTCAAGGATATAACGTTA
             250       260       270       280       290       300

310       320       330       340       350       360
ISF34   AACAAAGAAGAGAAAAAAGAAAACAGCTTTGAAATGCAAAGAGGTGATGAGGATCCTCAA
        ::::::::::::::::::::::::::::::::::::::::::::::::::::::::::::
MURINE  AACAAAGAAGAGAAAAAAGAAAACAGCTTTGAAATGCAAAGAGGTGATGAGGATCCTCAA
             310       320       330       340       350       360

370       380       390       400       410       420
ISF34   ATTGCAGCACACGTTGTAAGCGAAGCCAACAGTAATGCAGCATCCGTTCTACAGTGGGCC
        :::::::::::::::::::::::::::::::::::::::::::::::::::::::::::
MURINE  ATTGCAGCACACGTTGTAAGCGAAGCCAACAGTAATGCAGCATCCGTTCTACAGTGGGCC
             370       380       390       400       410       420

430       440       450       460       470       480
ISF34   AAGAAAGGATATTATACCATGAAAAGCAACTTGGTAACCCTGGAAAATGGGAAACAGCTG
        :::::::::::::::::::::::::::::::::: ::::::::::::::::::::::::
MURINE  AAGAAAGGATATTATACCATGAAAAGCAACTTGGTAATGCTTGAAAATGGGAAACAGCTG
             430       440       450       460       470       480

490       500       510       520       530       540
ISF34   ACGGTTAAAAGACAAGGACTCTATTATATCTATGCTCAAGTCACCTTCTGCTCTAATCGG
        ::::::::::: ::::::::::::::::: :::: ::::::::::::::::::::::::
MURINE  ACGGTTAAAAGAGAAGGACTCTATTATGTCTACACTCAAGTCACCTTCTGCTCTAATCGG
             490       500       510       520       530       540

550       560       570       580       590       600
ISF34   GAGGCTTCGAGTCAAGCCCCATTCATCGTCGGCCTCTGGCTGAAGCCCAGCAGTGGATCT
        ::: ::::::::::::: ::::::::::::::::::::::::::::::::: ::::::
MURINE  GAGCCTTCGAGTCAACGCCCATTCATCGTCGGCCTCTGGCTGAAGCCCAGCATTGGATCT
             550       560       570       580       590       600

610       620       630       640       650       660
ISF34   GAGAGAATCTTACTCAAGGCGGCAAATACCCACAGTTCCTCCCAGCTTTGCGAGCAGCAG
        ::::::::::::::::::::::::::::::::::::::::::::::::::::::::::::
MURINE  GAGAGAATCTTACTCAAGGCGGCAAATACCCACAGTTCCTCCCAGCTTTGCGAGCAGCAG
             610       620       630       640       650       660

670       680       690       700       710       720
ISF34   TCTATTCACTTGGGCGGAGTGTTTGAATTACAACCAGGTGCTTCGGTGTTTGTCAATGTG
        ::: :::::::::::::::::::::::::::: :::::::: ::::::::::: :: ::
MURINE  TCTGTTCACTTGGGCGGAGTGTTTGAATTACAAGCTGGTGCTTCTGTGTTTGTCAACGTG
             670       680       690       700       710       720

730       740       750       760       770       780
ISF34   ACTGATCCAAGCCAAGTGAGCCATGGCACTGGCTTCACGTCCTTTGGCTTACTCAAACTC
        ::::: ::::::::::::::: ::: :    :::::::: :: ::::::::::::::::
MURINE  ACTGAAGCAAGCCAAGTGATCCACAGAGTTGGCTTCTCATCTTTTGGCTTACTCAAACTC
             730       740       750       760       770       780

ISF34   TGA
        :::
MURINE  TGA
```

Figure 14(a): ISF36 Nucleotide Sequence Alignment With Human CD154

86.9% identity in 786 nt overlap; score: 2993 E(10,000): 2.7e-241

```
              10        20        30        40        50        60
ISF36   ATGATAGAAACATACAGCCAACCTTCCCCCAGATCCGTGGCAACTGGACTTCCAGCGAGC
        :::::  ::::::::::: :::::  ::::   :::  :  :::  ::::::::  ::        :::
HUMAN   ATGATCGAAACATACAACCAAACTTCTCCCCGATCTGCGGCCACTGGACTGCCCATCAGC
              10        20        30        40        50        60

70        80        90       100       110       120
ISF36   ATGAAGATTTTTATGTATTTACTTACTGTTTTCCTTATCACCCAAATGATTGGATCTGTG
        :::::  ::::::::::::::::::::::::  ::::::::::::: :::::::  :: :
HUMAN   ATGAAAATTTTTATGTATTTACTTACTGTTTTTCTTATCACCCAGATGATTGGGTCAGCA
              70        80        90       100       110       120

130       140       150       160       170       180
ISF36   CTTTTTGCTGTGTATCTTCATAGAAGATTGGATAAGGTCGAAGAGGAAGTAAACCTTCAT
        ::::::::::::::::::::::::::::  ::::: :::  ::::: :: :: :::::::
HUMAN   CTTTTTGCTGTGTATCTTCATAGAAGGTTGGACAAGATAGAAGATGAAAGGAATCTTCAT
             130       140       150       160       170       180

190       200       210       220       230       240
ISF36   GAAGATTTTGTATTCATAAAAAAGCTAAAGAGATGCAACAAAGGAGAAGGATCTTTATCC
        :::::::::::::::::: :   ::  :::::::::::::: :::::: :::: ::::::
HUMAN   GAAGATTTTGTATTCATGAAAACGATACAGAGATGCAACACAGGAGAAAGATCCTTATCC
             190       200       210       220       230       240

250       260       270       280       290       300
ISF36   TTGCTGAACTGTGAGGAGATGAGAAGGCAATTTGAAGACCTTGTCAAGGATATAACGTTA
        :: ::::::::::::::::::  : :  :: ::::::: :::::: :::::::::: :::
HUMAN   TTACTGAACTGTGAGGAGATTAAAAGCCAGTTTGAAGGCTTTGTGAAGGATATAATGTTA
             250       260       270       280       290       300

310       320       330       340       350
ISF36   AACAAAGAAGAGA---AAAAAGAAAACAGCTTTGAAATGCAAAGAGGTGATGAGGATCCT
        :::::::: ::::    : :::::::::::::::::::::::  :::::::: :::: ::
HUMAN   AACAAAGAGGAGACGAAGAAAGAAAACAGCTTTGAAATGCAAAAAGGTGATCAGAATCCT
             310       320       330       340       350       360

360       370       380       390       400       410
ISF36   CAAATTGCAGCACACGTTGTAAGCGAAGCCAACAGTAATGCAGCATCCGTTCTACAGTGG
        :::::::: :::::: :: :::::: ::::  :::::   ::  :::  :: ::::::::
HUMAN   CAAATTGCGGCACATGTCATAAGTGAGGCCAGCAGTAAAACAACATCTGTGTTACAGTGG
             370       380       390       400       410       420

420       430       440       450       460       470
ISF36   GCCAAGAAAGGATATTATACCATGAAAAGC AACTTGGTAACCCTGGAAAATGGGAAACAG
        ::  :  :::::::: :: ::::::    : ::::::::::::::::::::::::::::::
HUMAN   GCTGAAAAAGGATACTACACCATGAGCAAC AACTTGGTAACCCTGGAAAATGGGAAACAG
             430       440       450       460       470       480

480       490       500       510       520       530
ISF36   CTGACGGTTAAAAGACAAGGACTCTATTATATCTATGCTCAAGTCACCTTCTGCTCTAAT
        :::::  :::::::::::::::::::::::::::::::: :::::::::::: ::  :::
HUMAN   CTGACCGTTAAAAGACAAGGACTCTATTATATCTATGCCCAAGTCACCTTCTGTTCCAAT
             490       500       510       520       530       540

540       550       560       570       580       590
ISF36   CGGGAGGCTTCGAGTCAAGCCCCATTCATC GTCGGCCTCTGGCTGAAGCCCAGCAGTGGA
        ::::: ::::::::::::::::: :: : : :::::: ::::: :::::: :  :: ::
HUMAN   CGGGAAGCTTCGAGTCAAGCTCCATTTATA GCCAGCCTCTGCCTAAAGTCCCCCGGTAGA
             550       560       570       580       590       600

600       610       620       630       640       650
ISF36   TCTGAGAGAATCTTACTCAAG GCGGCAAATACCCACAGTTCCGCCAAGCCTTGCGGGCAG
        :  ::::::::::::::: :: :: ::::::::::::::::::::::: ::::::::::::
HUMAN   TTCGAGAGAATCTTACTCAGA GCTGCAAATACCCACAGTTCCGCCAAACCTTGCGGGCAA
             610       620       630       640       650       660

660       670       680       690       700       710
ISF36   CAGTCTATTCACTTGGGCGGAGTGTTTGAATTACAACCAGGTGCTTCGGTGTTTGTCAAT
        ::  ::  :::::::::::::::::::::::::: :::::::::::::::::::::::::
HUMAN   CAATCCATTCACTTGGGAGGAGTATTTGAATTGCAACCAGGTGCTTCGGTGTTTGTCAAT
             670       680       690       700       710       720

720       730       740       750       760       770
ISF36   GTGACTGATCCAAGCCAAGTGAGCCATGGCACTGGCTTCACGTCCTTTGGCTTACTCAAA
        ::::::::::::::::::::::::::::::::::::::::::::::::::::::::::::
HUMAN   GTGACTGATCCAAGCCAAGTGAGCCATGGCACTGGCTTCACGTCCTTTGGCTTACTCAAA
             730       740       750       760       770       780

780
ISF36   CTCTGA
        ::::::
HUMAN   CTCTGA
```

Figure 14(b): ISF36 Nucleotide Sequence Alignment With Murine CD154

96.0% identity in 783 nt overlap; score: 3636 E(10,000): 6.4e-295

```
                 10         20         30         40         50         60
ISF36   ATGATAGAAACATACAGCCAACCTTCCCCCAGATCCGTGGCAACTGGACTTCCAGCGAGC
        ::::::::::::::::::::::::::::::::::::::::::::::::::::::::::::
MURINE  ATGATAGAAACATACAGCCAACCTTCCCCCAGATCCGTGGCAACTGGACTTCCAGCGAGC
                 10         20         30         40         50         60

70         80         90        100        110        120
ISF36   ATGAAGATTTTTATGTATTTACTTACTGTTTTCCTTATCACCCAAATGATTGGATCTGTG
        ::::::::::::::::::::::::::::::::::::::::::::::::::::::::::::
MURINE  ATGAAGATTTTTATGTATTTACTTACTGTTTTCCTTATCACCCAAATGATTGGATCTGTG
                 70         80         90        100        110        120

130        140        150        160        170        180
ISF36   CTTTTTGCTGTGTATCTTCATAGAAGATTGGATAAGGTCGAAGAGGAAGTAAACCTTCAT
        ::::::::::::::::::::::::::::::::::::::::::::::::::::::::::::
MURINE  CTTTTTGCTGTGTATCTTCATAGAAGATTGGATAAGGTCGAAGAGGAAGTAAACCTTCAT
                130        140        150        160        170        180

190        200        210        220        230        240
ISF36   GAAGATTTTGTATTCATAAAAAAGCTAAAGAGATGCAACAAAGGAGAAGGATCTTTATCC
        ::::::::::::::::::::::::::::::::::::::::::::::::::::::::::::
MURINE  GAAGATTTTGTATTCATAAAAAAGCTAAAGAGATGCAACAAAGGAGAAGGATCTTTATCC
                190        200        210        220        230        240

250        260        270        280        290        300
ISF36   TTGCTGAACTGTGAGGAGATGAGAAGGCAATTTGAAGACCTTGTCAAGGATATAACGTTA
        ::::::::::::::::::::::::::::::::::::::::::::::::::::::::::::
MURINE  TTGCTGAACTGTGAGGAGATGAGAAGGCAATTTGAAGACCTTGTCAAGGATATAACGTTA
                250        260        270        280        290        300

310        320        330        340        350        360
ISF36   AACAAAGAAGAGAAAAAAGAAAACAGCTTTGAAATGCAAAGAGGTGATGAGGATCCTCAA
        ::::::::::::::::::::::::::::::::::::::::::::::::::::::::::::
MURINE  AACAAAGAAGAGAAAAAAGAAAACAGCTTTGAAATGCAAAGAGGTGATGAGGATCCTCAA
                310        320        330        340        350        360

370        380        390        400        410        420
ISF36   ATTGCAGCACACGTTGTAAGCGAAGCCAACAGTAATGCAGCATCCGTTCTACAGTGGGCC
        ::::::::::::::::::::::::::::::::::::::::::::::::::::::::::::
MURINE  ATTGCAGCACACGTTGTAAGCGAAGCCAACAGTAATGCAGCATCCGTTCTACAGTGGGCC
                370        380        390        400        410        420

430        440        450        460        470        480
ISF36   AAGAAAGGATATTATACCATGAAAAGCAACTTGGTAACCCTGGAAAATGGGAAACAGCTG
        :::::::::::::::::::::::::::::::::::: :: ::::::::::::::::::::
MURINE  AAGAAAGGATATTATACCATGAAAAGCAACTTGGTAATGCTTGAAAATGGGAAACAGCTG
                430        440        450        460        470        480

490        500        510        520        530        540
ISF36   ACGGTTAAAAGACAAGGACTCTATTATATCTATGCTCAAGTCACCTTCTGCTCTAATCGG
        ::::::::::::  ::::::::::::::::  ::::  ::::::::::::::::::::::
MURINE  ACGGTTAAAAGAGAAGGACTCTATTATGTCTACACTCAAGTCACCTTCTGCTCTAATCGG
                490        500        510        520        530        540

550        560        570        580        590        600
ISF36   GAGGCTTCGAGTCAAGCCCCATTCATCGTCGGCCTCTGGCTGAAGCCCAGCAGTGGATCT
        :::  ::::::::::: ::::::::::::::::::::::::::::::::::::  :::::
MURINE  GAGCCTTCGAGTCAACGCCCCATTCATCGTCGGCCTCTGGCTGAAGCCCAGCATTGGATCT
                550        560        570        580        590        600

610        620        630        640        650        660
ISF36   GAGAGAATCTTACTCAAGGCGGCAAATACCCACAGTTCCGCCAAGCCTTGCGGGCAGCAG
        :::::::::::::::::::::::::::::::::::::: ::: ::  ::::: :::::::
MURINE  GAGAGAATCTTACTCAAGGCGGCAAATACCCACAGTTCCTCCCAGCTTTGCGAGCAGCAG
                610        620        630        640        650        660

670        680        690        700        710        720
ISF36   TCTATTCACTTGGGCGGAGTGTTTGAATTACAACCAGGTGCTTCGGTGTTTGTCAATGTG
        ::: :::::::::::::::::::::::::::::: :::::::::::::::::::::::::
MURINE  TCTGTTCACTTGGGCGGAGTGTTTGAATTACAAGCTGGTGCTTCTGTGTTTGTCAACGTG
                670        680        690        700        710        720

730        740        750        760        770        780
ISF36   ACTGATCCAAGCCAAGTGAGCCATGGCACTGGCTTCACGTCCTTTGGCTTACTCAAACTC
        :::::  :::::::::::::  ::   :: :::::: ::: :: :::::::::::::::::
MURINE  ACTGAAGCAAGCCAAGTGATCCACAGAGTTGGCTTCTCATCTTTTGGCTTACTCAAACTC
                730        740        750        760        770        780

ISF36   TGA
        :::
MURINE  TGA
```

Figure 15(a): ISF38 Nucleotide Sequence Alignment With Human CD154

```
86.0% identity in 786 nt overlap; score: 2930 E(10,000): 4.8e-236
                 10        20        30        40        50        60
ISF38   ATGATAGAAACATACAGCCAACCTTCCCCCAGATCCGTGGCAACTGGACTTCCAGCGAGC
        :::::  :::::::::: :::: ::::  ::  ::::   ::: ::::::::::  ::   :::
HUMAN   ATGATCGAAACATACAACCAAACTTCTCCCCGATCTGCGGCCACTGGACTGCCCATCAGC
                 10        20        30        40        50        60

70        80        90       100       110       120
ISF38   ATGAAGATTTTTATGTATTTACTTACTGTTTTCCTTATCACCCAAATGATTGGATCTGTG
        ::::: ::::::::::::::::::::::::::: ::::::::::: :::::::: :: :
HUMAN   ATGAAAATTTTTATGTATTTACTTACTGTTTTTCTTATCACCCAGATGATTGGGTCAGCA
                 70        80        90       100       110       120

130       140       150       160       170       180
ISF38   CTTTTTGCTGTGTATCTTCATAGAAGATTGGATAAGGTCGAAGAGGAAGTAAACCTTCAT
        :::::::::::::::::::::::::::  :::::   :::::: :::  :: ::: :::::
HUMAN   CTTTTTGCTGTGTATCTTCATAGAAGGTTGGACAAGATAGAAGATGAAAAGGAATCTTCAT
                130       140       150       160       170       180

190       200       210       220       230       240
ISF38   GAAGATTTTGTATTCATAAAAAAGCTAAAGAGATGCAACAAAGGAGAAGGATCTTTATCC
        :::::::::::::::::::::: :::: : :: :::::::::::: ::::::::::::::: 
HUMAN   GAAGATTTTGTATTCATGAAAACGATACAGAGATGCAACACAGGAGAAAGATCCTTATCC
                190       200       210       220       230       240

250       260       270       280       290       300
ISF38   TTGCTGAACTGTGAGGAGATGAGAAGGCAATTTGAAGACCTTGTCAAGGATATAACGTTA
        ::  :::::::::::::::::: :  ::: :: :::::::: :: :::: ::::::::::  :::
HUMAN   TTACTGAACTGTGAGGAGATTAAAAGCCAGTTTGAAGGCTTTGTGAAGGATATAATGTTA
                250       260       270       280       290       300

310       320       330       340       350
ISF38   AACAAAGAAGAGA---AAAAAGAAAACAGCTTTGAAATGCAAAGAGGTGATGAGGATCCT
        :::::::::::::: ::::  :   ::::::::::::::::::::::::::::  ::::::  ::::: 
HUMAN   AACAAAGAGGAGACGAAGAAAGAAAACAGCTTTGAAATGCAAAAAGGTGATCAGAATCCT
                310       320       330       340       350       360

360       370       380       390       400       410
ISF38   CAAATTGCAGCACACGTTGTAAGCGAAGCCAACAGTAATGCAGCATCCGTTCTACAGTGG
        ::::::::: ::::::  ::::  ::::  :::: ::::::  :: :::: :  :::::::::
HUMAN   CAAATTGCGGCACATGTCATAAGTGAGGCCAGCAGTAAAACAACATCTGTGTTACAGTGG
                370       380       390       400       410       420

420       430       440       450       460       470
ISF38   GCCAAGAAAGGATATTATACCATGAAAAGC AACTTGGTAACCCTGGAAAATGGGAAACAG
        ::  : ::::::::: ::  :::::::  : :::::::::::::::::::::::::::::::::
HUMAN   GCTGAAAAAGGATACTACACCATGAGCAAC AACTTGGTAACCCTGGAAAATGGGAAACAG
                430       440       450       460       470       480

480       490       500       510       520       530
ISF38   CTGACGGTTAAAAGACAAGGACTCTATTATATCTATGCTCAAGTCACCTTCTGCTCTAAT
        :::::  :::::::::::::::::::::::::::::::::::::::: ::::::::::::::  :::
HUMAN   CTGACGGTTAAAAGACAAGGACTCTATTATATCTATGCCCAAGTCACCTTCTGTTCCAAT
                490       500       510       520       530       540

540       550       560       570       580       590
ISF38   CGGGAGCCTTCGAGTCAACGCCCATTCATCGTCGGCCTCTGGCTGAAGCCCAGCAGTGGA
        ::::: :::::::::::::::  ::::: :: : :  ::::::  :: :::::: :  :: ::
HUMAN   CGGGAAGCTTCGAGTCAAGCTCCATTTATAGCCAGCCTCTGCCTAAAGTCCCCCGGTAGA
                550       560       570       580       590       600

600       610       620       630       640       650
ISF38   TCTGAGAGAATCTTACTCAAGGCGGCAAATACCCACAGTTCCTCCCAGCTTTGCGAG CAG
        :  ::::::::::::::::  :: ::::::::::::::::::  :: :   ::::::   :::
HUMAN   TTCGAGAGAATCTTACTCAGAGCTGCAAATACCCACAGTTCCGCCAAACCTTGCGGG CAA
                610       620       630       640       650       660

660       670       680       690       700       710
ISF38   CAGTCTATTCACTTGGGCGGAGTGTTTGAATTACAACCAGGTGCTTCGGTGTTTGTCAAT
        :: :: ::::::::::::::  :::::::::::  ::::::::::::::::::::::::::::
HUMAN   CAATCCATTCACTTGGGAGGAGTATTTGAATTGCAACCAGGTGCTTCGGTGTTTGTCAAT
                670       680       690       700       710       720

720       730       740       750       760       770
ISF38   GTGACTGATCCAAGCCAAGTGAGCCATGGCACTGGCTTCACGTCCTTTGGCTTACTCAAA
        :::::::::::::::::::::::::::::::::::::::::::::::::::::::::::::::
HUMAN   GTGACTGATCCAAGCCAAGTGAGCCATGGCACTGGCTTCACGTCCTTTGGCTTACTCAAA
                730       740       750       760       770       780

780
ISF38   CTCTGA
        ::::::
HUMAN   CTCTGA
```

Figure 15(b): ISF38 Nucleotide Sequence Alignment With Murine CD154

```
96.9% identity in 783 nt overlap; score: 3699 E(10,000): 3.6e-300

10         20         30         40         50         60
ISF38   ATGATAGAAACATACAGCCAACCTTCCCCCAGATCCGTGGCAACTGGACTTCCAGCGAGC
        ::::::::::::::::::::::::::::::::::::::::::::::::::::::::::::
MURINE  ATGATAGAAACATACAGCCAACCTTCCCCCAGATCCGTGGCAACTGGACTTCCAGCGAGC
              10         20         30         40         50         60

70         80         90        100        110        120
ISF38   ATGAAGATTTTTATGTATTTACTTACTGTTTTCCTTATCACCCAAATGATTGGATCTGTG
        :::::::::::::::::::::::::::::::::::::::::::::::::::::::::::
MURINE  ATGAAGATTTTTATGTATTTACTTACTGTTTTCCTTATCACCCAAATGATTGGATCTGTG
              70         80         90        100        110        120

130        140        150        160        170        180
ISF38   CTTTTTGCTGTGTATCTTCATAGAAGATTGGATAAGGTCGAAGAGGAAGTAAACCTTCAT
        ::::::::::::::::::::::::::::::::::::::::::::::::::::::::::::
MURINE  CTTTTTGCTGTGTATCTTCATAGAAGATTGGATAAGGTCGAAGAGGAAGTAAACCTTCAT
             130        140        150        160        170        180

190        200        210        220        230        240
ISF38   GAAGATTTTGTATTCATAAAAAAGCTAAAGAGATGCAACAAAGGAGAAGGATCTTTATCC
        ::::::::::::::::::::::::::::::::::::::::::::::::::::::::::::
MURINE  GAAGATTTTGTATTCATAAAAAAGCTAAAGAGATGCAACAAAGGAGAAGGATCTTTATCC
             190        200        210        220        230        240

250        260        270        280        290        300
ISF38   TTGCTGAACTGTGAGGAGATGAGAAGGCAATTTGAAGACCTTGTCAAGGATATAACGTTA
        ::::::::::::::::::::::::::::::::::::::::::::::::::::::::::::
MURINE  TTGCTGAACTGTGAGGAGATGAGAAGGCAATTTGAAGACCTTGTCAAGGATATAACGTTA
             250        260        270        280        290        300

310        320        330        340        350        360
ISF38   AACAAAGAAGAGAAAAAAGAAAACAGCTTTGAAATGCAAAGAGGTGATGAGGATCCTCAA
        ::::::::::::::::::::::::::::::::::::::::::::::::::::::::::::
MURINE  AACAAAGAAGAGAAAAAAGAAAACAGCTTTGAAATGCAAAGAGGTGATGAGGATCCTCAA
             310        320        330        340        350        360

370        380        390        400        410        420
ISF38   ATTGCAGCACACGTTGTAAGCGAAGCCAACAGTAATGCAGCATCCGTTCTACAGTGGGCC
        ::::::::::::::::::::::::::::::::::::::::::::::::::::::::::::
MURINE  ATTGCAGCACACGTTGTAAGCGAAGCCAACAGTAATGCAGCATCCGTTCTACAGTGGGCC
             370        380        390        400        410        420

430        440        450        460        470        480
ISF38   AAGAAAGGATATTATACCATGAAAAGCAACTTGGTAACCCTGGAAAATGGGAAACAGCTG
        :::::::::::::::::::::::::::::::::::::: ::  :::::::::::::::::
MURINE  AAGAAAGGATATTATACCATGAAAAGCAACTTGGTAATGCTTGAAAATGGGAAACAGCTG
             430        440        450        460        470        480

490        500        510        520        530        540
ISF38   ACGGTTAAAAGACAAGGACTCTATTATATCTATGCTCAAGTCACCTTCTGCTCTAATCGG
        :::::::::::: ::::::::::::::::: ::::  :::::::::::::::::::::::
MURINE  ACGGTTAAAAGAGAAGGACTCTATTATGTCTACACTCAAGTCACCTTCTGCTCTAATCGG
             490        500        510        520        530        540

550        560        570        580        590        600
ISF38   GAGCCTTCGAGTCAACGCCCATTCATCGTCGGCCTCTGGCTGAAGCCCAGCAGTGGATCT
        :::::::::::::::::::::::::::::::::::::::::::::::::::: :::::::
MURINE  GAGCCTTCGAGTCAACGCCCATTCATCGTCGGCCTCTGGCTGAAGCCCAGCATTGGATCT
             550        560        570        580        590        600

610        620        630        640        650        660
ISF38   GAGAGAATCTTACTCAAGGCGGCAAATACCCACAGTTCCTCCCAGCTTTGCGAGCAGCAG
        ::::::::::::::::::::::::::::::::::::::::::::::::::::::::::::
MURINE  GAGAGAATCTTACTCAAGGCGGCAAATACCCACAGTTCCTCCCAGCTTTGCGAGCAGCAG
             610        620        630        640        650        660

670        680        690        700        710        720
ISF38   TCTATTCACTTGGGCGGAGTGTTTGAATTACAACCAGGTGCTTCGGTGTTTGTCAATGTG
        ::: :::::::::::::::::::::::::::::: :::::  ::::: :::::::: :::
MURINE  TCTGTTCACTTGGGCGGAGTGTTTGAATTACAAGCTGGTGCTTCTGTGTTTGTCAACGTG
             670        680        690        700        710        720

730        740        750        760        770        780
ISF38   ACTGATCCAAGCCAAGTGAGCCATGGCACTGGCTTCACGTCCTTTGGCTTACTCAAACTC
        ::::: :::::::::::::::::: ::::: :  ::::::: : :::: ::::::::::::
MURINE  ACTGAAGCAAGCCAAGTGATCCACAGAGTTGGCTTCTCATCTTTTGGCTTACTCAAACTC
             730        740        750        760        770        780

ISF38   TGA
        :::
MURINE  TGA
```

Fig. 16(a): ISF40 Nucleotide Sequence Alignment With Human CD154

```
86.5% identity in 786 nt overlap; score: 2566 E(10,000): 4.7e-239

10         20         30         40         50         60
ISF40   ATGATAGAAACATACAGCCAACCTTCCCCCAGATCCGTGGCAACTGGACTTCCAGCGAGC
        :::::  :::::::::  :::  ::: :::: : ::: ::::::: ::       :::
HUMAN   ATGATCGAAACATACAACCAAACTTCTCCCCGATCTGCGGCCACTGGACTGCCCATCAGC
               10         20         30         40         50         60

70         80         90        100        110        120
ISF40   ATGAAGATTTTTATGTATTTACTTACTGTTTTCCTTATCACCCAAATGATTGGATCTGTG
        :::::  :::::::::::::::::::::: :::::::::::::  ::::::::  ::  :
HUMAN   ATGAAAATTTTTATGTATTTACTTACTGTTTTTCTTATCACCCAGATGATTGGGTCAGCA
               70         80         90        100        110        120

130        140        150        160        170        180
ISF40   CTTTTTGCTGTGTATCTTCATAGAAGATTGGATAAGGTCGAAGAGGAAGTAAACCTTCAT
        ::::::::::::::::::::::::::  ::::: ::: : :::::  :::  :: ::::::
HUMAN   CTTTTTGCTGTGTATCTTCATAGAAGGTTGGACAAGATAGAAGATGAAAGGAATCTTCAT
              130        140        150        160        170        180

190        200        210        220        230        240
ISF40   GAAGATTTTGTATTCATAAAAAAAGCTAAAGAGATGCAACAAAGGAGAAGGATCTTTATCC
        ::::::::::::::::  ::::  :: ::::::::::::  ::::::::::  :::::::::::
HUMAN   GAAGATTTTGTATTCATGAAAACGATACAGAGATGCAACACAGGAGAAAGATCCTTATCC
              190        200        210        220        230        240

250        260        270        280        290        300
ISF40   TTGCTGAACTGTGAGGAGATGAGAAGGCAATTTGAAGACCTTGTCAAGGATATAACGTTA
        :: :::::::::::::::::  : ::: :: :::::::  : :::: :::::::::::::  ::::
HUMAN   TTACTGAACTGTGAGGAGATTAAAAGCCAGTTTGAAGGCTTTGTGAAGGATATAATGTTA
              250        260        270        280        290        300

310        320        330        340        350
ISF40   AACAAAGAAGAGA---AAAAAGAAAACAGCTTTGAAATGCAAAGAGGTGATGAGGATCCT
        :::::::  ::::     : ::::::::::::::::::::::::: :::::::: :: :::::
HUMAN   AACAAAGAGGAGACGAAGAAAGAAAACAGCTTTGAAATGCAAAAGGTGATCAGAATCCT
              310        320        330        340        350        360

360        370        380        390        400        410
ISF40   CAAATTGCAGCACACGTTGTAAGCGAAGCCAACAGTAATGCAGCATCCGTTCTACAGTGG
        ::::::::  ::::: ::  ::::: :: :::: ::::::  ::  :: ::  :::::::::
HUMAN   CAAATTGCGGCACATGTCATAAGTGAGGCCAGCAGTAAAACAACATCTGTGTTACAGTGG
              370        380        390        400        410        420

420        430        440        450        460        470
ISF40   GCCAAGAAAGGATATTATACCATGAAAAGC AACTTGGTAACCCTGGAAAATGGGAAACAG
        ::  : ::::::::: :: :::::::  :::  ::::::::::::::::::::::::::::::::
HUMAN   GCTGAAAAAGGATACTACACCATGAGCAAC AACTTGGTAACCCTGGAAAATGGGAAACAG
              430        440        450        460        470        480

480        490        500        510        520        530
ISF40   CTGACGGTTAAAAGACAAGGACTCTATTATATCTATGCTCAAGTCACCTTCTGCTCTAAT
        :::::  ::::::::::::::::::::::::::::::::  :::::::::::::  :::
HUMAN   CTGACCGTTAAAAGACAAGGACTCTATTATATCTATGCCCAAGTCACCTTCTGTTCCAAT
              490        500        510        520        530        540

540        550        560        570        580        590
ISF40   CGGGAGCCTTCGAGTCAACGCCCATTCATCGTCGGCCTCTGGCTGAAGCCCAGCAGTGGA
        :::::  :::::::::::  ::::: ::  : : ::::::::  ::: ::: ::  : :: ::
HUMAN   CGGGAAGCTTCGAGTCAAGCTCCATTTATAGCCAGCCTCTGCCTAAAGTCCCCCGGTAGA
              550        560        570        580        590        600

600        610        620        630        640        650
ISF40   TCTGAGAGAATCTTACTCAAG GCGGCAAATACCCACAGTTCCGCCAAGCCTTGCGGGCAG
        :  :::::::::::::::::   :: ::::::::::::::::::::::::  ::::::::::
HUMAN   TTCGAGAGAATCTTACTCAGA GCTGCAAATACCCACAGTTCCGCCAAACCTTGCGGGCAA
              610        620        630        640        650        660

660        670        680        690        700        710
ISF40   CAGTCTATTCACTTGGGCGGAGTGTTTGAATTACAACCAGGTGCTTCGGTGTTTGTCAAT
        :: :: ::::::::::::::  :::::::  ::::: :::::::::::::::::::::::::
HUMAN   CAATCCATTCACTTGGGAGGAGTATTTGAATTGCAACCAGGTGCTTCGGTGTTTGTCAAT
              670        680        690        700        710        720

720        730        740        750        760        770
ISF40   GTGACTGATCCAAGCCAAGTGAGCCATGGCACTGGCTTCACGTCCTTTGGCTTACTCAAA
        ::::::::::::::::::::::::::::::::::::::::::::::::::::::: :::::
HUMAN   GTGACTGATCCAAGCCAAGTGAGCCATGGCACTGGCTTCACGTCCTTTGGCTTACTCAAA
              730        740        750        760        770        780

780
ISF40   CTCTGA
        ::::::
HUMAN   CTCTGA
```

Fig. 16(b): ISF40 Nucleotide Sequence Alignment With Murine CD154

```
96.4% identity in 783 nt overlap; score: 3663 E(10,000): 3.6e-297

10        20        30        40        50        60
ISF40   ATGATAGAAACATACAGCCAACCTTCCCCCAGATCCGTGGCAACTGGACTTCCAGCGAGC
        ::::::::::::::::::::::::::::::::::::::::::::::::::::::::::::
MURINE  ATGATAGAAACATACAGCCAACCTTCCCCCAGATCCGTGGCAACTGGACTTCCAGCGAGC
              10        20        30        40        50        60

70        80        90       100       110       120
ISF40   ATGAAGATTTTTATGTATTTACTTACTGTTTTCCTTATCACCCAAATGATTGGATCTGTG
        ::::::::::::::::::::::::::::::::::::::::::::::::::::::::::::
MURINE  ATGAAGATTTTTATGTATTTACTTACTGTTTTCCTTATCACCCAAATGATTGGATCTGTG
              70        80        90       100       110       120

130       140       150       160       170       180
ISF40   CTTTTTGCTGTGTATCTTCATAGAAGATTGGATAAGGTCGAAGAGGAAGTAAACCTTCAT
        ::::::::::::::::::::::::::::::::::::::::::::::::::::::::::::
MURINE  CTTTTTGCTGTGTATCTTCATAGAAGATTGGATAAGGTCGAAGAGGAAGTAAACCTTCAT
             130       140       150       160       170       180

190       200       210       220       230       240
ISF40   GAAGATTTTGTATTCATAAAAAAGCTAAAGAGATGCAACAAAGGAGAAGGATCTTTATCC
        ::::::::::::::::::::::::::::::::::::::::::::::::::::::::::::
MURINE  GAAGATTTTGTATTCATAAAAAAGCTAAAGAGATGCAACAAAGGAGAAGGATCTTTATCC
             190       200       210       220       230       240

250       260       270       280       290       300
ISF40   TTGCTGAACTGTGAGGAGATGAGAAGGCAATTTGAAGACCTTGTCAAGGATATAACGTTA
        ::::::::::::::::::::::::::::::::::::::::::::::::::::::::::::
MURINE  TTGCTGAACTGTGAGGAGATGAGAAGGCAATTTGAAGACCTTGTCAAGGATATAACGTTA
             250       260       270       280       290       300

310       320       330       340       350       360
ISF40   AACAAAGAAGAGAAAAAAGAAAACAGCTTTGAAATGCAAAGAGGTGATGAGGATCCTCAA
        ::::::::::::::::::::::::::::::::::::::::::::::::::::::::::::
MURINE  AACAAAGAAGAGAAAAAAGAAAACAGCTTTGAAATGCAAAGAGGTGATGAGGATCCTCAA
             310       320       330       340       350       360

370       380       390       400       410       420
ISF40   ATTGCAGCACACGTTGTAAGCGAAGCCAACAGTAATGCAGCATCCGTTCTACAGTGGGCC
        ::::::::::::::::::::::::::::::::::::::::::::::::::::::::::::
MURINE  ATTGCAGCACACGTTGTAAGCGAAGCCAACAGTAATGCAGCATCCGTTCTACAGTGGGCC
             370       380       390       400       410       420

430       440       450       460       470       480
ISF40   AAGAAAGGATATTATACCATGAAAAGCAACTTGGTAACCCTGGAAAATGGGAAACAGCTG
        ::::::::::::::::::::::::::::::::::::::::::::: :: :::::::::::::
MURINE  AAGAAAGGATATTATACCATGAAAAGCAACTTGGTAATGCTTGAAAATGGGAAACAGCTG
             430       440       450       460       470       480

490       500       510       520       530       540
ISF40   ACGGTTAAAAGACAAGGACTCTATTATATCTATGCTCAAGTCACCTTCTGCTCTAATCGG
        :::::::::::  :::::::::::::::: ::::  ::::::::::::::::::::::::
MURINE  ACGGTTAAAAGAGAAGGACTCTATTATGTCTACACTCAAGTCACCTTCTGCTCTAATCGG
             490       500       510       520       530       540

550       560       570       580       590       600
ISF40   GAGCCTTCGAGTCAACGCCCATTCATCGTCGGCCTCTGGCTGAAGCCCAGCAGTGGATCT
        :::::::::::::::::::::::::::::::::::::::::::::::::::::  :::::
MURINE  GAGCCTTCGAGTCAACGCCCATTCATCGTCGGCCTCTGGCTGAAGCCCAGCATTGGATCT
             550       560       570       580       590       600

610       620       630       640       650       660
ISF40   GAGAGAATCTTACTCAAGGCGGCAAATACCCACAGTTCCGCCAAGCCTTGCGGGCAGCAG
        :::::::::::::::::::::::::::::::::::::  :: ::::: ::::: ::::::
MURINE  GAGAGAATCTTACTCAAGGCGGCAAATACCCACAGTTCCTCCCAGCTTTGCGAGCAGCAG
             610       620       630       640       650       660

670       680       690       700       710       720
ISF40   TCTATTCACTTGGGCGGAGTGTTTGAATTACAACCAGGTGCTTCGGTGTTTGTCAATGTG
        :::  :::::::::::::::::::::: : :::::::: ::::::::: :::::::::::
MURINE  TCTGTTCACTTGGGCGGAGTGTTTGAATTACAAGCTGGTGCTTCTGTGTTTGTCAACGTG
             670       680       690       700       710       720

730       740       750       760       770       780
ISF40   ACTGATCCAAGCCAAGTGAGCCATGGCACTGGCTTCACGTCCTTTGGCTTACTCAAACTC
        :::::  :::::::::::: :::  :  :: ::::: : :: :::::::::::::::::::
MURINE  ACTGAAGCAAGCCAAGTGATCCACAGAGTTGGCTTCTCATCTTTTGGCTTACTCAAACTC
             730       740       750       760       770       780

ISF40   TGA
        :::
MURINE  TGA
```

Figure 17(a): ISF31 Nucleotide Sequence Alignment With Human CD154
88.5% identity in 786 nt overlap; score: 3128 E(10,000): 1.4e-252

```
              10        20        30        40        50        60
ISF31   ATGATCGAAACATACAACCAAACTTCTCCCCGATCTGCGGCCACTGGACTGCCCATCAGC
        ::::::::::::::::::::: ::::::::::::::::::::::::::::::::::::::
HUMAN   ATGATCGAAACATACAACCAAACTTCTCCCCGATCTGCGGCCACTGGACTGCCCATCAGC
              10        20        30        40        50        60

70        80        90       100       110       120
ISF31   ATGAAAATTTTTATGTATTTACTTACTGTTTTTCTTATCACCCAGATGATTGGGTCAGCA
        ::::::::::::::::::::::::::::::::::::::::::::::::::::::::::::
HUMAN   ATGAAAATTTTTATGTATTTACTTACTGTTTTTCTTATCACCCAGATGATTGGGTCAGCA
              70        80        90       100       110       120

130       140       150       160       170       180
ISF31   CTTTTTGCTGTGTATCTTCATAGAAGGCTGGACAAGATAGAAGATGAAAGGAATCTTCAT
        :::::::::::::::::::::::::::: :::::::::::::::::::::::::::::::
HUMAN   CTTTTTGCTGTGTATCTTCATAGAAGGTTGGACAAGATAGAAGATGAAAGGAATCTTCAT
             130       140       150       160       170       180

190       200       210       220       230       240
ISF31   GAAGATTTTGTATTCATGAAAACGATACAGAGATGCAACACAGGAGAAAGATCCTTATCC
        ::::::::::::::::::::::::::::::::::::::::::::::::::::::::::::
HUMAN   GAAGATTTTGTATTCATGAAAACGATACAGAGATGCAACACAGGAGAAAGATCCTTATCC
             190       200       210       220       230       240

250       260       270       280       290       300
ISF31   TTACTGAACTGTGAGGAGATTAAAAGCCAGTTTGAAGGCTTTGTGAAGGATATAATGTTA
        ::::::::::::::::::::::::::::::::::::::::::::::::::::::::::::
HUMAN   TTACTGAACTGTGAGGAGATTAAAAGCCAGTTTGAAGGCTTTGTGAAGGATATAATGTTA
             250       260       270       280       290       300

310       320                                    330
ISF31   AACAAAGAGGAGACGAAGAAA-----------------------GATGAGGATCCT
        :::::::::::::::::::::                      ::: :: :::::::
HUMAN   AACAAAGAGGAGACGAAGAAAGAAAACAGCTTTGAAATGCAAAAAGGTGATCAGAATCCT
             310       320       330       340       350       360

340       350       360       370       380       390
ISF31   CAAATTGCAGCACACGTTGTAAGCGAAGCCAACAGTAATGCAGCATCCGTTCTACAGTGG
        ::::::::  ::::  ::::  ::::  :::: ::::: ::::  ::  :  :::::::
HUMAN   CAAATTGCGGCACATGTCATAAGTGAGGCCAGCAGTAAAACAACATCTGTGTTACAGTGG
             370       380       390       400       410       420

400       410       420       430       440       450
ISF31   GCCAAGAAAGGATATTATACCATGAAAAGC AACTTGGTAACCCTGGAAAATGGGAAACAG
        ::  : ::::::::  :: :::::::     ::::::::::::::::::::::::::::
HUMAN   GCTGAAAAAGGATACTACACCATGAGCAAC AACTTGGTAACCCTGGAAAATGGGAAACAG
             430       440       450       460       470       480

460       470       480       490       500       510
ISF31   CTGACGGTTAAAAGACAAGGACTCTATTATATCTATGCTCAAGTCACCTTCTGCTCTAAT
        ::::: ::::::::::::::::::::::::::::::::: ::::::::::::  : :::
HUMAN   CTGACCGTTAAAAGACAAGGACTCTATTATATCTATGCCCAAGTCACCTTCTGTTCCAAT
             490       500       510       520       530       540

520       530       540       550       560       570
ISF31   CGGGAGCCTTCGAGTCAACGCCCATTCATCGTCGGCCTCTGGCTGAAGCCCAGCAGTGGA
        ::::: :::::::::::: ::::: :: : ::::::: :: ::: ::  : :: :: ::
HUMAN   CGGGAAGCTTCGAGTCAAGCTCCATTTATAGCCAGCCTCTGCCTAAAGTCCCCCGGTAGA
             550       560       570       580       590       600

580       590       600       610       620       630
ISF31   TCTGAGAGAATCTTACTCAAGGCGGCAAATACCCACAGTTCCTCCCAGCTTTGCGAGCAG
        : :::::::::::::::::: ::::::::::::::::::: :: : : :: : ::: :::
HUMAN   TTCGAGAGAATCTTACTCAGAGCTGCAAATACCCACAGTTCCGCCAAACCTTGCGGGCAA
             610       620       630       640       650       660

640       650       660       670       680       690
ISF31   CAGTCTGTT CACTTGGGCGGAGTGTTTGAATTACAACCAGGTGCTTCGGTGTTTGTCAAT
        ::  ::    :::::::: ::::: ::::::: ::::::::::::::::::::::::::
HUMAN   CAATCCATT CACTTGGGAGGAGTATTTGAATTGCAACCAGGTGCTTCGGTGTTTGTCAAT
             670       680       690       700       710       720

700       710       720       730       740       750
ISF31   GTGACTGATCCAAGCCAAGTGAGCCATGGCACTGGCTTCACGTCCTTTGGCTTACTCAAA
        ::::::::::::::::::::::::::::::::::::::::::::::::::::::::::::
HUMAN   GTGACTGATCCAAGCCAAGTGAGCCATGGCACTGGCTTCACGTCCTTTGGCTTACTCAAA
             730       740       750       760       770       780

ISF31   CTCTGA
        ::::::
HUMAN   CTCTGA
```

Figure 17(b): ISF31 Nucleotide Sequence Alignment With Murine CD154

```
87.7% identity in 783 nt overlap; score: 3031 E(10,000): 1.7e-244

10         20         30         40         50         60
ISF31   ATGATCGAAACATACAACCAAACTTCTCCCCGATCTGCGGCCACTGGACTGCCCATCAGC
        :::::  :::::::::::: ::::  :::  :::  :  ::: :::::::::::  :::
MURINE  ATGATAGAAACATACAGCCAACCTTCCCCCAGATCCGTGGCAACTGGACTTCCAGCGAGC
                10         20         30         40         50         60

70         80         90        100        110        120
ISF31   ATGAAAATTTTTATGTATTTACTTACTGTTTTTCTTATCACCCAGATGATTGGGTCAGCA
        :::::  :::::::::::::::::::::::::  ::::::::::: :::::::: ::  :
MURINE  ATGAAGATTTTTATGTATTTACTTACTGTTTTCCTTATCACCCAAATGATTGGATCTGTG
                70         80         90        100        110        120

130        140        150        160        170        180
ISF31   CTTTTTGCTGTGTATCTTCATAGAAGGCTGGACAAGATAGAAGATGAAAGGAATCTTCAT
        :::::::::::::::::::::::::::  ::::  ::  ::::::  ::  :::::::::
MURINE  CTTTTTGCTGTGTATCTTCATAGAAGATTGGATAAGGTCGAAGAGGAAGTAAACCTTCAT
               130        140        150        160        170        180

190        200        210        220        230        240
ISF31   GAAGATTTTGTATTCATGAAAACGATACAGAGATGCAACACAGGAGAAAGATCCTTATCC
        :::::::::::::::::::::  ::  :  :::::::::::  ::::::::: :::::::
MURINE  GAAGATTTTGTATTCATAAAAAAGCTAAAGAGATGCAACAAAGGAGAAGGATCTTTATCC
               190        200        210        220        230        240

250        260        270        280        290        300
ISF31   TTACTGAACTGTGAGGAGATTAAAAGCCAGTTTGAAGGCTTTGTGAAGGATATAATGTTA
        ::  :::::::::::::::::  :::  :::::::: :  :: :::::::::::  ::::
MURINE  TTGCTGAACTGTGAGGAGATGAGAAGGCAATTTGAAGACCTTGTCAAGGATATAACGTTA
               250        260        270        280        290        300

310        320                                    330
ISF31   AACAAAGAGGAGACGAA-GAAA---------------------GATGAGGATCCTCAA
        ::::::::: ::::  :: ::::                     :::::::::::::::
MURINE  AACAAAGAAGAGAAAAAGAAAACAGCTTTGAAATGCAAAGAGGTGATGAGGATCCTCAA
               310        320        330        340        350        360

340        350        360        370        380        390
ISF31   ATTGCAGCACACGTTGTAAGCGAAGCCAACAGTAATGCAGCATCCGTTCTACAGTGGGCC
        :::::::::::::::::::::::::::::::::::::::::::::::::::::::::::
MURINE  ATTGCAGCACACGTTGTAAGCGAAGCCAACAGTAATGCAGCATCCGTTCTACAGTGGGCC
               370        380        390        400        410        420

400        410        420        430        440        450
ISF31   AAGAAAGGATATTATACCATGAAAAGCAACTTGGTAACCCTGGAAAATGGGAAACAGCTG
        ::::::::::::::::::::::::::::::::::::  :: :::::::::::::::::
MURINE  AAGAAAGGATATTATACCATGAAAAGCAACTTGGTAATGCTTGAAAATGGGAAACAGCTG
               430        440        450        460        470        480

460        470        480        490        500        510
ISF31   ACGGTTAAAAGACAAGGACTCTATTATATCTATGCTCAAGTCACCTTCTGCTCTAATCGG
        ::::::::::::  :::::::::::::: :::::: ::::::::::::::::::::::
MURINE  ACGGTTAAAAGAGAAGGACTCTATTATGTCTACACTCAAGTCACCTTCTGCTCTAATCGG
               490        500        510        520        530        540

520        530        540        550        560        570
ISF31   GAGCCTTCGAGTCAACGCCCATTCATCGTCGGCCTCTGGCTGAAGCCCAGCAGTGGATCT
        ::::::::::::::::::::::::::::::::::::::::::::::::::::: ::::
MURINE  GAGCCTTCGAGTCAACGCCCATTCATCGTCGGCCTCTGGCTGAAGCCCAGCATTGGATCT
               550        560        570        580        590        600

580        590        600        610        620        630
ISF31   GAGAGAATCTTACTCAAGGCGGCAAATACCCACAGTTCCTCCCAGCTTTGCGAGCAGCAG
        ::::::::::::::::::::::::::::::::::::::::::::::::::::::::::
MURINE  GAGAGAATCTTACTCAAGGCGGCAAATACCCACAGTTCCTCCCAGCTTTGCGAGCAGCAG
               610        620        630        640        650        660

640        650        660        670        680        690
ISF31   TCTGTTCACTTGGGCGGAGTGTTTGAATTACAACCAGGTGCTTCGGTGTTTGTCAATGTG
        ::::::::::::::::::::::::::::::::  ::::::: :::::::::::::  :::
MURINE  TCTGTTCACTTGGGCGGAGTGTTTGAATTACAAGCTGGTGCTTCTGTGTTTGTCAACGTG
               670        680        690        700        710        720

700        710        720        730        740        750
ISF31   ACTGATCCAAGCCAAGTGAGCCATGGCACTGGCTTCACGTCCTTTGGCTTACTCAAACTC
        :::::  :::::::::::::  :::   :  ::::::::  : :::::::::::::::::
MURINE  ACTGAAGCAAGCCAAGTGATCCACAGAGTTGGCTTCTCATCTTTTGGCTTACTCAAACTC
               730        740        750        760        770        780

ISF31   TGA
        :::
MURINE  TGA
```

Figure 18(a): ISF33 Nucleotide Sequence Alignment With Human CD154

```
89.2% identity in 786 nt overlap; score: 3155 E(10,000): 8e-255

10        20        30        40        50        60
ISF33   ATGATCGAAACATACAACCAAACTTCTCCCCGATCTGCGGCCACTGGACTGCCCATCAGC
        ::::::::::::::::::::::::::::::::::::::::::::::::::::::::::::
HUMAN   ATGATCGAAACATACAACCAAACTTCTCCCCGATCTGCGGCCACTGGACTGCCCATCAGC
              10        20        30        40        50        60

70        80        90       100       110       120
ISF33   ATGAAAATTTTTATGTATTTACTTACTGTTTTTCTTATCACCCAGATGATTGGGTCAGCA
        ::::::::::::::::::::::::::::::::::::::::::::::::::::::::::::
HUMAN   ATGAAAATTTTTATGTATTTACTTACTGTTTTTCTTATCACCCAGATGATTGGGTCAGCA
              70        80        90       100       110       120

130       140       150       160       170       180
ISF33   CTTTTTGCTGTGTATCTTCATAGAAGGCTGGACAAGATAGAAGATGAAAGGAATCTTCAT
        ::::::::::::::::::::::::::::: ::::::::::::::::::::::::::::::
HUMAN   CTTTTTGCTGTGTATCTTCATAGAAGGTTGGACAAGATAGAAGATGAAAGGAATCTTCAT
             130       140       150       160       170       180

190       200       210       220       230       240
ISF33   GAAGATTTTGTATTCATGAAAACGATACAGAGATGCAACACAGGAGAAAGATCCTTATCC
        ::::::::::::::::::::::::::::::::::::::::::::::::::::::::::::
HUMAN   GAAGATTTTGTATTCATGAAAACGATACAGAGATGCAACACAGGAGAAAGATCCTTATCC
             190       200       210       220       230       240

250       260       270       280       290       300
ISF33   TTACTGAACTGTGAGGAGATTAAAAGCCAGTTTGAAGGCTTTGTGAAGGATATAATGTTA
        ::::::::::::::::::::::::::::::::::::::::::::::::::::::::::::
HUMAN   TTACTGAACTGTGAGGAGATTAAAAGCCAGTTTGAAGGCTTTGTGAAGGATATAATGTTA
             250       260       270       280       290       300

310       320                                    330
ISF33   AACAAAGAGGAGACGAAGAAA--------------------------GATGAGGATCCT
        :::::::::::::::::::::                          ::: :: :::::
HUMAN   AACAAAGAGGAGACGAAGAAAGAAAACAGCTTTGAAATGCAAAAAGGTGATCAGAATCCT
             310       320       330       340       350       360

340       350       360       370       380       390
ISF33   CAAATTGCAGCACACGTTGTAAGCGAAGCCAACAGTAATGCAGCATCCGTTCTACAGTGG
        :::::: ::::: ::: :: :: :::::: :::::: :: ::::: :: :::::::
HUMAN   CAAATTGCGGCACATGTCATAAGTGAGGCCAGCAGTAAAACAACATCTGTGTTACAGTGG
             370       380       390       400       410       420

400       410       420       430       440       450
ISF33   GCCAAGAAAGGATATTATACCATGAAAAGCAACTTGGTAACCCTGGAAAATGGGAAACAG
        ::  :  ::::::::: ::::::::::  :: ::::::::::::::::::::::::::::
HUMAN   GCTGAAAAAGGATACTACACCATGAGCAACAACTTGGTAACCCTGGAAAATGGGAAACAG
             430       440       450       460       470       480

460       470       480       490       500       510
ISF33   CTGACGGTTAAAAGACAAGGACTCTATTATATCTATGCTCAAGTCACCTTCTGCTCTAAT
        ::::: ::::::::::::::::::::::::::::::::: :::::::::::::: :: ::
HUMAN   CTGACCGTTAAAAGACAAGGACTCTATTATATCTATGCCCAAGTCACCTTCTGTTCCAAT
             490       500       510       520       530       540

520       530       540       550       560       570
ISF33   CGGGAGGCTTCGAGTCAAGCCCCATTCATCGTCGGCCTCTGGCTGAAGCCCAGCAGTGGA
        ::::: :::::::::::::: :: ::::: ::  :: :::::::: :: ::::   :: ::
HUMAN   CGGGAAGCTTCGAGTCAAGCTCCATTTATAGCCAGCCTCTGCCTAAAGTCCCCCGGTAGA
             550       560       570       580       590       600

580       590       600       610       620       630
ISF33   TCTGAGAGAATCTTACTCAAGGCGGCAAATACCCACAGTTCCTCCCAGCTTTGCGAGCAG
        :  ::::::::::::::::: :: :::::::::::::::::: :: :: :: ::::: :::
HUMAN   TTCGAGAGAATCTTACTCAGAGCTGCAAATACCCACAGTTCCGCCAAAACCTTGCGGGCAA
             610       620       630       640       650       660

640       650       660       670       680       690
ISF33   CAGTCTGTTCACTTGGGCGGAGTGTTTGAATTACAACCAGGTGCTTCGGTGTTTGTCAAT
        ::  :: :::::::::: :: ::: ::::::: ::::::::::::::::::: ::::::
HUMAN   CAATCCATTCACTTGGGAGGAGTATTTGAATTGCAACCAGGTGCTTCGGTGTTTGTCAAT
             670       680       690       700       710       720

700       710       720       730       740       750
ISF33   GTGACTGATCCAAGCCAAGTGAGCCATGGCACTGGCTTCACGTCCTTTGGCTTACTCAAA
        ::::::::::::::::::::::::::::::::::::::::::::::::::::::::::::
HUMAN   GTGACTGATCCAAGCCAAGTGAGCCATGGCACTGGCTTCACGTCCTTTGGCTTACTCAAA
             730       740       750       760       770       780

ISF33   CTCTGA
        ::::::
HUMAN   CTCTGA
```

Figure 18(b): ISF33 Nucleotide Sequence Alignment With Murine CD154

```
87.4% identity in 783 nt overlap; score: 3004 E(10,000): 3.1e-242

10        20        30        40        50        60
ISF33  ATGATCGAAACATACAACCAAACTTCTCCCCGATCTGCGGCCACTGGACTGCCCCATCAGC
       :::::  :::::::::::  ::::  :::  ::::  :  :::  ::::::::::  :::
MURINE ATGATAGAAACATACAGCCAACCTTCCCCCAGATCCGTGGCAACTGGACTTCCAGCGAGC
              10        20        30        40        50        60

70        80        90       100       110       120
ISF33  ATGAAAATTTTTATGTATTTACTTACTGTTTTTCTTATCACCCAGATGATTGGGTCAGCA
       :::::  :::::::::: ::::  ::::::::::::::::::::::::  ::::  :: :
MURINE ATGAAGATTTTTATGTATTTACTTACTGTTTTCCTTATCACCCAAATGATTGGATCTGTG
              70        80        90       100       110       120

130       140       150       160       170       180
ISF33  CTTTTTGCTGTGTATCTTCATAGAAGGCTGGACAAGATAGAAGATGAAAGGAATCTTCAT
       ::::::::::::::: :::::::::   ::  :  :  ::::::  :::  *:: :::::
MURINE CTTTTTGCTGTGTATCTTCATAGAAGATTGGATAAGGTCGAAGAGGAAGTAAACCTTCAT
             130       140       150       160       170       180

190       200       210       220       230       240
ISF33  GAAGATTTTGTATTCATGAAAACGATACAGAGATGCAACACAGGAGAAAGATCCTTATCC
       :::::::::::::::::  :::  :  ::::::::::::: :::::::::::: :::::
MURINE GAAGATTTTGTATTCATAAAAAAGCTAAAGAGATGCAACAAAGGAGAAGGATCTTTATCC
             190       200       210       220       230       240

250       260       270       280       290       300
ISF33  TTACTGAACTGTGAGGAGATTAAAAGCCAGTTTGAAGGCTTTGTGAAGGATATAATGTTA
       :: ::::::::::::::::  :   :: :::::::  ::::  ::::::::::::  :::
MURINE TTGCTGAACTGTGAGGAGATGAGAAGGCAATTTGAAGACCTTGTCAAGGATATAACGTTA
             250       260       270       280       290       300

310       320                                     330
ISF33  AACAAAGAGGAGACGAA-GAAA--------------------GATGAGGATCCTCAA
       :::::::  ::: : :: ::::                    ::::::::::::::::
MURINE AACAAAGAAGAGAAAAAAGAAAACAGCTTTGAAATGCAAAGAGGTGATGAGGATCCTCAA
             310       320       330       340       350       360

340       350       360       370       380       390
ISF33  ATTGCAGCACACGTTGTAAGCGAAGCCAACAGTAATGCAGCATCCGTTCTACAGTGGGCC
       ::::::::::::::::::::::::::::::::::::::::::::::::::::::::::::
MURINE ATTGCAGCACACGTTGTAAGCGAAGCCAACAGTAATGCAGCATCCGTTCTACAGTGGGCC
             370       380       390       400       410       420

400       410       420       430       440       450
ISF33  AAGAAAGGATATTATACCATGAAAAGCAACTTGGTAACCCTGGAAAATGGGAAACAGCTG
       :::::::::::::::::::::::::::::::::::: :: ::::::::::::::::::::
MURINE AAGAAAGGATATTATACCATGAAAAGCAACTTGGTAATGCTTGAAAATGGGAAACAGCTG
             430       440       450       460       470       480

460       470       480       490       500       510
ISF33  ACGGTTAAAAGACAAGGACTCTATTATATCTATGCTCAAGTCACCTTCTGCTCTAATCGG
       ::::::::::::::  ::::::::::::: ::::  ::::::::::::::::::::::::
MURINE ACGGTTAAAAGAGAAGGACTCTATTATGTCTACACTCAAGTCACCTTCTGCTCTAATCGG
             490       500       510       520       530       540

520       530       540       550       560       570
ISF33  GAGGCTTCGAGTCAAGCCCCATTCATCGTCGGCCTCTGGCTGAAGCCCAGCAGTGGATCT
       ::: ::::::::::::: ::::::::::::::::::::::::::::::::::: :::::::
MURINE GAGCCTTCGAGTCAACGCCCATTCATCGTCGGCCTCTGGCTGAAGCCCAGCATTGGATCT
             550       560       570       580       590       600

580       590       600       610       620       630
ISF33  GAGAGAATCTTACTCAAGGCGGCAAATACCCACAGTTCCTCCCAGCTTTGCGAGCAGCAG
       ::::::::::::::::::::::::::::::::::::::::::::::::::::::::::::
MURINE GAGAGAATCTTACTCAAGGCGGCAAATACCCACAGTTCCTCCCAGCTTTGCGAGCAGCAG
             610       620       630       640       650       660

640       650       660       670       680       690
ISF33  TCTGTTCACTTGGGCGGAGTGTTTGAATTACAACCAGGTGCTTCGGTGTTTGTCAATGTG
       :::::::::::::::::::::::::::::::::::: :::::::: ::::::: ::::::
MURINE TCTGTTCACTTGGGCGGAGTGTTTGAATTACAAGCTGGTGCTTCTGTGTTTGTCAACGTG
             670       680       690       700       710       720

700       710       720       730       740       750
ISF33  ACTGATCCAAGCCAAGTGAGCCATGGCACTGGCTTCACGTCCTTTGGCTTACTCAAACTC
       ::::: :::::::::::::::  ::::::  :::::::: :: :::::::::::::::::
MURINE ACTGAAGCAAGCCAAGTGATCCACAGAGTTGGCTTCTCATCTTTTGGCTTACTCAAACTC
             730       740       750       760       770       780

ISF33  TGA
       :::
MURINE TGA
```

Figure 19(a): ISF35 Nucleotide Sequence Alignment With Human CD154

89.3% identity in 786 nt overlap; score: 3164 E(10,000): 1.4e-255

```
              10         20         30         40         50         60
ISF35  ATGATCGAAACATACAACCAAACTTCTCCCCGATCTGCGGCCACTGGACTGCCCATCAGC
       ::::::::::::::::::::::::::::::::::::::::::::::::::::::::::::
HUMAN  ATGATCGAAACATACAACCAAACTTCTCCCCGATCTGCGGCCACTGGACTGCCCATCAGC
              10         20         30         40         50         60

70         80         90        100        110        120
ISF35  ATGAAAATTTTTATGTATTTACTTACTGTTTTTCTTATCACCCAGATGATTGGGTCAGCA
       ::::::::::::::::::::::::::::::::::::::::::::::::::::::::::::
HUMAN  ATGAAAATTTTTATGTATTTACTTACTGTTTTTCTTATCACCCAGATGATTGGGTCAGCA
              70         80         90        100        110        120

130        140        150        160        170        180
ISF35  CTTTTTGCTGTGTATCTTCATAGAAGGCTGGACAAGATAGAAGATGAAAGGAATCTTCAT
       ::::::::::::::::::::::::::::::::::::::::::::::::::::::::::::
HUMAN  CTTTTTGCTGTGTATCTTCATAGAAGGTTGGACAAGATAGAAGATGAAAGGAATCTTCAT
             130        140        150        160        170        180

190        200        210        220        230        240
ISF35  GAAGATTTTGTATTCATGAAAACGATACAGAGATGCAACACAGGAGAAAGATCCTTATCC
       ::::::::::::::::::::::::::::::::::::::::::::::::::::::::::::
HUMAN  GAAGATTTTGTATTCATGAAAACGATACAGAGATGCAACACAGGAGAAAGATCCTTATCC
             190        200        210        220        230        240

250        260        270        280        290        300
ISF35  TTACTGAACTGTGAGGAGATTAAAAGCCAGTTTGAAGGCTTTGTGAAGGATATAATGTTA
       ::::::::::::::::::::::::::::::::::::::::::::::::::::::::::::
HUMAN  TTACTGAACTGTGAGGAGATTAAAAGCCAGTTTGAAGGCTTTGTGAAGGATATAATGTTA
             250        260        270        280        290        300

310        320                                      330
ISF35  AACAAAGAGGAGACGAAGAAA-------------------------GATGAGGATCCT
       :::::::::::::::::::::                        ::: :: :::::
HUMAN  AACAAAGAGGAGACGAAGAAAGAAAACAGCTTTGAAATGCAAAAAGGTGATCAGAATCCT
             310        320        330        340        350        360

340        350        360        370        380        390
ISF35  CAAATTGCAGCACACGTTGTAAGCGAAGCCAACAGTAATGCAGCATCCGTTCTACAGTGG
       :::::::: ::::: :: :::: :: :::: ::::::: :: :::: :: ::::::: 
HUMAN  CAAATTGCGGCACATGTCATAAGTGAGGCCAGCAGTAAAACAACATCTGTGTTACAGTGG
             370        380        390        400        410        420

400        410        420        430        440        450
ISF35  GCCAAGAAAGGATATTATACCATGAAAAGC AACTTGGTAACCCTGGAAAATGGGAAACAG
       ::  : :::::::: :: ::::::: :    ::::::::::::::::::::::::::::
HUMAN  GCTGAAAAAGGATACTACACCATGAGCAAC AACTTGGTAACCCTGGAAAATGGGAAACAG
             430        440        450        460        470        480

460        470        480        490        500        510
ISF35  CTGACGGTTAAAAGACAAGGACTCTATTATATCTATGCTCAAGTCACCTTCTGCTCTAAT
       :::::  :::::::::::::::::::::::::::::::  :::::::::::::  :::
HUMAN  CTGACCGTTAAAAGACAAGGACTCTATTATATCTATGCCCAAGTCACCTTCTGTTCCAAT
             490        500        510        520        530        540

520        530        540        550        560        570
ISF35  CGGGAGGCTTCGAGTCAAGCCCCATTCATC GTCGGCCTCTGGCTGAAGCCCAGCAGTGGA
       ::::  ::::::::::::::  :::::::  :  ::::::::::  :::: ::::::::
HUMAN  CGGGAAGCTTCGAGTCAAGCTCCATTTATA GCCAGCCTCTGCCTAAAGTCCCCCGGTAGA
             550        560        570        580        590        600

580        590        600        610        620        630
ISF35  TCTGAGAGAATCTTACTCAAGGCGGCAAATACCCACAGTTCCTCCCAGCTTTGCGAG CAG
       :  :::::::::::::::::::  ::::::::::::::::  : : :::::: :::  ::
HUMAN  TTCGAGAGAATCTTACTCAGAGCTGCAAATACCCACAGTTCCGCCAAACCTTGCGGG CAA
             610        620        630        640        650        660

640        650        660        670        680        690
ISF35  CAGTCTATTCACTTGGGCGGAGTGTTTGAATTACAACCAGGTGCTTCGGTGTTTGTCAAT
       ::  :: :::::::::::  ::::: ::::::: :::::::::::::::::::::::::
HUMAN  CAATCCATTCACTTGGGAGGAGTATTTGAATTGCAACCAGGTGCTTCGGTGTTTGTCAAT
             670        680        690        700        710        720

700        710        720        730        740        750
ISF35  GTGACTGATCCAAGCCAAGTGAGCCATGGCACTGGCTTCACGTCCTTTGGCTTACTCAAA
       :::::::::::::::::::::::::::::::::::::::::::::::::::::::: :::
HUMAN  GTGACTGATCCAAGCCAAGTGAGCCATGGCACTGGCTTCACGTCCTTTGGCTTACTCAAA
             730        740        750        760        770        780

ISF35  CTCTGA
       ::::::
HUMAN  CTCTGA
```

Figure 19(b): ISF35 Nucleotide Sequence Alignment With Murine CD154

```
87.2% identity in 783 nt overlap; score: 2995 E(10,000): 1.7e-241
              10        20        30        40        50        60
ISF35  ATGATCGAAACATACAACCAAACTTCTCCCCGATCTGCGGCCACTGGACTGCCCATCAGC
       ::::: :::::::::: :::: :::: :::: : ::: :::::::: ::     :::
MURINE ATGATAGAAACATACAGCCAACCTTCCCCCAGATCCGTGGCAACTGGACTTCCAGCGAGC
              10        20        30        40        50        60

70        80        90       100       110       120
ISF35  ATGAAAATTTTTATGTATTTACTTACTGTTTTTCTTATCACCCAGATGATTGGGTCAGCA
       ::::: :::::::::::::::::::::::::::: :::::::::  :::::::: :  :
MURINE ATGAAGATTTTTATGTATTTACTTACTGTTTTCCTTATCACCCAAATGATTGGATCTGTG
              70        80        90       100       110       120

130       140       150       160       170       180
ISF35  CTTTTTGCTGTGTATCTTCATAGAAGGCTGGACAAGATAGAAGATGAAAGGAATCTTCAT
       ::::::::::::::::::::::::::: ::::  : ::::: :::    :: :::::::
MURINE CTTTTTGCTGTGTATCTTCATAGAAGATTGGATAAGGTCGAAGAGGAAGTAAACCTTCAT
             130       140       150       160       170       180

190       200       210       220       230       240
ISF35  GAAGATTTTGTATTCATGAAAACGATACAGAGATGCAACACAGGAGAAAGATCCTTATCC
       ::::::::::::::: ::: : :: :::::::::::::: ::::::: :::: :::::::
MURINE GAAGATTTTGTATTCATAAAAAAGCTAAAGAGATGCAACAAAGGAGAAGGATCTTTATCC
             190       200       210       220       230       240

250       260       270       280       290       300
ISF35  TTACTGAACTGTGAGGAGATTAAAAGCCAGTTTGAAGGCTTTGTGAAGGATATAATGTTA
       :: ::::::::::::::::::: :::::::: ::::: :::::: ::::::::: ::::
MURINE TTGCTGAACTGTGAGGAGATGAGAAGGCAATTTGAAGACCTTGTCAAGGATATAACGTTA
             250       260       270       280       290       300

310       320                              330
ISF35  AACAAAGAGGAGACGAA-GAAA---------------------GATGAGGATCCTCAA
       :::::::: :::: :: :::::                     ::::::::::::::
MURINE AACAAAGAAGAGAAAAAAGAAAACAGCTTTGAAATGCAAAGAGGTGATGAGGATCCTCAA
             310       320       330       340       350       360

340       350       360       370       380       390
ISF35  ATTGCAGCACACGTTGTAAGCGAAGCCAACAGTAATGCAGCATCCGTTCTACAGTGGGCC
       ::::::::::::::::::::::::::::::::::::::::::::::::::::::::::::
MURINE ATTGCAGCACACGTTGTAAGCGAAGCCAACAGTAATGCAGCATCCGTTCTACAGTGGGCC
             370       380       390       400       410       420

400       410       420       430       440       450
ISF35  AAGAAAGGATATTATACCATGAAAAGCAACTTGGTAACCCTGGAAAATGGGAAACAGCTG
       :::::::::::::::::::::::::::::::::::::: :::::::::::::::::::::
MURINE AAGAAAGGATATTATACCATGAAAAGCAACTTGGTAATGCTTGAAAATGGGAAACAGCTG
             430       440       450       460       470       480

460       470       480       490       500       510
ISF35  ACGGTTAAAAGACAAGGACTCTATTATATCTATGCTCAAGTCACCTTCTGCTCTAATCGG
       :::::::::::: :::::::::::::::: :::: :::::::::::::::::::::::::
MURINE ACGGTTAAAAGAGAAGGACTCTATTATGTCTACACTCAAGTCACCTTCTGCTCTAATCGG
             490       500       510       520       530       540

520       530       540       550       560       570
ISF35  GAGGCTTCGAGTCAAGCCCCATTCATCGTCGGCCTCTGGCTGAAGCCCAGCAGTGGATCT
       ::: :::::::::::: :::::::::::::::::::::::::::::::::::: ::::::
MURINE GAGCCTTCGAGTCAACGCCCCATTCATCGTCGGCCTCTGGCTGAAGCCCAGCATTGGATCT
             550       560       570       580       590       600

580       590       600       610       620       630
ISF35  GAGAGAATCTTACTCAAGGCGGCAAATACCCACAGTTCCTCCCAGCTTTGCGAGCAGCAG
       ::::::::::::::::::::::::::::::::::::::::::::::: ::::::::::::
MURINE GAGAGAATCTTACTCAAGGCGGCAAATACCCACAGTTCCTCCCAGCTTTGCGAGCAGCAG
             610       620       630       640       650       660

640       650       660       670       680       690
ISF35  TCTATTCACTTGGGCGGAGTGTTTGAATTACAACCAGGTGCTTCGGTGTTTGTCAATGTG
       :: :: ::::::::::::::::::::::::::  ::: ::::: ::::::::::: ::::
MURINE TCTGTTCACTTGGGCGGAGTGTTTGAATTACAAGCTGGTGCTTCTGTGTTTGTCAACGTG
             670       680       690       700       710       720

700       710       720       730       740       750
ISF35  ACTGATCCAAGCCAAGTGAGCCATGGCACTGGCTTCACGTCCTTTGGCTTACTCAAACTC
       ::::: :::::::::::::: ::::  :::: :: :::: :::::::::::::::::::
MURINE ACTGAAGCAAGCCAAGTGATCCACAGAGTTGGCTTCTCATCTTTTGGCTTACTCAAACTC
             730       740       750       760       770       780

ISF35  TGA
       :::
MURINE TGA
```

Figure 20(a): ISF37 Nucleotide Sequence Alignment With Human CD154

```
89.8% identity in 786 nt overlap; score: 3200 E(10,000): 1.4e-258

10         20         30         40         50         60
ISF37  ATGATCGAAACATACAACCAAACTTCTCCCCGATCTGCGGCCACTGGACTGCCCATCAGC
       ::::::::::::::::::::::::::::::::::::::::::::::::::::::::::::
HUMAN  ATGATCGAAACATACAACCAAACTTCTCCCCGATCTGCGGCCACTGGACTGCCCATCAGC
              10         20         30         40         50         60

70         80         90        100        110        120
ISF37  ATGAAAATTTTTATGTATTTACTTACTGTTTTTCTTATCACCCAGATGATTGGGTCAGCA
       ::::::::::::::::::::::::::::::::::::::::::::::::::::::::::::
HUMAN  ATGAAAATTTTTATGTATTTACTTACTGTTTTTCTTATCACCCAGATGATTGGGTCAGCA
              70         80         90        100        110        120

130        140        150        160        170        180
ISF37  CTTTTTGCTGTGTATCTTCATAGAAGGCTGGACAAGATAGAAGATGAAAGGAATCTTCAT
       ::::::::::::::::::::::::::::  ::::::::::::::::::::::::::::::
HUMAN  CTTTTTGCTGTGTATCTTCATAGAAGGTTGGACAAGATAGAAGATGAAAGGAATCTTCAT
             130        140        150        160        170        180

190        200        210        220        230        240
ISF37  GAAGATTTTGTATTCATGAAAACGATACAGAGATGCAACACAGGAGAAAGATCCTTATCC
       ::::::::::::::::::::::::::::::::::::::::::::::::::::::::::::
HUMAN  GAAGATTTTGTATTCATGAAAACGATACAGAGATGCAACACAGGAGAAAGATCCTTATCC
             190        200        210        220        230        240

250        260        270        280        290        300
ISF37  TTACTGAACTGTGAGGAGATTAAAAGCCAGTTTGAAGGCTTTGTGAAGGATATAATGTTA
       ::::::::::::::::::::::::::::::::::::::::::::::::::::::::::::
HUMAN  TTACTGAACTGTGAGGAGATTAAAAGCCAGTTTGAAGGCTTTGTGAAGGATATAATGTTA
             250        260        270        280        290        300

310        320                                     330
ISF37  AACAAAGAGGAGACGAAGAAA------------------------GATGAGGATCCT
       :::::::::::::::::::::                        :::  ::  :::::
HUMAN  AACAAAGAGGAGACGAAGAAAGAAAACAGCTTTCAAATGCAAAAAGGTGATCAGAATCCT
             310        320        330        340        350        360

340        350        360        370        380        390
ISF37  CAAATTGCAGCACACGTTGTAAGCGAAGCCAACAGTAATGCAGCATCCGTTCTACAGTGG
       :::::::: ::::: ::  ::::  ::::  ::::::  :: ::   ::  ::::::::
HUMAN  CAAATTGCGGCACATGTCATAAGTGAGGCCAGCAGTAAAACAACATCTGTGTTACAGTGG
             370        380        390        400        410        420

400        410        420        430        440        450
ISF37  GCCAAGAAAGGATATTATACCATGAAAAGC AACTTGGTAACCCTGGAAAATGGGAAACAG
       ::  :  ::::::: :: :::::::   :: ::::::::::::::::::::::::::::
HUMAN  GCTGAAAAAGGATACTACACCATGAGCAAC AACTTGGTAACCCTGGAAAATGGGAAACAG
             430        440        450        460        470        480

460        470        480        490        500        510
ISF37  CTGACGGTTAAAAGACAAGGACTCTATTATATCTATGCTCAAGTCACCTTCTGCTCTAAT
       :::::::::::::::::::::::::::::::::::::  ::::::::::::::  :::
HUMAN  CTGACCGGTTAAAAGACAAGGACTCTATTATATCTATGCCCAAGTCACCTTCTGTTCCAAT
             490        500        510        520        530        540

520        530        540        550        560        570
ISF37  CGGGAGGCTTCGAGTCAAGCCCCATTCATC GTCGGCCTCTGGCTGAAGCCCAGCAGTGGA
       :::::  :::::::::::::::::::  ::    :::::::  ::: ::   : :::  ::
HUMAN  CGGGAAGCTTCGAGTCAAGCTCCATTTATA GCCAGCCTCTGCCTAAAGTCCCCCGGTAGA
              550        560        570        580        590        600

580        590        600        610        620        630
ISF37  TCTGAGAGAATCTTACTC AAGGCGGCAAATACCCACAGTTCCGCCAAGCCTTGCGGGCAG
       : :::::::::::::::: ::  :::::::::::::::::::::::::::  :::::::
HUMAN  TTCGAGAGAATCTTACTC AGAGCTGCAAATACCCACAGTTCCGCCAAACCTTGCGGGCAA
              610        620        630        640        650        660

640        650        660        670        680        690
ISF37  CAGTCTATTCACTTGGGCGGAGTGTTTGAATTACAACCAGGTGCTTCGGTGTTTGTCAAT
       ::  :: ::::::::::  :::  ::::::::  ::::::::::::::::::::::::::
HUMAN  CAATCCATTCACTTGGGAGGAGTATTTGAATTGCAACCAGGTGCTTCGGTGTTTGTCAAT
             670        680        690        700        710        720

700        710        720        730        740        750
ISF37  GTGACTGATCCAAGCCAAGTGAGCCATGGCACTGGCTTCACGTCCTTTGGCTTACTCAAA
       ::::::::::::::::::::::::::::::::::::::::::::::::::::::::::
HUMAN  GTGACTGATCCAAGCCAAGTGAGCCATGGCACTGGCTTCACGTCCTTTGGCTTACTCAAA
             730        740        750        760        770        780

ISF37  CTCTGA
       ::::::
HUMAN  CTCTGA
```

Figure 20(b): ISF37 Nucleotide Sequence Alignment With Murine CD154

```
86.7% identity in 783 nt overlap; score: 2959 E(10,000): 1.8e-238

10        20        30        40        50        60
ISF37   ATGATCGAAACATACAACCAAACTTCTCCCCGATCTGCGGCCACTGGACTGCCCATCAGC
        :::::  ::::::::::: ::::  :::: ::::  :  :::  ::::::: ::    :::
MURINE  ATGATAGAAACATACAGCCAACCTTCCCCCAGATCCGTGGCAACTGGACTTCCAGCGAGC
                10        20        30        40        50        60

70        80        90       100       110       120
ISF37   ATGAAAATTTTTATGTATTTACTTACTGTTTTTCTTATCACCCAGATGATTGGGTCAGCA
        :::::  :::::::::::::::::::::::: :::::::::::::: ::::::::  :  :
MURINE  ATGAAGATTTTTATGTATTTACTTACTGTTTTCCTTATCACCCAAATGATTGGATCTGTG
                70        80        90       100       110       120

130       140       150       160       170       180
ISF37   CTTTTTGCTGTGTATCTTCATAGAAGGCTGGACAAGATAGAAGATGAAAGGAATCTTCAT
        :::::::::::::::::::::::::::::: ::::  ::: :  :::::  :::   :: ::::::
MURINE  CTTTTTGCTGTGTATCTTCATAGAAGATTGGATAAGGTCGAAGAGGAAGTAAACCTTCAT
               130       140       150       160       170       180

190       200       210       220       230       240
ISF37   GAAGATTTTGTATTCATGAAAACGATACAGAGATGCAACACAGGAGAAAGATCCTTATCC
        :::::::::::::::::::::  ::::  :  :::::::::::: :::::::::  ::::  ::::::
MURINE  GAAGATTTTGTATTCATAAAAAAGCTAAAGAGATGCAACAAAGGAGAAGGATCTTTATCC
               190       200       210       220       230       240

250       260       270       280       290       300
ISF37   TTACTGAACTGTGAGGAGATTAAAAGCCAGTTTGAAGGCTTTGTGAAGGATATAATGTTA
        ::  :::::::::::::::::::: :  ::: :: ::::::::: :  :::: :::::::::::::::: ::::
MURINE  TTGCTGAACTGTGAGGAGATGAGAAGGCAATTTGAAGACCTTGTCAAGGATATAACGTTA
               250       260       270       280       290       300

310       320                                    330
ISF37   AACAAAGAGGAGACGAA-GAAA---------------------GATGAGGATCCTCAA
        ::::::::  ::::   ::  ::::                                      ::::::::::::::::::
MURINE  AACAAAGAAGAGAAAAAAGAAAACAGCTTTGAAATGCAAAGAGGTGATGAGGATCCTCAA
               310       320       330       340       350       360

340       350       360       370       380       390
ISF37   ATTGCAGCACACGTTGTAAGCGAAGCCAACAGTAATGCAGCATCCGTTCTACAGTGGGCC
        ::::::::::::::::::::::::::::::::::::::::::::::::::::::::::::
MURINE  ATTGCAGCACACGTTGTAAGCGAAGCCAACAGTAATGCAGCATCCGTTCTACAGTGGGCC
               370       380       390       400       410       420

400       410       420       430       440       450
ISF37   AAGAAAGGATATTATACCATGAAAAGCAACTTGGTAACCCTGGAAAATGGGAAACAGCTG
        ::::::::::::::::::::::::::::::::::::::: :: :::::::::::::::::
MURINE  AAGAAAGGATATTATACCATGAAAAGCAACTTGGTAATGCTTGAAAATGGGAAACAGCTG
               430       440       450       460       470       480

460       470       480       490       500       510
ISF37   ACGGTTAAAAGACAAGGACTCTATTATATCTATGCTCAAGTCACCTTCTGCTCTAATCGG
        :::::::::::  :::::::::::::::: ::::  :::::::::::::::::::::::::::::::
MURINE  ACGGTTAAAAGAGAAGGACTCTATTATGTCTACACTCAAGTCACCTTCTGCTCTAATCGG
               490       500       510       520       530       540

520       530       540       550       560       570
ISF37   GAGGCTTCGAGTCAAGCCCCATTCATCGTCGGCCTCTGGCTGAAGCCCAGCAGTGGATCT
        ::: :::::::::::  :::::::::::::::::::::::::::::::::::::: :::::::::
MURINE  GAGCCTTCGAGTCAACGCCCATTCATCGTCGGCCTCTGGCTGAAGCCCAGCATTGGATCT
               550       560       570       580       590       600

580       590       600       610       620       630
ISF37   GAGAGAATCTTACTCAAGGCGGCAAATACCCACAGTTCCGCCAAGCCTTGCGGGCAGCAG
        :::::::::::::::::::::::::::::::::::::::: :: :::  :::::::::::::::  :::::::
MURINE  GAGAGAATCTTACTCAAGGCGGCAAATACCCACAGTTCCTCCCAGCTTTGCGAGCAGCAG
               610       620       630       640       650       660

640       650       660       670       680       690
ISF37   TCTATTCACTTGGGCGGAGTGTTTGAATTACAACCAGGTGCTTCGGTGTTTGTCAATGTG
        :::  :::::::::::::::::::::::::  :  ::::::::::::: :::::::::::: :::
MURINE  TCTGTTCACTTGGGCGGAGTGTTTGAATTACAAGCTGGTGCTTCTGTGTTTGTCAACGTG
               670       680       690       700       710       720

700       710       720       730       740       750
ISF37   ACTGATCCAAGCCAAGTGAGCCATGGCACTGGCTTCACGTCCTTTGGCTTACTCAAACTC
        ::: :::::  :::::::::::: :::  :: ::::::: : ::::::::::::::::::::::::
MURINE  ACTGAAGCAAGCCAAGTGATCCACAGAGTTGGCTTCTCATCTTTTGGCTTACTCAAACTC
               730       740       750       760       770       780

ISF37   TGA
        :::
MURINE  TGA
```

Fig. 21(a): ISF39 Nucleotide Sequence Alignment With Human CD154

```
88.9% identity in 786 nt overlap; score: 3137 E(10,000): 2.5e-253

10         20         30         40         50         60
ISF39   ATGATCGAAACATACAACCAAACTTCTCCCCGATCTGCGGCCACTGGACTGCCCATCAGC
        ::::::::::::::::::::::::::::::::::::::::::::::::::::::::::::
HUMAN   ATGATCGAAACATACAACCAAACTTCTCCCCGATCTGCGGCCACTGGACTGCCCATCAGC
                10         20         30         40         50         60

70         80         90        100        110        120
ISF39   ATGAAAATTTTTATGTATTTACTTACTGTTTTTCTTATCACCCAGATGATTGGGTCAGCA
        ::::::::::::::::::::::::::::::::::::::::::::::::::::::::::::
HUMAN   ATGAAAATTTTTATGTATTTACTTACTGTTTTTCTTATCACCCAGATGATTGGGTCAGCA
                70         80         90        100        110        120

130        140        150        160        170        180
ISF39   CTTTTTGCTGTGTATCTTCATAGAAGGCTGGACAAGATAGAAGATGAAAGGAATCTTCAT
        :::::::::::::::::::::::::: :::::::::::::::::::::::::::::::::
HUMAN   CTTTTTGCTGTGTATCTTCATAGAAGGTTGGACAAGATAGAAGATGAAAGGAATCTTCAT
               130        140        150        160        170        180

190        200        210        220        230        240
ISF39   GAAGATTTTGTATTCATGAAAACGATACAGAGATGCAACACAGGAGAAAGATCCTTATCC
        ::::::::::::::::::::::::::::::::::::::::::::::::::::::::::::
HUMAN   GAAGATTTTGTATTCATGAAAACGATACAGAGATGCAACACAGGAGAAAGATCCTTATCC
               190        200        210        220        230        240

250        260        270        280        290        300
ISF39   TTACTGAACTGTGAGGAGATTAAAAGCCAGTTTGAAGGCTTTGTGAAGGATATAATGTTA
        ::::::::::::::::::::::::::::::::::::::::::::::::::::::::::::
HUMAN   TTACTGAACTGTGAGGAGATTAAAAGCCAGTTTGAAGGCTTTGTGAAGGATATAATGTTA
               250        260        270        280        290'       300

310        320                                       330
ISF39   AACAAAGAGGAGACGAAGAAA-------------------------GATGAGGATCCT
        :::::::::::::::::::::                         ::: :: :::::
HUMAN   AACAAAGAGGAGACGAAGAAAGAAAACAGCTTTGAAATGCAAAAGGTGATCAGAATCCT
               310        320        330        340        350        360

340        350        360        370        380        390
ISF39   CAAATTGCAGCACACGTTGTAAGCGAAGCCAACAGTAATGCAGCATCCGTTCTACAGTGG
        :::::::: ::::: :: :::: :: :::: :::::: :: :::: :: :::::::::
HUMAN   CAAATTGCGGCACATGTCATAAGTGAGGCCAGCAGTAAAACAACATCTGTGTTACAGTGG
               370        380        390        400        410        420

400        410        420        430        440        450
ISF39   GCCAAGAAAGGATATTATACCATGAAAAGC AACTTGGTAACCCTGGAAAATGGGAAACAG
        ::  ::::::::: :: :::::::  ::::  :::::::::::::::::::::::::::::
HUMAN   GCTGAAAAAGGATACTACACCATGAGCAAC AACTTGGTAACCCTGGAAAATGGGAAACAG
               430        440        450        460        470        480

460        470        480        490        500        510
ISF39   CTGACGGTTAAAAGACAAGGACTCTATTATATCTATGCTCAAGTCACCTTCTGCTCTAAT
        :::::  :::::::::::::::::::::::::::::::  :::::::::::: ::  :::
HUMAN   CTGACCGTTAAAAGACAAGGACTCTATTATATCTATGCCCAAGTCACCTTCTGTTCCAAT
               490        500        510        520        530        540

520        530        540        550        560        570
ISF39   CGGGAGCCTTCGAGTCAACGCCCATTCATCGTCGGCCTCTGGCTGAAGCCCAGCAGTGGA
        :::::  :::::::::::  :::::::  :: : :::::::: :::  ::  :  ::  ::
HUMAN   CGGGAAGCTTCGAGTCAAGCTCCATTTATAGCCAGCCTCTGCCTAAAGTCCCCCGGTAGA
               550        560        570        580        590        600

580        590        600        610        620        630
ISF39   TCTGAGAGAATCTTACTCAAGGCGGCAAATACCCACAGTTCCTCCCAGCTTTGCGAG CAG
        :  :::::::::::::::::  :: :::::::::::::::  :: :  ::::: :::
HUMAN   TTCGAGAGAATCTTACTCAGAGCTGCAAATACCCACAGTTCCGCCAAACCTTGCGGG CAA
               610        620        630        640        650        660

640        650        660        670        680        690
ISF39   CAGTCTATTCACTTGGGCGGAGTGTTTGAATTACAACCAGGTGCTTCGGTGTTTGTCAAT
        ::  :: ::::::::::: ::::: ::::::: :::::::::::::::::::: :::::
HUMAN   CAATCCATTCACTTGGGAGGAGTATTTGAATTGCAACCAGGTGCTTCGGTGTTTGTCAAT
               670        680        690        700        710        720

700        710        720        730        740        750
ISF39   GTGACTGATCCAAGCCAAGTGAGCCATGGCACTGGCTTCACGTCCTTTGGCTTACTCAAA
        ::::::::::::::::::::::::::::::::::::::::::::::::::::::::::::
HUMAN   GTGACTGATCCAAGCCAAGTGAGCCATGGCACTGGCTTCACGTCCTTTGGCTTACTCAAA
               730        740        750        760        770        780

ISF39   CTCTGA
        ::::::
HUMAN   CTCTGA
```

Fig. 21(b): ISF39 Nucleotide Sequence Alignment With Murine CD154

```
87.6% identity in 783 nt overlap; score: 3022 E(10,000): 9.8e-244

10        20        30        40        50        60
ISF39  ATGATCGAAACATACAACCAAACTTCTCCCCGATCTGCGGCCACTGGACTGCCCATCAGC
       ::::  :::::::::::  ::::  ::::  ::  ::::  :  :::  ::::::::  :  :::
MURINE ATGATAGAAACATACAGCCAACCTTCCCCCAGATCCGTGGCAACTGGACTTCCAGCGAGC
               10        20        30        40        50        60

70        80        90       100       110       120
ISF39  ATGAAAATTTTTATGTATTTACTTACTGTTTTTCTTATCACCCAGATGATTGGGTCAGCA
       ::::: :::::::::::::::::::::::::::: :::::::::::  ::::::::: :: :
MURINE ATGAAGATTTTTATGTATTTACTTACTGTTTTCCTTATCACCCAAATGATTGGATCTGTG
               70        80        90       100       110       120

130       140       150       160       170       180
ISF39  CTTTTTGCTGTGTATCTTCATAGAAGGCTGGACAAGATAGAAGATGAAAGGAATCTTCAT
       ::::::::::::::::::::::::::::: :::: ::: : ::::: :::   ::  :::::
MURINE CTTTTTGCTGTGTATCTTCATAGAAGATTGGATAAGGTCGAAGAGGAAGTAAACCTTCAT
              130       140       150       160       170       180

190       200       210       220       230       240
ISF39  GAAGATTTTGTATTCATGAAAACGATACAGAGATGCAACACAGGAGAAAGATCCTTATCC
       ::::::::::::::::::  :::: : ::  :::::::::::  ::::::::: ::: :::::::
MURINE GAAGATTTTGTATTCATAAAAAAGCTAAAGAGATGCAACAAAGGAGAAGGATCTTTATCC
              190       200       210       220       230       240

250       260       270       280       290       300
ISF39  TTACTGAACTGTGAGGAGATTAAAAGCCAGTTTGAAGGCTTTGTGAAGGATATAATGTTA
       :: ::::::::::::::::::: ::: :: ::::::::::: ::::::::::::::: ::::
MURINE TTGCTGAACTGTGAGGAGATGAGAAGGCAATTTGAAGACCTTGTCAAGGATATAACGTTA
              250       260       270       280       290       300

310       320                                    330
ISF39  AACAAAGAGGAGACGAA-GAAA---------------------GATGAGGATCCTCAA
       :::::::::: ::::  :: ::::                     :::::::::::::::
MURINE AACAAAGAAGAGAAAAAAGAAAACAGCTTTGAAATGCAAAGAGGTGATGAGGATCCTCAA
              310       320       330       340       350       360

340       350       360       370       380       390
ISF39  ATTGCAGCACACGTTGTAAGCGAAGCCAACAGTAATGCAGCATCCGTTCTACAGTGGGCC
       ::::::::::::::::::::::::::::::::::::::::::::::::::::::::::::
MURINE ATTGCAGCACACGTTGTAAGCGAAGCCAACAGTAATGCAGCATCCGTTCTACAGTGGGCC
              370       380       390       400       410       420

400       410       420       430       440       450
ISF39  AAGAAAGGATATTATACCATGAAAAGCAACTTGGTAACCCTGGAAAATGGGAAACAGCTG
       ::::::::::::::::::::::::::::::::::::  :: :::::::::::::::::::
MURINE AAGAAAGGATATTATACCATGAAAAGCAACTTGGTAATGCTTGAAAATGGGAAACAGCTG
              430       440       450       460       470       480

460       470       480       490       500       510
ISF39  ACGGTTAAAAGACAAGGACTCTATTATATCTATGCTCAAGTCACCTTCTGCTCTAATCGG
       :::::::::::: :::::::::::::::: :::: :::::::::::::::::::::::::
MURINE ACGGTTAAAAGAGAAGGACTCTATTATGTCTACACTCAAGTCACCTTCTGCTCTAATCGG
              490       500       510       520       530       540

520       530       540       550       560       570
ISF39  GAGCCTTCGAGTCAACGCCCATTCATCGTCGGCCTCTGGCTGAAGCCCAGCAGTGGATCT
       :::::::::::::::::::::::::::::::::::::::::::::::::::::  :::::
MURINE GAGCCTTCGAGTCAACGCCCATTCATCGTCGGCCTCTGGCTGAAGCCCAGCATTGGATCT
              550       560       570       580       590       600

580       590       600       610       620       630
ISF39  GAGAGAATCTTACTCAAGGCGGCAAATACCCACAGTTCCTCCCAGCTTTGCGAGCAGCAG
       ::::::::::::::::::::::::::::::::::::::::::::::::::::::::::::
MURINE GAGAGAATCTTACTCAAGGCGGCAAATACCCACAGTTCCTCCCAGCTTTGCGAGCAGCAG
              610       620       630       640       650       660

640       650       660       670       680       690
ISF39  TCTATTCACTTGGGCGGAGTGTTTGAATTACAACCAGGTGCTTCGGTGTTTGTCAATGTG
       :::  :::::::::::::::::::::::::::: :  :::::::: ::::::::::: :::
MURINE TCTGTTCACTTGGGCGGAGTGTTTGAATTACAAGCTGGTGCTTCTGTGTTTGTCAACGTG
              670       680       690       700       710       720

700       710       720       730       740       750
ISF39  ACTGATCCAAGCCAAGTGAGCCATGGCACTGGCTTCACGTCCTTTGGCTTACTCAAACTC
       ::::: ::::::::::::::: :: :  :::::::: :::  :::: :::::::::::::
MURINE ACTGAAGCAAGCCAAGTGATCCACAGAGTTGGCTTCTCATCTTTTGGCTTACTCAAACTC
              730       740       750       760       770       780

ISF39  TCA
       :::
MURINE TGA
```

Fig. 22(a): ISF41 Nucleotide Sequence Alignment With Human CD154

89.4% identity in 786 nt overlap; score: 3173 E(10,000): 2.5e-256

```
              10         20         30         40         50         60
ISF41   ATGATCGAAACATACAACCAAACTTCTCCCCGATCTGCGGCCACTGGACTGCCCATCAGC
        ::::::::::::::::::::::::::::::::::::::::::::::::::::::::::::
HUMAN   ATGATCGAAACATACAACCAAACTTCTCCCCGATCTGCGGCCACTGGACTGCCCATCAGC
              10         20         30         40         50         60

70         80         90        100        110        120
ISF41   ATGAAAATTTTTATGTATTTACTTACTGTTTTTCTTATCACCCAGATGATTGGGTCAGCA
        ::::::::::::::::::::::::::::::::::::::::::::::::::::::::::::
HUMAN   ATGAAAATTTTTATGTATTTACTTACTGTTTTTCTTATCACCCAGATGATTGGGTCAGCA
              70         80         90        100        110        120

130        140        150        160        170        180
ISF41   CTTTTTGCTGTGTATCTTCATAGAAGGCTGGACAAGATAGAAGATGAAAGGAATCTTCAT
        ::::::::::::::::::::::::::::::: ::::::::::::::::::::::::::::
HUMAN   CTTTTTGCTGTGTATCTTCATAGAAGGTTGGACAAGATAGAAGATGAAAGGAATCTTCAT
             130        140        150        160        170        180

190        200        210        220        230        240
ISF41   GAAGATTTTGTATTCATGAAAACGATACAGAGATGCAACACAGGAGAAAGATCCTTATCC
        ::::::::::::::::::::::::::::::::::::::::::::::::::::::::::::
HUMAN   GAAGATTTTGTATTCATGAAAACGATACAGAGATGCAACACAGGAGAAAGATCCTTATCC
             190        200        210        220        230        240

250        260        270        280        290        300
ISF41   TTACTGAACTGTGAGGAGATTAAAAGCCAGTTTGAAGGCTTTGTGAAGGATATAATGTTA
        ::::::::::::::::::::::::::::::::::::::::::::::::::::::::::::
HUMAN   TTACTGAACTGTGAGGAGATTAAAAGCCAGTTTGAAGGCTTTGTGAAGGATATAATGTTA
             250        260        270        280        290        300

310        320                                         330
ISF41   AACAAAGAGGAGACGAAGAAA------------------------GATGAGGATCCT
        :::::::::::::::::::::                        ::: :: :::::
HUMAN   AACAAAGAGGAGACGAAGAAAGAAAACAGCTTTGAAATGCAAAAAGGTGATCAGAATCCT
             310        320        330        340        350        360

340        350        360        370        380        390
ISF41   CAAATTGCAGCACACGTTGTAAGCGAAGCCAACAGTAATGCAGCATCCGTTCTACAGTGG
        :::::::: :::::  ::  ::::  ::::  :::::::  ::::::  ::: :::::::
HUMAN   CAAATTGCGGCACATGTCATAAGTGAGGCCAGCAGTAAAACAACATCTGTGTTACAGTGG
             370        380        390        400        410        420

400        410        420        430        440        450
ISF41   GCCAAGAAAGGATATTATACCATGAAAAGC AACTTGGTAACCCTGGAAAATGGGAAACAG
        ::  : :::::::: :: ::::::: :::: :::::::::::::::::::::::::::::
HUMAN   GCTGAAAAAGGATACTACACCATGAGCAAC AACTTGGTAACCCTGGAAAATGGGAAACAG
             430        440        450        460        470        480

460        470        480        490        500        510
ISF41   CTGACGGTTAAAAGACAAGGACTCTATTATATCTATGCTCAAGTCACCTTCTGCTCTAAT
        ::::: ::::::::::::::::::::::::::::::: ::::::::::::::: ::  ::
HUMAN   CTGACCGTTAAAAGACAAGGACTCTATTATATCTATGCCCAAGTCACCTTCTGTTCCAAT
             490        500        510        520        530        540

520        530        540        550        560        570
ISF41   CGGGAGCCTTCGAGTCAACGCCCATTCATCGTCGGCCTCTGGCTGAAGCCCAGCAGTGGA
        :::::  ::::::::::: :::  ::: : :::   ::::  ::::  ::: ::: ::::
HUMAN   CGGGAAGCTTCGAGTCAAGCTCCATTTATAGCCAGCCTCTGCCTAAAGTCCCCCGGTAGA
             550        560        570        580        590        600

580        590        600        610        620        630
ISF41   TCTGAGAGAATCTTACTCAAG GCGGCAAATACCCACAGTTCCGCCAAGCCCTTGCGGGCAG
        : :::::::::::::::: :: ::::::::::::::::::::::::::: ::::::::::
HUMAN   TTCGAGAGAATCTTACTCAGA GCTGCAAATACCCACAGTTCCGCCAAACCTTGCGGGCAA
             610        620        630        640        650        660

640        650        660        670        680        690
ISF41   CAGTCTATTCACTTGGGCGGAGTGTTTGAATTACAACCAGGTGCTTCGGTGTTTGTCAAT
        :: :: ::::::::::::::: :::: :::::: ::::::::::::::::::: ::::::
HUMAN   CAATCCATTCACTTGGGAGGAGTATTTGAATTGCAACCAGGTGCTTCGGTGTTTGTCAAT
             670        680        690        700        710        720

700        710        720        730        740        750
ISF41   GTGACTGATCCAAGCCAAGTGAGCCATGGCACTGGCTTCACGTCCTTTGGCTTACTCAAA
        ::::::::::::::::::::::::::::::::::::::::::::::::::::::::::::
HUMAN   GTGACTGATCCAAGCCAAGTGAGCCATGGCACTGGCTTCACGTCCTTTGGCTTACTCAAA
             730        740        750        760        770        780

ISF41   CTCTGA
        ::::::
HUMAN   CTCTGA
```

Fig. 22(b): ISF41 Nucleotide Sequence Alignment With Murine CD154

```
87.1% identity in 783 nt overlap; score: 2986 E(10,000): 9.8e-241

10        20        30        40        50        60
ISF41   ATGATCGAAACATACAACCAAACTTCTCCCCGATCTGCGGCCACTGGACTGCCCATCAGC
        :::::  :::::::::::  ::::  :::  :::: : :::  :::::::::: :: :::
MURINE  ATGATAGAAACATACAGCCAACCTTCCCCCAGATCCGTGGCAACTGGACTTCCAGCGAGC
                10        20        30        40        50        60

70        80        90       100       110       120
ISF41   ATGAAAATTTTTATGTATTTACTTACTGTTTTTCTTATCACCCAGATGATTGGGTCAGCA
        :::::  :::::::::::::::::::::::::  :::::::::: :::::::::  :: :
MURINE  ATGAAGATTTTTATGTATTTACTTACTGTTTTCCTTATCACCCAAATGATTGGATCTGTG
                70        80        90       100       110       120

130       140       150       160       170       180
ISF41   CTTTTTGCTGTGTATCTTCATAGAAGGCTGGACAAGATAGAAGATGAAAGGAATCTTCAT
        :::::::::::::::::::::::::::  ::::  ::  :  :::::  ::  :::::::
MURINE  CTTTTTGCTGTGTATCTTCATAGAAGATTGGATAAGGTCGAAGAGGAAGTAAACCTTCAT
               130       140       150       160       170       180

190       200       210       220       230       240
ISF41   GAAGATTTTGTATTCATGAAAACGATACAGAGATGCAACACAGGAGAAAGATCCTTATCC
        ::::::::::::::::::  :  ::  :::::::::::::  ::::::  ::::::::::
MURINE  GAAGATTTTGTATTCATAAAAAAGCTAAAGAGATGCAACAAAGGAGAAGGATCTTTATCC
               190       200       210       220       230       240

250       260       270       280       290       300
ISF41   TTACTGAACTGTGAGGAGATTAAAAGCCAGTTTGAAGGCTTTGTGAAGGATATAATGTTA
        :: ::::::::::::::::: ::: :: :::::::: : ::::::::::::::::: ::::
MURINE  TTGCTGAACTGTGAGGAGATGAGAAGGCAATTTGAAGACCTTGTCAAGGATATAACGTTA
               250       260       270       280       290       300

310       320                            330
ISF41   AACAAAGAGGAGACGAA-GAAA--------------------GATGAGGATCCTCAA
        :::::::::  ::::   :: ::::                 :::::::::::::::
MURINE  AACAAAGAAGAGAAAAAAGAAAACAGCTTTGAAATGCAAAGAGGTGATGAGGATCCTCAA
               310       320       330       340       350       360

340       350       360       370       380       390
ISF41   ATTGCAGCACACGTTGTAAGCGAAGCCAACAGTAATGCAGCATCCGTTCTACAGTGGGCC
        ::::::::::::::::::::::::::::::::::::::::::::::::::::::::::::
MURINE  ATTGCAGCACACGTTGTAAGCGAAGCCAACAGTAATGCAGCATCCGTTCTACAGTGGGCC
               370       380       390       400       410       420

400       410       420       430       440       450
ISF41   AAGAAAGGATATTATACCATGAAAAGCAACTTGGTAACCCTGGAAAATGGGAAACAGCTG
        ::::::::::::::::::::::::::::::::::::  :: ::::::::::::::::::
MURINE  AAGAAAGGATATTATACCATGAAAAGCAACTTGGTAATGCTTGAAAATGGGAAACAGCTG
               430       440       450       460       470       480

460       470       480       490       500       510
ISF41   ACGGTTAAAAGACAAGGACTCTATTATATCTATGCTCAAGTCACCTTCTGCTCTAATCGG
        ::::::::::: ::::::::::::::: ::::  :::::::::::::::::::::::::
MURINE  ACGGTTAAAAGAGAAGGACTCTATTATGTCTACACTCAAGTCACCTTCTGCTCTAATCGG
               490       500       510       520       530       540

520       530       540       550       560       570
ISF41   GAGCCTTCGAGTCAACGCCCATTCATCGTCGGCCTCTGGCTGAAGCCCAGCAGTGGATCT
        ::::::::::::::::::::::::::::::::::::::::::::::::::::  :::::
MURINE  GAGCCTTCGAGTCAACGCCCATTCATCGTCGGCCTCTGGCTGAAGCCCAGCATTGGATCT
               550       560       570       580       590       600

580       590       600       610       620       630
ISF41   GAGAGAATCTTACTCAAGGCGGCAAATACCCACAGTTCCGCCAAGCCTTGCGGGCAGCAG
        :::::::::::::::::::::::::::::::::::::: ::  :::  ::::  ::::::
MURINE  GAGAGAATCTTACTCAAGGCGGCAAATACCCACAGTTCCTCCCCAGCTTTGCGAGCAGCAG
               610       620       630       640       650       660

640       650       660       670       680       690
ISF41   TCTATTCACTTGGGCGGAGTGTTTGAATTACAACCAGGTGCTTCGGTGTTTGTCAATGTG
        :::  :::::::::::::::::::::::::::: : :::::::: :::::::::: :::
MURINE  TCTGTTCACTTGGGCGGAGTGTTTGAATTACAAGCTGGTGCTTCTGTGTTTGTCAACGTG
               670       680       690       700       710       720

700       710       720       730       740       750
ISF41   ACTGATCCAAGCCAAGTGAGCCATGGCACTGGCTTCACGTCCTTTGGCTTACTCAAACTC
        :::::  ::::::::::::: : ::   ::::::::::::  : :::::::::::::::
MURINE  ACTGAAGCAAGCCAAGTGATCCACAGAGTTGGCTTCTCATCTTTTGGCTTACTCAAACTC
               730       740       750       760       770       780

ISF41   TGA
        :::
MURINE  TGA
```

Fig. 23:    ISF30 Amino Acid Sequence Alignment to Human and Mouse CD154

81.6% identity in 261 residues overlap; Score: 1083.0; Gap frequency: 0.4%

```
ISF30,      1 MIETYSQPSPRSVATGLPASMKIFMYLLTVFLITQMIGSVLFAVYLHRRLDKVEEEVNLH
HUMAN       1 MIETYNQTSPRSAATGLPISMKIFMYLLTVFLITQMIGSALFAVYLHRRLDKIEDERNLH
              *****  * ****  ***** ***************** ************ *  * ***

ISF30,     61 EDFVFIKKLKRCNKGEGSLSLLNCEEMRRQFEDLVKDITLNKEE-KKENSFEMQRGDEDP
HUMAN      61 EDFVFMKTIQRCNTGERSLSLLNCEEIKSQFEGFVKDIMLNKEETKKENSFEMQKGDQNP
              *****   *  ***  **  ********   ***  ****  *****  ********** **   *

ISF30,    120 QIAAHVVSEANSNAASVLQWAKKGYYTMKSNLVTLENGKQLTVKRQGLYYIYAQVTFCSN
HUMAN     121 QIAAHVISEASSKTTSVLQWAEKGYYTMSNNLVTLENGKQLTVKRQGLYYIYAQVTFCSN
              ****** *** *       ****** ******  ****************************

ISF30,    180 REPSSQRPFIVGLWLKPSSGSERILLKAANTHSSSQLCEQQSVHLGGVPELQPGASVFVN
HUMAN     181 REASSQAPFIASLCLKSPGRFERILLRAANTHSSAKPCGQQSIHLGGVPELQPGASVFVN
              ** *** *** *  *  **     ***** ******    * *** ****************

ISF30,    240 VTDPSQVSHGTGFTSFGLLKL
HUMAN     241 VTDPSQVSHGTGFTSFGLLKL
              *********************
```

95.8% identity in 260 residues overlap; Score: 1272.0; Gap frequency: 0.0%

```
ISF30,      1 MIETYSQPSPRSVATGLPASMKIFMYLLTVFLITQMIGSVLFAVYLHRRLDKVEEEVNLH
MURINE      1 MIETYSQPSPRSVATGLPASMKIFMYLLTVFLITQMIGSVLFAVYLHRRLDKVEEEVNLH
              ************************************************************

ISF30,     61 EDFVFIKKLKRCNKGEGSLSLLNCEEMRRQFEDLVKDITLNKEEKKENSFEMQRGDEDPQ
MURINE     61 EDFVFIKKLKRCNKGEGSLSLLNCEEMRRQFEDLVKDITLNKEEKKENSFEMQRGDEDPQ
              ************************************************************

ISF30,    121 IAAHVVSEANSNAASVLQWAKKGYYTMKSNLVTLENGKQLTVKRQGLYYIYAQVTFCSNR
MURINE    121 IAAHVVSEANSNAASVLQWAKKGYYTMKSNLVMLENGKQLTVKREGLYYVYTQVTFCSNR
              *******************************  *********** **** * *******

ISF30,    181 EPSSQRPFIVGLWLKPSSGSERILLKAANTHSSSQLCEQQSVHLGGVFELQPGASVFVNV
MURINE    181 EPSSQRPFIVGLWLKPSSGSERILLKAANTHSSSQLCEQQSVHLGGVFELQAGASVFVNV
              ************************************************** ********

ISF30,    241 TDPSQVSHGTGFTSFGLLKL
MURINE    241 TEASQVIHRVGFSSFGLLKL
              *  *  *  ** ********
```

Fig. 24:   ISF32 Amino Acid Sequence Alignment to Human and Mouse CD154

82.4% identity in 261 residues overlap; Score: 1093.0; Gap frequency: 0.4%

```
ISF32,      1 MIETYSQPSPRSVATGLPASMKIFMYLLTVFLITQMIGSVLFAVYLHRRLDKVEEEVNLH
HUMAN       1 MIETYNQTSPRSAATGLPISMKIFMYLLTVFLITQMIGSALFAVYLHRRLDKIEDERNLH
              ***** * **** ***** ******************* **************  * ***

ISF32,     61 EDFVFIKKLKRCNKGEGSLSLLNCEEMRRQFEDLVKDITLNKEE-KKENSFEMQRGDEDP
HUMAN      61 EDFVFMKTIQRCNTGERSLSLLNCEEIKSQFEGFVKDIMLNKEETKKENSFEMQKGDQNP
              ***** *   *** ** ********  * *** ***** ****  ********* **  *

ISF32,    120 QIAAHVVSEANSNAASVLQWAKKGYYTMKSNLVTLENGKQLTVKRQGLYYIYAQVTFCSN
HUMAN     121 QIAAHVISEASSKTTSVLQWAEKGYYTMSNNLVTLENGKQLTVKRQGLYYIYAQVTFCSN
              ****** *** *   ****** ****** ******************************

ISF32,    180 REASSQAPFIVGLWLKPSSGSERILLKAANTHSSSQLCEQQSVHLGGVPELQPGASVFVN
HUMAN     181 REASSQAPFIASLCLKSPGRFERILLRAANTHSSAKPCGQQSIHLGGVPELQPGASVFVN
              **********  * **     ***** ******   * *** *****************

ISF32,    240 VTDPSQVSHGTGFTSFGLLKL
HUMAN     241 VTDPSQVSHGTGFTSFGLLKL
              *********************
```

95.0% identity in 260 residues overlap; Score: 1258.0; Gap frequency: 0.0%

```
ISF32,      1 MIETYSQPSPRSVATGLPASMKIFMYLLTVFLITQMIGSVLFAVYLHRRLDKVEEEVNLH
MURINE      1 MIETYSQPSPRSVATGLPASMKIFMYLLTVFLITQMIGSVLFAVYLHRRLDKVEEEVNLH
              ************************************************************

ISF32,     61 EDFVFIKKLKRCNKGEGSLSLLNCEEMRRQFEDLVKDITLNKEEKKENSFEMQRGDEDPQ
MURINE     61 EDFVFIKKLKRCNKGEGSLSLLNCEEMRRQFEDLVKDITLNKEEKKENSFEMQRGDEDPQ
              ************************************************************

ISF32,    121 IAAHVVSEANSNAASVLQWAKKGYYTMKSNLVTLENGKQLTVKRQGLYYIYAQVTFCSNR
MURINE    121 IAAHVVSEANSNAASVLQWAKKGYYTMKSNLVMLENGKQLTVKREGLYYVYTQVTFCSNR
              ******************************** ********** **** * ********

ISF32,    181 EASSQAPFIVGLWLKPSSGSERILLKAANTHSSSQLCEQQSVHLGGVFELQPGASVFVNV
MURINE    181 EPSSQRPFIVGLWLKPSSGSERILLKAANTHSSSQLCEQQSVHLGGVFELQAGASVFVNV
              * *** ******************************************** ********

ISF32,    241 TDPSQVSHGTGFTSFGLLKL
MURINE    241 TEASQVIHRVGFSSFGLLKL
              *   *** *  ** ******
```

Fig. 25:    ISF34 Amino Acid Sequence Alignment to Human and Mouse CD154

82.8% identity in 261 residues overlap; Score: 1094.0; Gap frequency: 0.4%

```
ISF34,     1 MIETYSQPSPRSVATGLPASMKIFMYLLTVFLITQMIGSVLFAVYLHRRLDKVEEEVNLH
HUMAN      1 MIETYNQTSPRSAATGLPISMKIFMYLLTVFLITQMIGSALFAVYLHRRLDKIEDERNLH
             ***** * **** ***** ************************ ************* * * ***

ISF34,    61 EDFVFIKKLKRCNKGEGSLSLLNCEEMRRQFEDLVKDITLNKEE-KKENSFEMQRGDEDP
HUMAN     61 EDFVFMKTIQRCNTGERSLSLLNCEEIKSQFEGFVKDIMLNKEETKKENSFEMQKGDQNP
             ***** *   *** ** ********  *** **** ***** ******** **   *

ISF34,   120 QIAAHVVSEANSNAASVLQWAKKGYYTMKSNLVTLENGKQLTVKRQGLYYIYAQVTFCSN
HUMAN    121 QIAAHVISEASSKTTSVLQWAEKGYYTMSNNLVTLENGKQLTVKRQGLYYIYAQVTFCSN
             ****** *** *      ****** ****** ************************

ISF34,   180 REASSQAPPIVGLWLKPSSGSERILLKAANTHSSSQLCEQQSIHLGGVFELQPGASVFVN
HUMAN    181 REASSQAPPIASLCLKSPGRFERILLRAANTHSSAKPCGQQSIHLGGVFELQPGASVFVN
             **********  * **     ***** ******   *  **********************

ISF34,   240 VTDPSQVSHGTGFTSFGLLKL
HUMAN    241 VTDPSQVSHGTGFTSFGLLKL
             *********************
```

94.6% identity in 260 residues overlap; Score: 1257.0; Gap frequency: 0.0%

```
ISF34,     1 MIETYSQPSPRSVATGLPASMKIFMYLLTVFLITQMIGSVLFAVYLHRRLDKVEEEVNLH
MURINE     1 MIETYSQPSPRSVATGLPASMKIFMYLLTVFLITQMIGSVLFAVYLHRRLDKVEEEVNLH
             ************************************************************

ISF34,    61 EDFVFIKKLKRCNKGEGSLSLLNCEEMRRQFEDLVKDITLNKEEKKENSFEMQRGDEDPQ
MURINE    61 EDFVFIKKLKRCNKGEGSLSLLNCEEMRRQFEDLVKDITLNKEEKKENSFEMQRGDEDPQ
             ************************************************************

ISF34,   121 IAAHVVSEANSNAASVLQWAKKGYYTMKSNLVTLENGKQLTVKRQGLYYIYAQVTFCSNR
MURINE   121 IAAHVVSEANSNAASVLQWAKKGYYTMKSNLVMLENGKQLTVKREGLYYVYTQVTFCSNR
             ******************************** *********** **** * *******

ISF34,   181 EASSQAPPIVGLWLKPSSGSERILLKAANTHSSSQLCEQQSIHLGGVFELQPGASVFVNV
MURINE   181 EPSSQRPFIVGLWLKPSSGSERILLKAANTHSSSQLCEQQSVHLGGVFELQAGASVFVNV
             * ***  * *********************************** ********* *******

ISF34,   241 TDPSQVSHGTGFTSFGLLKL
MURINE   241 TEASQVIHRVGFSSFGLLKL
             *  *** *  ** *******
```

Fig. 26: ISF36 Amino Acid Sequence Alignment to Human and Mouse CD154

84.3% identity in 261 residues overlap; Score: 1119.0; Gap frequency: 0.4%

```
ISF36,     1 MIETYSQPSRSVATGLPASMKIFMYLLTVFLITQMIGSVLFAVYLHRRLDKVEEEVNLH
HUMAN      1 MIETYNQTSPRSAATGLPISMKIFMYLLTVFLITQMIGSALFAVYLHRRLDKIEDERNLH
             ***** * **** *****************  *********** *  * * ***

ISF36,    61 EDFVFIKKLKRCNKGEGSLSLLNCEEMRRQFEDLVKDITLNKEE-KKENSFEMQRGDEDP
HUMAN     61 EDFVFMKTIQRCNTGERSLSLLNCEEIKSQFEGFVKDIMLNKEETKKENSFEMQKGDQNP
             *****  *   *** ** ********   **  ***** *****  ********** * *

ISF36,   120 QIAAHVVSEANSNAASVLQWAKKGYYTMKSNLVTLENGKQLTVKRQGLYYIYAQVTFCSN
HUMAN    121 QIAAHVISEASSKTTSVLQWAEKGYYTMSNNLVTLENGKQLTVKRQGLYYIYAQVTFCSN
             ****** ***  *  ****** ****** * *****************************

ISF36,   180 REASSQAPPIVGLWLKPSSGSERILLKAANTHSSAKPCGQQSIHLGGVPELQPGASVFVN
HUMAN    181 REASSQAPFIASLCLKSPGRFERILLRAANTHSSAKPCGQQSIHLGGVPELQPGASVFVN
             ********* * **   *****   *********************************

ISF36,   240 VTDPSQVSHGTGPTSFGLLKL
HUMAN    241 VTDPSQVSHGTGPTSFGLLKL
             *********************
```

93.1% identity in 260 residues overlap; Score: 1236.0; Gap frequency: 0.0%

```
ISF36,     1 MIETYSQPSPRSVATGLPASMKIFMYLLTVFLITQMIGSVLFAVYLHRRLDKVEEEVNLH
MURINE     1 MIETYSQPSPRSVATGLPASMKIFMYLLTVFLITQMIGSVLFAVYLHRRLDKVEEEVNLH
             ************************************************************

ISF36,    61 EDFVFIKKLKRCNKGEGSLSLLNCEEMRRQFEDLVKDITLNKEEKKENSFEMQRGDEDPQ
MURINE    61 EDFVFIKKLKRCNKGEGSLSLLNCEEMRRQFEDLVKDITLNKEEKKENSFEMQRGDEDPQ
             ************************************************************

ISF36,   121 IAAHVVSEANSNAASVLQWAKKGYYTMKSNLVTLENGKQLTVKRQGLYYIYAQVTFCSNR
MURINE   121 IAAHVVSEANSNAASVLQWAKKGYYTMKSNLVMLENGKQLTVKREGLYYVYTQVTFCSNR
             ******************************** ********** **** * *******

ISF36,   181 EASSQAPPIVGLWLKPSSGSERILLKAANTHSSAKPCGQQSIHLGGVFELQPGASVFVNV
MURINE   181 EPSSQRPFIVGLWLKPSSGSERILLKAANTHSSSQLCEQQSVHLGGVFELQAGASVFVNV
             * *** * ************************   * ***  ******* * *******

ISF36,   241 TDPSQVSHGTGFTSFGLLKL
MURINE   241 TEASQVIHRVGFSSFGLLKL
              *  ***  **  *******
```

Fig. 27:  ISF38 Amino Acid Sequence Alignment to Human and Mouse CD154

82.0% identity in 261 residues overlap; Score: 1084.0; Gap frequency: 0.4%

```
ISF38,      1 MIETYSQPSPRSVATGLPASMKIFMYLLTVFLITQMIGSVLFAVYLHRRLDKVEEEVNLH
HUMAN       1 MIETYNQTSPRSAATGLPISMKIFMYLLTVFLITQMIGSALFAVYLHRRLDKIEDERNLH
              ***** * **** ***** ************************ ************ * * ***

ISF38,     61 EDFVFIKKLKRCNKGEGSLSLLNCEEMRRQFEDLVKDITLNKEE-KKENSFEMQRGDEDP
HUMAN      61 EDFVFMKTIQRCNTGERSLSLLNCEEIKSQFEGFVKDIMLNKEETKKENSFEMQKGDQNP
              ***** *   *** ** ********  *** **** ***** ********** **  *

ISF38,    120 QIAAHVVSEANSNAASVLQWAKKGYYTMKSNLVTLENGKQLTVKRQGLYYIYAQVTFCSN
HUMAN     121 QIAAHVISEASSKTTSVLQWAEKGYYTMSNNLVTLENGKQLTVKRQGLYYIYAQVTFCSN
              ****** *** *  ****** ******  *******************************

ISF38,    180 REPSSQRPFIVGLWLKPSSGSERILLKAANTHSSSQLCEQQSIHLGGVPELQPGASVFVN
HUMAN     181 REASSQAPFIASLCLKSPGRFERILLRAANTHSSAKPCGQQSIHLGGVPELQPGASVFVN
              ** *** *** *  **     ***** ******    *********************

ISF38,    240 VTDPSQVSHGTGFTSFGLLKL
HUMAN     241 VTDPSQVSHGTGFTSFGLLKL
              *********************
```

95.4% identity in 260 residues overlap; Score: 1271.0; Gap frequency: 0.0%

```
ISF38,      1 MIETYSQPSPRSVATGLPASMKIFMYLLTVFLITQMIGSVLFAVYLHRRLDKVEEEVNLH
MURINE      1 MIETYSQPSPRSVATGLPASMKIFMYLLTVFLITQMIGSVLFAVYLHRRLDKVEEEVNLH
              ************************************************************

ISF38,     61 EDFVFIKKLKRCNKGEGSLSLLNCEEMRRQFEDLVKDITLNKEEKKENSFEMQRGDEDPQ
MURINE     61 EDFVFIKKLKRCNKGEGSLSLLNCEEMRRQFEDLVKDITLNKEEKKENSFEMQRGDEDPQ
              ************************************************************

ISF38,    121 IAAHVVSEANSNAASVLQWAKKGYYTMKSNLVTLENGKQLTVKRQGLYYIYAQVTFCSNR
MURINE    121 IAAHVVSEANSNAASVLQWAKKGYYTMKSNLVMLENGKQLTVKREGLYYVYTQVTFCSNR
              ******************************** ********** **** * *******

ISF38,    181 EPSSQRPFIVGLWLKPSSGSERILLKAANTHSSSQLCEQQSIHLGGVPELQPGASVFVNV
MURINE    181 EPSSQRPFIVGLWLKPSSGSERILLKAANTHSSSQLCEQQSVHLGGVPELQAGASVFVNV
              ***************************************** ********* *******

ISF38,    241 TDPSQVSHGTGFTSFGLLKL
MURINE    241 TEASQVIHRVGFSSFGLLKL
              *  *** *  ** *******
```

Fig. 28: ISF40 Amino Acid Sequence Alignment to Human and Mouse CD154

83.5% identity in 261 residues overlap; Score: 1109.0; Gap frequency: 0.4%

```
ISF40,     1 MIETYSQPSPRSVATGLPASMKIFMYLLTVFLITQMIGSVLFAVYLHRRLDKVEEEVNLH
HUMAN      1 MIETYNQTSPRSAATGLPISMKIFMYLLTVFLITQMIGSALFAVYLHRRLDKIEDERNLH
             *****  * ****  ***** ******************** ************  *  ***

ISF40,    61 EDFVFIKKLKRCNKGEGSLSLLNCEEMRRQFEDLVKDITLNKEE-KKENSFEMQRGDEDP
HUMAN     61 EDFVFMKTIQRCNTGERSLSLLNCEEIKSQFEGFVKDIMLNKEETKKENSFEMQKGDQNP
             *****  *   *** **  ********   ***    ***   **** *****  ****  **   *

ISF40,   120 QIAAHVVSEANSNAASVLQWAKKGYYTMKSNLVTLENGKQLTVKRQGLYYIYAQVTPCSN
HUMAN    121 QIAAHVISEASSKTTSVLQWAEKGYYTMSNNLVTLENGKQLTVKRQGLYYIYAQVTPCSN
             ****** ***  *   ****** ****** *  ***************************

ISF40,   180 REPSSQRPFIVGLWLKPSSGSERILLKAANTHSSAKPCGQQSIHLGGVFELQPGASVFVN
HUMAN    181 REASSQAPFIASLCLKSPGRFERILLRAANTHSSAKPCGQQSIHLGGVFELQPGASVFVN
             ** ***  ***    *   **     *****  ********************************

ISF40,   240 VTDPSQVSHGTGFTSFGLLKL
HUMAN    241 VTDPSQVSHGTGFTSFGLLKL
             *********************
```

93.8% identity in 260 residues overlap; Score: 1250.0; Gap frequency: 0.0%

```
ISF40,     1 MIETYSQPSPRSVATGLPASMKIFMYLLTVFLITQMIGSVLFAVYLHRRLDKVEEEVNLH
MURINE     1 MIETYSQPSPRSVATGLPASMKIFMYLLTVFLITQMIGSVLFAVYLHRRLDKVEEEVNLH
             ************************************************************

ISF40,    61 EDFVFIKKLKRCNKGEGSLSLLNCEEMRRQFEDLVKDITLNKEEKKENSFEMQRGDEDPQ
MURINE    61 EDFVFIKKLKRCNKGEGSLSLLNCEEMRRQFEDLVKDITLNKEEKKENSFEMQRGDEDPQ
             ************************************************************

ISF40,   121 IAAHVVSEANSNAASVLQWAKKGYYTMKSNLVTLENGKQLTVKRQGLYYIYAQVTFCSNR
MURINE   121 IAAHVVSEANSNAASVLQWAKKGYYTMKSNLVMLENGKQLTVKREGLYYVYTQVTFCSNR
             ******************************** ********** **** * *******

ISF40,   181 EPSSQRPFIVGLWLKPSSGSERILLKAANTHSSAKPCGQQSIHLGGVFELQPGASVFVNV
MURINE   181 EPSSQRPFIVGLWLKPSSGSERILLKAANTHSSSQLCEQQSVHLGGVFELQAGASVFVNV
             *********************************   *** ********* ********

ISF40,   241 TDPSQVSHGTGFTSFGLLKL
MURINE   241 TEASQVIHRVGFSSFGLLKL
             *  *** *  **  ******
```

Fig. 29:    ISF31 Amino Acid Sequence Alignment to Human and Mouse CD154

```
86.6% identity in 261 residues overlap; Score: 1108.0; Gap frequency: 3.4%

ISF31,     1  MIETYNQTSPRSAATGLPISMKIFMYLLTVFLITQMIGSALFAVYLHRRLDKIEDERNLH
HUMAN      1  MIETYNQTSPRSAATGLPISMKIFMYLLTVFLITQMIGSALFAVYLHRRLDKIEDERNLH
              ************************************************************

ISF31,    61  EDFVFMKTIQRCNTGERSLSLLNCEEIKSQFEGFVKDIMLNKEETKK--------DEDP
HUMAN     61  EDFVFMKTIQRCNTGERSLSLLNCEEIKSQFEGFVKDIMLNKEETKKENSFEMQKGDQNP
              **********************************************        *  *

ISF31,   112  QIAAHVVSEANSNAASVLQWAKKGYYTMKSNLVTLENGKQLTVKRQGLYYIYAQVTFCSN
HUMAN    121  QIAAHVISEASSKTTSVLQWAEKGYYTMSNNLVTLENGKQLTVKRQGLYYIYAQVTFCSN
              ****** *** *  ****** ******* **************************

ISF31,   172  REPSSQRPFIVGLWLKPSSGSERILLKAANTHSSSQLCEQQSVHLGGVFELQPGASVFVN
HUMAN    181  REASSQAPFIASLCLKSPGRFERILLRAANTHSSAKPCGQQSIHLGGVFELQPGASVFVN
              ** *** ***  *  **     ****** ******    **** *  ************

ISF31,   232  VTDPSQVSHGTGFTSFGLLKL
HUMAN    241  VTDPSQVSHGTGFTSFGLLKL
              *********************

84.2% identity in 260 residues overlap; Score: 1082.0; Gap frequency: 3.1%

ISF31,     1  MIETYNQTSPRSAATGLPISMKIFMYLLTVFLITQMIGSALFAVYLHRRLDKIEDERNLH
MURINE     1  MIETYSQPSPRSVATGLPASMKIFMYLLTVFLITQMIGSVLFAVYLHRRLDKVEEEVNLH
              ***** * **** ***** ******************* ************ *  * ***

ISF31,    61  EDFVFMKTIQRCNTGERSLSLLNCEEIKSQFEGFVKDIMLNKEETKK--------DEDPQ
MURINE    61  EDFVFIKKLKRCNKGEGSLSLLNCEEMRRQFEDLVKDITLNKEEKKENSFEMQRGDEDPQ
              ***** *   *** **  ********   *** **** *****  *         *****

ISF31,   113  IAAHVVSEANSNAASVLQWAKKGYYTMKSNLVTLENGKQLTVKRQGLYYIYAQVTFCSNR
MURINE   121  IAAHVVSEANSNAASVLQWAKKGYYTMKSNLVMLENGKQLTVKREGLYYVYTQVTFCSNR
              ********************************  ********** ****  * ********

ISF31,   173  EPSSQRPFIVGLWLKPSSGSERILLKAANTHSSSQLCEQQSVHLGGVFELQPGASVFVNV
MURINE   181  EPSSQRPFIVGLWLKPSSGSERILLKAANTHSSSQLCEQQSVHLGGVFELQAGASVFVNV
              **************************************************  ********

ISF31,   233  TDPSQVSHGTGFTSFGLLKL
MURINE   241  TEASQVIHRVGFSSFGLLKL
              *  *** *  ** *******
```

Fig. 30:   ISF33 Amino Acid Sequence Alignment to Human and Mouse CD154

87.4% identity in 261 residues overlap; Score: 1118.0; Gap frequency: 3.4%

```
ISF33,      1 MIETYNQTSPRSAATGLPISMKIFMYLLTVFLITQMIGSALFAVYLHRRLDKIEDERNLH
HUMAN       1 MIETYNQTSPRSAATGLPISMKIFMYLLTVFLITQMIGSALFAVYLHRRLDKIEDERNLH
              ************************************************************

ISF33,     61 EDFVFMKTIQRCNTGERSLSLLNCEEIKSQFEGFVKDIMLNKEETKK--------DEDP
HUMAN      61 EDFVFMKTIQRCNTGERSLSLLNCEEIKSQFEGFVKDIMLNKEETKKENSFEMQKGDQNP
              **********************************************        * *

ISF33,    112 QIAAHVVSEANSNAASVLQWAKKGYYTMKSNLVTLENGKQLTVKRQGLYYIYAQVTFCSN
HUMAN     121 QIAAHVISEASSKTTSVLQWAEKGYYTMSNNLVTLENGKQLTVKRQGLYYIYAQVTFCSN
              ****** *** *     ****** ****** *****************************

ISF33,    172 REASSQAPFIVGLWLKPSSGSERILLKAANTHSSSQLCEQQSVHLGGVFELQPGASVFVN
HUMAN     181 REASSQAPFIASLCLKSPGRFERILLRAANTHSSAKPCGQQSIHLGGVFELQPGASVFVN
              **********  * **     ***** ******    * *** *****************

ISF33,    232 VTDPSQVSHGTGFTSFGLLKL
HUMAN     241 VTDPSQVSHGTGFTSFGLLKL
              *********************
```

83.5% identity in 260 residues overlap; Score: 1068.0; Gap frequency: 3.1%

```
ISF33,      1 MIETYNQTSPRSAATGLPISMKIFMYLLTVFLITQMIGSALFAVYLHRRLDKIEDERNLH
MURINE      1 MIETYSQPSPRSVATGLPASMKIFMYLLTVFLITQMIGSVLFAVYLHRRLDKVEEEVNLH
              ***** * **** ***** ******************* ************ *  * ***

ISF33,     61 EDFVFMKTIQRCNTGERSLSLLNCEEIKSQFEGFVKDIMLNKEETKK--------DEDPQ
MURINE     61 EDFVFIKKLKRCNKGEGSLSLLNCEEMRRQFEDLVKDITLNKEEKKENSFEMQRGDEDPQ
              ***** *   *** **  ********   ***  **** *****  *         *****

ISF33,    113 IAAHVVSEANSNAASVLQWAKKGYYTMKSNLVTLENGKQLTVKRQGLYYIYAQVTFCSNR
MURINE    121 IAAHVVSEANSNAASVLQWAKKGYYTMKSNLVMLENGKQLTVKREGLYYVYTQVTFCSNR
              ******************************** *********** **** * *******

ISF33,    173 EASSQAPFIVGLWLKPSSGSERILLKAANTHSSSQLCEQQSVHLGGVFELQPGASVFVNV
MURINE    181 EPSSQRPFIVGLWLKPSSGSERILLKAANTHSSSQLCEQQSVHLGGVFELQAGASVFVNV
              * ***  ******************************************** ********

ISF33,    233 TDPSQVSHGTGFTSFGLLKL
MURINE    241 TEASQVIHRVGFSSFGLLKL
              *  ***  * ** *******
```

Fig. 31: ISF35 Amino Acid Sequence Alignment to Human and Mouse CD154

87.7% identity in 261 residues overlap; Score: 1119.0; Gap frequency: 3.4%

```
ISF35,     1 MIETYNQTSPRSAATGLPISMKIFMYLLTVFLITQMIGSALFAVYLHRRLDKIEDERNLH
HUMAN      1 MIETYNQTSPRSAATGLPISMKIFMYLLTVFLITQMIGSALFAVYLHRRLDKIEDERNLH
             ************************************************************

ISF35,    61 EDFVFMKTIQRCNTGERSLSLLNCEEIKSQFEGFVKDIMLNKEETKK--------DEDP
HUMAN     61 EDFVFMKTIQRCNTGERSLSLLNCEEIKSQFEGFVKDIMLNKEETKKENSFEMQKGDQNP
             **********************************************        *  *

ISF35,   112 QIAAHVVSEANSNAASVLQWAKKGYYTMKSNLVTLENGKQLTVKRQGLYYIYAQVTFCSN
HUMAN    121 QIAAHVISEASSKTTSVLQWAEKGYYTMSNNLVTLENGKQLTVKRQGLYYIYAQVTFCSN
             ******  ***  *      ******  * *  **************************

ISF35,   172 REASSQAPFIVGLWLKPSSGSERILLKAANTHSSSQLCEQQSIHLGGVFELQPGASVFVN
HUMAN    181 REASSQAPFIASLCLKSPGRFERILLRAANTHSSAKPCGQQSIHLGGVFELQPGASVFVN
             **********  *  **     *****  *****       *******************

ISF35,   232 VTDPSQVSHGTGFTSFGLLKL
HUMAN    241 VTDPSQVSHGTGFTSFGLLKL
             *********************
```

83.1% identity in 260 residues overlap; Score: 1067.0; Gap frequency: 3.1%

```
ISF35,     1 MIETYNQTSPRSAATGLPISMKIFMYLLTVFLITQMIGSALFAVYLHRRLDKIEDERNLH
MURINE     1 MIETYSQPSPRSVATGLPASMKIFMYLLTVFLITQMIGSVLFAVYLHRRLDKVEEEVNLH
             *****  *    ****  *  ********************  ********* * * ***

ISF35,    61 EDFVFMKTIQRCNTGERSLSLLNCEEIKSQFEGFVKDIMLNKEETKK--------DEDPQ
MURINE    61 EDFVFIKKLKRCNKGEGSLSLLNCEEMRRQFEDLVKDITLNKEEKKENSFEMQRGDEDPQ
             *****  *   ** ** ********   **   ****  ****  *         *****

ISF35,   113 IAAHVVSEANSNAASVLQWAKKGYYTMKSNLVTLENGKQLTVKRQGLYYIYAQVTFCSNR
MURINE   121 IAAHVVSEANSNAASVLQWAKKGYYTMKSNLVMLENGKQLTVKREGLYYVYTQVTFCSNR
             ********************************  ***********  ****  * *******

ISF35,   173 EASSQAPFIVGLWLKPSSGSERILLKAANTHSSSQLCEQQSIHLGGVFELQPGASVFVNV
MURINE   181 EPSSQRPFIVGLWLKPSSGSERILLKAANTHSSSQLCEQQSVHLGGVFELQAGASVFVNV
             * ***  ****************************************  *******  *******

ISF35,   233 TDPSQVSHGTGFTSFGLLKL
MURINE   241 TEASQVIHRVGFSSFGLLKL
             * ***  *  ** *******
```

Fig. 32: ISF37 Amino Acid Sequence Alignment to Human and Mouse CD154

89.3% identity in 261 residues overlap; Score: 1144.0; Gap frequency: 3.4%

```
ISF37,     1 MIETYNQTSPRSAATGLPISMKIFMYLLTVFLITQMIGSALFAVYLHRRLDKIEDERNLH
HUMAN      1 MIETYNQTSPRSAATGLPISMKIFMYLLTVFLITQMIGSALFAVYLHRRLDKIEDERNLH
             ************************************************************

ISF37,    61 EDFVFMKTIQRCNTGERSLSLLNCEEIKSQFEGFVKDIMLNKEETKK--------DEDP
HUMAN     61 EDFVFMKTIQRCNTGERSLSLLNCEEIKSQFEGFVKDIMLNKEETKKENSFEMQKGDQNP
             **********************************************        *  *

ISF37,   112 QIAAHVVSEANSNAASVLQWAKKGYYTMKSNLVTLENGKQLTVKRQGLYYIYAQVTFCSN
HUMAN    121 QIAAHVISEASSKTTSVLQWAEKGYYTMSNNLVTLENGKQLTVKRQGLYYIYAQVTFCSN
             ****** *** *      ****** ****  ****************************

ISF37,   172 REASSQAPFIVGLWLKPSSGSERILLKAANTHSSAKPCGQQSIHLGGVFELQPGASVFVN
HUMAN    181 REASSQAPFIASLCLKSPGRFERILLRAANTHSSAKPCGQQSIHLGGVFELQPGASVFVN
             **********  * **     ***** *********************************

ISF37,   232 VTDPSQVSHGTGFTSFGLLKL
HUMAN    241 VTDPSQVSHGTGFTSFGLLKL
             *********************
```

81.5% identity in 260 residues overlap; Score: 1046.0; Gap frequency: 3.1%

```
ISF37,     1 MIETYNQTSPRSAATGLPISMKIFMYLLTVFLITQMIGSALFAVYLHRRLDKIEDERNLH
MURINE     1 MIETYSQPSPRSVATGLPASMKIFMYLLTVFLITQMIGSVLFAVYLHRRLDKVEEEVNLH
             *****  *  * ****** ********************** ************  *  ***

ISF37,    61 EDFVFMKTIQRCNTGERSLSLLNCEEIKSQFEGFVKDIMLNKEETKK--------DEDPQ
MURINE    61 EDFVFIKKLKRCNKGEGSLSLLNCEEMRRQFEDLVKDITLNKEEKKENSFEMQRGDEDPQ
             *****  *** ** ********    ***  **** *****  *         *****

ISF37,   113 IAAHVVSEANSNAASVLQWAKKGYYTMKSNLVTLENGKQLTVKRQGLYYIYAQVTFCSNR
MURINE   121 IAAHVVSEANSNAASVLQWAKKGYYTMKSNLVMLENGKQLTVKREGLYYVYTQVTFCSNR
             ********************************  ********** **** ** * *******

ISF37,   173 EASSQAPFIVGLWLKPSSGSERILLKAANTHSSAKPCGQQSIHLGGVFELQPGASVFVNV
MURINE   181 EPSSQRPFIVGLWLKPSSGSERILLKAANTHSSSQLCEQQSVHLGGVFELQAGASVFVNV
             * ***  **************************    *  *** ********** *********

ISF37,   233 TDPSQVSHGTGFTSFGLLKL
MURINE   241 TEASQVIHRVGFSSFGLLKL
             *  ***  *  **  *******
```

Fig. 33: ISF39 Amino Acid Sequence Alignment to Human and Mouse CD154

87.0% identity in 261 residues overlap; Score: 1109.0; Gap frequency: 3.4%

```
ISF39,      1 MIETYNQTSPRSAATGLPISMKIFMYLLTVFLITQMIGSALFAVYLHRRLDKIEDERNLH
HUMAN       1 MIETYNQTSPRSAATGLPISMKIFMYLLTVFLITQMIGSALFAVYLHRRLDKIEDERNLH
              ************************************************************

ISF39,     61 EDFVFMKTIQRCNTGERSLSLLNCEEIKSQFEGFVKDIMLNKEETKK--------DEDP
HUMAN      61 EDFVFMKTIQRCNTGERSLSLLNCEEIKSQFEGFVKDIMLNKEETKKENSFEMQKGDQNP
              **********************************************        *  *

ISF39,    112 QIAAHVVSEANSNAASVLQWAKKGYYTMKSNLVTLENGKQLTVKRQGLYYIYAQVTFCSN
HUMAN     121 QIAAHVISEASSKTTSVLQWAEKGYYTMSNNLVTLENGKQLTVKRQGLYYIYAQVTFCSN
              ****** *** *      ****** **** * ****************************

ISF39,    172 REPSSQRPFIVGLWLKPSSGSERILLKAANTHSSSQLCEQQSIHLGGVFELQPGASVFVN
HUMAN     181 REASSQAPFIASLCLKSPGRFERILLRAANTHSSAKPCGQQSIHLGGVFELQPGASVFVN
              ** *** ***   *  * **    ***** ******    *  *****************

ISF39,    232 VTDPSQVSHGTGFTSFGLLKL
HUMAN     241 VTDPSQVSHGTGFTSFGLLKL
              *********************
```

83.8% identity in 260 residues overlap; Score: 1081.0; Gap frequency: 3.1%

```
ISF39,      1 MIETYNQTSPRSAATGLPISMKIFMYLLTVFLITQMIGSALFAVYLHRRLDKIEDERNLH
MURINE      1 MIETYSQPSPRSVATGLPASMKIFMYLLTVFLITQMIGSVLFAVYLHRRLDKVEEEVNLH
              *****  * ****  *****  ********************** ***********  * ***

ISF39,     61 EDFVFMKTIQRCNTGERSLSLLNCEEIKSQFEGFVKDIMLNKEETKK-------DEDPQ
MURINE     61 EDFVFIKKLKRCNKGEGSLSLLNCEEMRRQFEDLVKDITLNKEEKKENSFEMQRGDEDPQ
              *****  *   ** ** ********   *** * **** *****   *        *****

ISF39,    113 IAAHVVSEANSNAASVLQWAKKGYYTMKSNLVTLENGKQLTVKRQGLYYIYAQVTFCSNR
MURINE    121 IAAHVVSEANSNAASVLQWAKKGYYTMKSNLVMLENGKQLTVKREGLYYVYTQVTFCSNR
              ******************************** ********** **** * *********

ISF39,    173 EPSSQRPFIVGLWLKPSSGSERILLKAANTHSSSQLCEQQSIHLGGVFELQPGASVFVNV
MURINE    181 EPSSQRPFIVGLWLKPSSGSERILLKAANTHSSSQLCEQQSVHLGGVFELQAGASVFVNV
              **************************************** *********** ********

ISF39,    233 TDPSQVSHGTGFTSFGLLKL
MURINE    241 TEASQVIHRVGFSSFGLLKL
              *  ***  *  ** ******
```

Fig. 34:    ISF41 Amino Acid Sequence Alignment to Human and Mouse CD154

88.5% identity in 261 residues overlap; Score: 1134.0; Gap frequency: 3.4%

```
ISF41,      1  MIETYNQTSPRSAATGLPISMKIFMYLLTVFLITQMIGSALFAVYLHRRLDKIEDERNLH
HUMAN       1  MIETYNQTSPRSAATGLPISMKIFMYLLTVFLITQMIGSALFAVYLHRRLDKIEDERNLH
               ************************************************************

ISF41,     61  EDFVFMKTIQRCNTGERSLSLLNCEEIKSQFEGFVKDIMLNKEETKK--------DEDP
HUMAN      61  EDFVFMKTIQRCNTGERSLSLLNCEEIKSQFEGFVKDIMLNKEETKKENSFEMQKGDQNP
               **********************************************        *  *

ISF41,    112  QIAAHVVSEANSNAASVLQWAKKGYYTMKSNLVTLENGKQLTVKRQGLYYIYAQVTFCSN
HUMAN     121  QIAAHVISEASSKTTSVLQWAEKGYYTMSNNLVTLENGKQLTVKRQGLYYIYAQVTFCSN
               ****** *** *      ****** ******* ******************************

ISF41,    172  REPSSQRPFIVGLWLKPSSGSERILLKAANTHSSAKPCGQQSIHLGGVFELQPGASVFVN
HUMAN     181  REASSQAPFIASLCLKSPGRFERILLRAANTHSSAKPCGQQSIHLGGVFELQPGASVFVN
               ** *** ***  *  **     ***** ************************************

ISF41,    232  VTDPSQVSHGTGFTSFGLLKL
HUMAN     241  VTDPSQVSHGTGFTSFGLLKL
               *********************
```

82.3% identity in 260 residues overlap; Score: 1060.0; Gap frequency: 3.1%

```
ISF41,      1  MIETYNQTSPRSAATGLPISMKIFMYLLTVFLITQMIGSALFAVYLHRRLDKIEDERNLH
MURINE      1  MIETYSQPSPRSVATGLPASMKIFMYLLTVFLITQMIGSVLFAVYLHRRLDKVEEEVNLH
               *****  * **** ***** ******************* ************ *  ***

ISF41,     61  EDFVFMKTIQRCNTGERSLSLLNCEEIKSQFEGFVKDIMLNKEETKK--------DEDPQ
MURINE     61  EDFVFIKKLKRCNKGEGSLSLLNCEEMRRQFEDLVKDITLNKEEKKENSFEMQRGDEDPQ
               *****  *   ** **  ********   **  ****  *****  *        *****

ISF41,    113  IAAHVVSEANSNAASVLQWAKKGYYTMKSNLVTLENGKQLTVKRQGLYYIYAQVTFCSNR
MURINE    121  IAAHVVSEANSNAASVLQWAKKGYYTMKSNLVMLENGKQLTVKREGLYYVYTQVTFCSNR
               ********************************  *********** **** * *******

ISF41,    173  EPSSQRPFIVGLWLKPSSGSERILLKAANTHSSAKPCGQQSIHLGGVFELQPGASVFVNV
MURINE    181  EPSSQRPFIVGLWLKPSSGSERILLKAANTHSSSQLCEQQSVHLGGVFELQAGASVFVNV
               *********************************  *** ********** *********

ISF41,    233  TDPSQVSHGTGFTSFGLLKL
MURINE    241  TEASQVIHRVGFSSFGLLKL
               *  ***  *  ** ******
```

NUCLEIC ACIDS ENCODING CHIMERIC CD154 POLYPEPTIDES

CROSS REFERENCE TO RELATED APPLICATIONS

This application is a divisional application of U.S. application Ser. No. 10/154,759 filed May 23, 2002, now issued as U.S. Pat. No. 7,495,090. The disclosure of each of the prior applications is considered part of and is incorporated by reference in the disclosure of this application.

BACKGROUND OF THE INVENTION

1. Field of the Invention

The present invention relates to the fields of biochemistry, immunology, genetic engineering, and medicine. In particular, it relates to novel chimeric ligands that, when expressed on the surface of a cell, are more stable than the corresponding native ligand but retain the receptor-binding function of the native ligand and are not immunogenic.

2. Background Information

The immune system eliminates malignant cells by recognizing them as foreign and then clearing them from the body. To accomplish this, the immune system invokes both an antibody response and a cellular response. Both these responses require interaction among a number of different cells of the immune system (Abbas, Cellular and Molecular Immunology, 2000).

An immune reaction typically begins with a T lymphocyte (T cell) that has on its surface a T cell receptor (TCR) that binds to an antigen derived peptide associated with a class II major histo-compatibility complex (MHC) molecule. The T cell also expresses on its surface various polypeptides, which are referred to as "ligands" because they bind to receptors on cells associated with an immune-mediated response, as described in more detail below. When the T cell receptor binds to a MHC-associated antigen, such as antigen derived from a malignant cell, it becomes activated and expresses a ligand on its surface. The ligand is only present on the cell surface for a short time, and once it has been removed from the surface of the cell, the T cell's ability to bind a receptor-bearing cell is lost. One such ligand is called CD154.

CD154 is one member of a larger family of ligands, collectively referred to as the TNF superfamily (Gruss et al, Cytokines Mol Ther, 1:75-105, 1995 and Locksley et al, Cell, 104:487-501, 2001). Members of the TNF superfamily include Fas ligand ("FasL"), TNFα, LTα, lymphotoxin (TNFβ) CD154, TRAIL, CD70, CD30 ligand, 4-1BB ligand, APRIL, TWEAK, RANK ligand, LIGHT, AITR ligand, ectodysplasin, BLYS, VEGI, and OX40 ligand. TNF superfamily members share a conserved secondary structure comprising four domains: domain I, the intracellular domain; domain II, which spans the cell membrane and is known as the transmembrane domain; domain III, which consists of the extracellular amino acids closest to the cell membrane; and domain IV, the distal extracellular domain (Kipps et al., WO98/26061 published Jun. 18, 1998). Typically, at least a part of domain IV can be cleaved from the parent molecule. The cleaved fragment often exhibits the same biological activity of the intact ligand and is conventionally referred to as a "soluble form" of the TNF family member.

I) Biological Activity of CD154

The interactions between CD154 (also known as CD40 ligand) and its cognate receptor, CD40, are critical for immune recognition. (Banchereau J. et al., *Annu. Rev. Immunol.* 12:881-922, 1994; Laman J. D. et al., *Crit. Rev. Immunol.*, 16:59-108, 1996). CD154 is transiently expressed on CD4$^+$ T cells following T cell receptor engagement by antigen presenting cells through MHC class II molecules. (Roy M. et al., *J. Immunol.*, 151:2497-2510, 1993; Hepmann P. et al., *Eur. J. Immunol.*, 23:961-964, 1993; Castle B. E. et al., *J. Immunol.*, 151:1777-1788, 1993; Cantwell M. et al., *Nat. Med.*, 3:984-989, 1997). This, in turn, can cause activation of CD40-expressing antigen presenting cells (APCs), including B cells, dendritic cells, monocytes, and macrophages. (Ranheim E. A. et al., *J. Exp. Med.*, 177:925-935, 1993; Ranheim E. A. et al., *Cell. Immunol.*, 161:226-235, 1995). Such CD40 activated cells can set off a cascade of immune-activating events that lead to a specific and effective immune response against foreign antigens, such as viruses or tumors. The importance of interactions between CD40 and CD154 is underscored by the finding that individuals who have inherited defects in the ligand for CD40 have profound immune deficiency. (Korthauer J. et al., *Nature*, 361:539-541, 1993; Aruffo A. et al., *Cell.*, 72:291-300, 1993). Such patients have an immune deficiency syndrome associated with impaired germinal center formation, defective isotype switching, and marked susceptibility to various bacterial and viral pathogens.

Because CD154 is such a critical molecule in immune regulation, several mechanisms control human CD154 expression. First, membrane-expressed CD154 can be cleaved and an extracellular portion of CD154 capable of binding the CD154 receptor, CD40, is released as a soluble molecule. Proteolytic cleavage enzymes have been shown to cleave human CD154 at different sites along the ligand, and release a soluble form of CD154 that is capable of binding to CD40 and stimulating an immune response. (Pietravalle F. et al., *J. Biol. Chem.*, 271:5965-5967, 1996; Pietravalle F. et al., *Eur. J. Immunol.*, 26:725-728, 1996). For instance, one study has shown that CD154 is cleaved between Phe 111 and Ala 123 (Pietravalle F. et al., *Eur. J. Immunol.*, 26:725-728, 1996), and cleavage has also been reported at Met 113. Second, CD154 interaction with its cognate receptor can induce rapid downmodulation of CD154 surface expression. (Cantwell M. et al., *Nat. Med.*, 3:984-989, 1997). Third, CD154 gene transcription is tightly regulated with maximum ligand expression 4 to 6 hours after TCR ligation followed by rapid decreases in CD154 RNA and protein synthesis. (Id.) Together, these regulatory mechanisms ensure specificity of an immune response to a specific antigen. The importance of maintaining tight control of CD154 expression is illustrated in individuals with systemic lupus erythematosus (SLE). These patients appear to hyper express CD154 as well as possess elevated levels of soluble CD154 in their plasma, suggesting uncontrolled CD154 expression contributes to SLE disease activity. (Kato K. et al., *J. Clin. Invest.*, 101:1133-1141, 1998; Vakkalanka R. K., *Arthritis Rheum.*, 42:871-881, 1999).

The potential for using CD154 for immunotherapy is under active investigation. Because CD154 is a potent immune activator, CD154 as a cancer therapy is a main focus of research because neoplastic cells are generally poor presenters of antigen and unable to stimulate vigorous anti-tumor responses. For example, chronic lymphocytic leukemia (CLL) B cells modified to express CD154 using a replication defective adenovirus vector can enhance CLL antigen presentation and induce autologous T cell cytotoxicity towards nonmodified CLL B cells. (Kato K. et al., *J. Clin. Invest.*, 101:1133-1141, 1998). Moreover, a phase-I clinical study using Ad-CD154 modified CLL B cells showed promising therapeutic results. (Wierda W. G. et al., *Blood*, 96:2917-2924, 2000). Similarly, other studies showed that modification of a range of tumor types to express CD154 can induce effective anti-tumor immune responses in animal models.

Studies manipulating B cells and other tumors work by either enhancing the antigen presentation of the neoplastic cell itself, as is the case for CLL and B cell lymphoma, or by activating bystander antigen presenting cells, such as dendritic cells that can initiate an anti-tumor immune response, as is the case for CD40-negative tumors. However, additional studies also suggest CD154 might have a direct growth-inhibitory effect on certain tumors, especially carcinomas of the breast. (Tong A. W. et al., *Clin. Cancer Des.*, 7:691-703, 2001; Hirano A., *Blood*, 93:2999-3007, 1999). In addition, there is evidence that growth of some types of lymphoma can be directly inhibited by CD40 ligation. (Wilsey J. A. et al., *J. Immunol.*, 158:2932-2938, 1997). As such, a wide range of tumors should be amenable to CD154 immunotherapy.

II) Drawbacks of Current CD154 Constructs

Although CD154 is a potentially powerful therapeutic, the form of CD154 used in clinical therapies will likely have a major impact on both safety and efficacy.

For example, recombinant soluble CD154 (rsCD154) composed only of the extracellular, receptor-binding domain of CD154 is functional. (Armitage R. J., *Eur. J. Immunol.*, 23:2326-2331, 1993; Lane P., *J. Exp. Med.*, 177:1209-1213, 1993). However rsCD154 is not as effective as native CD154 expressed on the cell membrane to induce CD40 signaling because optimal signaling requires multimerization of the CD40 receptors at the cell surface. (Schwabe R. F. et al., *Hybridoma*, 16:217-226, 1997). As a result, ligand-multimerization domains have been engineered, such as leucine zippers or CD8 domains, onto the n-terminal domain of rsCD154 to enhance receptor signaling. (Lans P., et al., *J. Exp. Med.* 177:1209-1213, 1993; Morris A. E., *J. Biol. Chem.* 274:418-423, 1999). Likewise, soluble CD154 is not optimal for cross-linking CD40 since it does not provide as strong a stimulation of antigen-presenting cells compared to membrane-expressed CD154.

In addition, soluble reagents that mediate CD40 signaling can trigger adverse physiological effects. For example, mice injected with soluble CD154-CD8 fusion protein developed pulmonary inflammation. (Wiley J. A. et al., *J. Immunol.*, 158:2932-2938, 1997). Likewise, administration of CD40-activating monoclonal antibody to immunocompromised mice induced intestinal lesions that were fatal. (Hixon J. A. et al., *Biol. Blood Marrow Transplant.*, 7:136-143, 2001) The toxicity associated with systemic administration of soluble CD154 appears to be a general feature of the TNF family since adverse effects are also seen following administration of soluble TNF-α, FasL, and TRAIL.

Another drawback of soluble CD154 is the short half-life of soluble TNF family members following systemic administration. (Spriss D. R. et al., *Ciba Found. Symp.*, 131:206-227, 1987; Funahashi I. et al., *Br. J. Cancer*, 67:447-455). This short half-life would require delivery of either higher doses of rsCD154 or continuous infusion over time, which not only increases the chances of toxicity but also would require isolation of large amounts of rsCD154 protein, a difficult and time-consuming process.

Due to the inherent problems using soluble CD154, membrane-expressed full-length human CD154 seems the better alternative. However, native human CD154 also possesses characteristics that might limit its efficacy or safety. As previously mentioned, full-length CD154 is cleaved and released as a soluble molecule, potentially allowing for similar toxicities described for rsCD154. In addition, proteolytic cleavage of membrane bound CD154 might decrease its functional activity. Although deletion of putative cleavage sites from CD154 can decrease its metabolism, this does not completely eliminate CD154 processing since multiple proteolytic cleavage sites exist. (Mazzei G. J. et al., *J. Biol. Chem.*, 270:7025-7028, 1995; Pistravalle F. et al., *J. Biol. Chem.*, 271:5965-5967, 1996). Moreover, a less apparent problem associated with using full-length human CD154 is its cell-type specific expression. For example, certain cell types, especially cells of B-cell origin, preclude expression of human CD154. (Kato K. et al., *J. Clin. Invest.*, 101:1133-1141, 1998; Cantwell M. et al., *Nat. Med.*, 3:984-989, 1997).

Interestingly, murine CD154 (mCD154) appears more advantageous than either native human CD154 or rsCD154 for therapeutic uses. Murine CD154 is relatively resistant to proteolytic cleavage in comparison to human CD154. Moreover, mCD154 is expressed by most cell types, including cells of B-cell origin that preclude human CD154 expression, often referred to as $CD40^+$ cells. (Id.) As such, mCD154 was expressed in the clinical trial of CD154 gene therapy of one type of $CD40^+$ cell, a CLL cell. (Wierda W. G., *Blood*, 96:2917-2924 (2000).

Still, mCD154 use in humans presents its own problems. For example, following repeated injections of Ad-CD154 modified CLL cells to patients, the reduction in leukemic cells decreased with each subsequent injection. Three of four CLL patients became refractory to the activity of mCD154-expressing cells by the fifth repeat injection. This loss of activity is likely due to the development of antibodies against the murine CD154 molecule making further treatments impossible. Assays to determine the formation of binding and neutralizing antibodies against CD154 showed anti-murine CD154 antibodies developed by the third repeat injection of Ad-mCD154 transduced CLL cells. In addition, the anti-CD154 antibodies could also neutralize murine CD154 function. Thus, despite the overall safety, expression stability, and short-term efficacy of mCD154, long-term repeated administration of mCD154 in humans will be difficult.

Given the disadvantages of current CD154 constructs, there is clearly a need for a preferred CD154 construct for disease therapy that possesses properties found in both human CD154 and murine CD154. A preferred CD154 construct would be expressed on diverse cell types, including lymphoid cells of B-cell origin. In addition, the CD154 construct would be membrane-stabilized and resistant to proteolytic cleavage, and thereby less likely to generate the soluble form of CD154. However, the preferred CD154 construct would maintain the receptor-binding function of native CD154. Both these properties are found in mCD154. Moreover, a preferred CD154 construct would not be immunogenic at the domain critical for receptor binding following administration in humans, thus avoiding functional neutralization. The present invention provides for such a CD154 construct.

SUMMARY OF THE INVENTION

The present invention relates to novel chimeric CD154 polypeptides having the most advantageous properties of human CD154 and murine CD154 and, as such, are safe and effective for disease therapy. Specifically, the chimeric CD154 would be capable of expression on diverse cell types, including B cells. It would be less resistant to proteolytic cleavage and thus more stable when expressed on cellular membranes. In addition, the chimeric CD154 would not be immunogenic and thus would not be neutralized by anti-CD154 antibodies. Finally, it would maintain the receptor-binding capabilities of human CD154, and thus elicit the same type of immunological response in humans.

These novel chimeric CD154 polypeptides are chimeric in that they are comprised of CD154 domains or subdomains from at least two different species, preferably human and mouse CD154. These polypeptides have been designated "immune stimulatory factors", or ISF's, because they combine human and non-human CD154 regions to maximize stimulation of the immune response. Specifically, at least one domain or subdomain of CD154 that contains a cleavage site of human CD154 is replaced with a corresponding domain or subdomain of non-human CD154, preferably murine CD154. In addition, the chimeric polypeptide is composed of a domain or subdomain of human CD154 that is responsible for binding a CD154 receptor. The present invention also relates to novel polynucleotide sequences encoding chimeric CD154, expression vectors comprising the novel polynucleotide sequences, and methods of producing the chimeric CD154. Finally, the present invention relates to methods of using the expression vectors to improve the immunoreactivity of transfected cells and to treat neoplasia.

Thus, one aspect of this invention relates to an isolated polynucleotide sequence encoding a chimeric CD154, comprising a first nucleotide sequence encoding an extracellular subdomain of non-human CD154 that replaces a cleavage site of human CD154, and a second nucleotide sequence encoding an extracellular subdomain of human CD154 that binds to a human CD154 receptor.

An aspect of this invention is the above isolated polynucleotide sequence, wherein the first nucleotide sequence further encodes an extracellular subdomain of non-human CD154 that is critical for expression of said CD154 by cells.

An aspect of this invention is the above isolated polynucleotide sequence, wherein the expressing cells are human CD40+ cells.

An aspect of this invention is the above isolated polynucleotide sequence, wherein the expressing cells are human CLL cells.

An aspect of this invention is the above isolated polynucleotide sequence such as those described above, wherein the first nucleotide sequence additionally encodes an extracellular domain that is useful in detecting the expression of the ligand encoded by the polynucleotide sequence because it binds to anti-murine CD154 antibodies.

An aspect of this invention is the above isolated polynucleotide sequence such as those described above, wherein the first nucleotide sequence encodes a subdomain of domain IV of non-human CD154.

An aspect of this invention is the above isolated polynucleotide sequence such as those described above, wherein the first nucleotide sequence encodes domain III, or a subdomain of domain III, of non-human CD154.

An aspect of this invention is the above isolated polynucleotide sequence, wherein the first nucleotide sequence encodes a subdomain of domain III that replaces a portion of a cleavage site of human CD154.

An aspect of this invention is the above isolated polynucleotide sequence such as those described above, wherein the first nucleotide sequence further encodes domain II, or a subdomain of domain II, of non-human CD154.

An aspect of this invention is the above isolated polynucleotide sequence such as those described above, wherein the first nucleotide sequence further encodes domain I, or a subdomain of domain I, of non-human CD154.

An aspect of this invention is the above isolated polynucleotide sequence such as those described above, wherein the first nucleotide sequence further encodes domains I, II and III of non-human CD154.

An aspect of this invention is the above isolated polynucleotide sequence such as those described above, wherein the non-human CD154 is murine CD154.

An aspect of this invention is the above isolated polynucleotide sequence such as those described above, wherein the second nucleotide sequence further encodes an extracellular subdomain of human CD154 that replaces a region to which functionally inhibitory anti-CD154 antibodies bind.

An aspect of this invention is the above isolated polynucleotide sequence such as those described above, wherein the second nucleotide sequence encodes a subdomain of domain IV of human CD154.

An aspect of this invention is the above isolated polynucleotide sequence such as those described above, wherein the sequence is selected from the group consisting of SEQ. ID. NOS. 1, 2, 3, 4, 5, 6, 7, 8, 9, 10, 11 and 12.

An aspect of this invention is the above isolated polynucleotide sequence such as those described above, wherein the sequence encodes an amino acid sequence selected from the group consisting of SEQ. ID. NOS. 13, 14, 15, 16, 17, 18, 19, 20, 21, 22, 23 and 24.

An aspect of this invention is a chimeric CD154 comprising a first subdomain of non-human CD154, wherein the subdomain replaces a cleavage site of human CD154, and a second subdomain of human CD154 that binds to a CD154 receptor.

An aspect of this invention is the above chimeric CD154 that is less susceptible to cleavage from the surface of cells than human CD154.

An aspect of this invention is the above chimeric CD154, wherein the cleavage rate of the chimeric CD154 is at least 90% less than the cleavage rate of human CD154.

An aspect of this invention is the above chimeric CD154 such as those described above, wherein the first subdomain is critical for expression of the polypeptide by cells.

An aspect of this invention is the above chimeric CD154, wherein the expressing cells are human CD40+ cells.

An aspect of this invention is the above chimeric CD154, wherein the expressing cells are human CLL cells.

An aspect of this invention is the above chimeric CD154 such as those described above, wherein the first subdomain is useful in detecting the expression of the chimeric CD154 by binding to anti-murine CD154 antibodies.

An aspect of this invention is the above chimeric CD154 such as those described above that is not immunogenic and is thereby not neutralized by anti-CD154 antibodies.

An aspect of this invention is the above chimeric CD154 such as those described above, wherein the first subdomain comprises a subdomain of domain IV of non-human CD154.

An aspect of this invention is the above chimeric CD154 such as those described above, wherein the first subdomain further comprises domain III, or a subdomain or domain III, of non-human CD154.

An aspect of this invention is the above chimeric CD154, wherein the first subdomain replaces a portion of a cleavage site of human CD154.

An aspect of this invention is the above chimeric CD154 such as those described above, wherein the first subdomain further comprises domain II, or a subdomain or domain II, of non-human CD154.

An aspect of this invention is the above chimeric CD154 such as those described above, wherein the first subdomain further comprises domain I, or a subdomain or domain I, of non-human CD154.

An aspect of this invention is the above chimeric CD154 such as those described above, wherein the first subdomain further comprises domains I, II and III of non-human CD154.

An aspect of this invention is the above chimeric CD154 such as those described above, wherein the non-human CD154 is murine CD154.

An aspect of this invention is the above chimeric CD154 such as those described above, wherein the second subdomain comprises a subdomain of domain IV of human CD154.

An aspect of this invention is an expression vector comprising one of the above isolated polynucleotide sequences.

An aspect of this invention is the above expression vector, wherein the polynucleotide sequence encodes a chimeric CD154 comprising a subdomain of domain IV murine CD154 that replaces a cleavage site of human CD154, and a subdomain of domain IV of human CD154 that binds to a CD154 receptor.

An aspect of this invention is an expression vector such as those described above, further comprising a polynucleotide sequence that encodes a subdomain of domain IV of murine CD154 that is critical for expression of murine CD154 in human cells.

An aspect of this invention is an expression vector such as those described above, further comprising a polynucleotide sequence that encodes domain III, or a subdomain of domain III, of murine CD154.

An aspect of this invention is an expression vector such as those described above, further comprising a polynucleotide sequence that encodes domain II, or a subdomain of domain II, of murine CD154.

An aspect of this invention is an expression vector such as those described above, further comprising a polynucleotide sequence that encodes domain I, or a subdomain of domain I, of murine CD154.

An aspect of this invention is an expression vector such as those described above, further comprising a polynucleotide sequence that encodes domains I, II and III of murine CD154.

An aspect of this invention is an expression vector such as those described above, comprising viral DNA or bacterial DNA.

An aspect of this invention is the above expression vector, wherein the viral DNA is selected from the group consisting of adenoviral CDA or retroviral DNA.

An aspect of this invention is the above expression vector, wherein at least a portion of the vector comprises adenoviral DNA.

An aspect of this invention is an expression vector such as those described above, further comprising a promoter region.

An aspect of this invention is the above expression vector, further comprising as polyadenylation signal region.

An aspect of this invention is a genetic construct comprising the above isolated polynucleotide sequence operatively linked to a promoter sequence and to a polyadenylation signal sequence.

An aspect of this invention is a host cell, comprising the above expression vector or the above genetic construct.

An aspect of this invention is the above host cell, wherein the cell is a mammalian cell.

An aspect of this invention is the above host cell, wherein the cell is a human cell.

An aspect of this invention is a host cell such as those described above, wherein the cell is a tumor cell.

An aspect of this invention is a host cell such as those described above, wherein the cell is an antigen presenting cell.

An aspect of this invention is a process for producing the above chimeric CD154, comprising culturing the above host cell under conditions suitable to effect expression of the protein.

An aspect of this invention is a method for increasing the concentration of a ligand capable of binding to a CD154 receptor on the surface of a cell, comprising introducing into the cell an isolated polynucleotide sequence encoding the above chimeric CD154, whereby the chimeric CD154 is less susceptible to cleavage from the surface of the cells than human CD154.

An aspect of this invention is the above method for increasing the concentration of a ligand capable of binding to a CD154 receptor on the surface of a cell, wherein the isolated polynucleotide sequence comprises the above expression vector or the above genetic construct.

An aspect of this invention is the above method for increasing the concentration of a ligand capable of binding to a CD154 receptor on the surface of a cell, wherein the cell expresses a CD154 receptor on its surface.

An aspect of this invention is a method for inducing activation of an immune system cell, comprising introducing into the cell an isolated polynucleotide sequence encoding the above chimeric CD154 so that it is expressed on the surface of the cell.

An aspect of this invention is a method for treating neoplasia in a patient comprising introducing into a neoplastic cell an isolated polynucleotide sequence encoding the above chimeric CD154 so that it is expressed on the surface of the cell.

An aspect of this invention is the above method for treating neoplasia in a patient, further comprising obtaining the neoplastic cell from a human patient, and infusing the neoplastic cell back into the patient after having introduced into the cells the above polynucleotide sequence encoding the chimeric CD154.

BRIEF DESCRIPTION OF THE DRAWINGS

FIG. 1 is a schematic diagram that shows exemplary polynucleotides encoding the chimeric CD154 of the present invention, and indicates the location of subdomains associated with specific properties of the chimeric CD154. The domains or subdomains derived from murine CD154 are shown shaded.

FIG. 2 is a series of fluorescent activated cell sorting (FACS) histograms showing the expression of exemplary chimeric CD154 polypeptides of the present invention, i.e., ISF 30-ISF 39, as compared to murine CD154 (mCD154) and a control plasmid pcDNA3 containing no CD154. Expression was measured following transfection of HeLa cells with pcDNA3 plasmids containing mCD154 and each ISF construct. The shaded area shows the expression of non-transfected HeLa cells and the unshaded area depicts the expression of transfected HeLa cells.

FIG. 3 is a series of FACS histograms showing the functional capacity of HeLa cells transfected with exemplary chimeric CD154 polypeptides of the present invention, i.e., ISF 30-ISF 39, as compared to murine CD154 (mCD154) and a control plasmid containing no CD154, to activate the expression of phenotypic surface markers CD70 and CD95 by Ramos B cells. The shaded area shows surface marker expression by non-activated cells, the unshaded area under the thin line depicts surface marker expression of B cells activated by HeLa cells that were transfected with control pcDNA3 plasmid, and the unshaded area under the bold line shows surface marker expression of B cells activated by HeLa cells that were transfected with mCD154 or an ISF construct.

FIG. 4 is a series of FACS histograms showing the sensitivity of exemplary chimeric CD154 polypeptides of the present invention, i.e., ISF 30-ISF 39, as compared to murine CD154 (mCD154) and human CD154 (hCD154), to binding by antibody in patient plasma capable of neutralizing native murine CD154 function. This sensitivity was measured by co-incubating Ramos B cells with HeLa cells transfected with a pcDNA3 plasmid containing mCD154 or one of the exemplary ISF constructs, adding plasma containing neutralizing antibody and, after about one day of incubation, harvesting and analyzing the Ramos cells for CD70 and CD95 surface marker expression. The shaded area shows surface marker expression is not activated because the Ramos cells were incubated with non-transfected HeLa cells, the unshaded area under the thin line shows the surface marker expression in cells that were incubated with antibody-containing plasma, and the shaded area under the bolded line shows surface marker expression in cells that were not incubated with plasma.

FIG. 5 is a series of FACS histograms that shows the sensitivity of selected chimeric CD154 polypeptides of the present invention, ISF 30 and ISF 35, as compared to murine CD154 (mCD154) and a control plasmid, to patient plasma antibodies capable of neutralizing CD154 function. This sensitivity was measured following transfection of HeLa cells with pcDNA3 plasmid containing mCD154, ISF 30 and ISF 35 and incubation of the transfected cells with patient plasma containing neutralizing antibodies. The shaded area shows the amount of antibodies bound to cells that were not incubated with plasma, and the unshaded area show the amount of antibodies bound to cells that were incubated with plasma.

FIG. 6 is a series of FACS histograms that shows the expression of selected chimeric CD154 polypeptides of the present invention, ISF 32 and 35, as compared to murine CD154 (m CD154), in HeLa cells infected with increasing multiplicity of infection (MOI) ratios of adenovirus vectors containing mCD154, ISF 32 and ISF 35. The shaded area shows the expression of non-transfected HeLa cells, and the unshaded area shows the expression of HeLa cells transfected with the above-described adenovirus vectors.

FIG. 7 is a series of FACS histograms that shows the expression by CLL B cells of selected CD154 polypeptides of the present invention, ISF 32 and 35, as compared to murine CD154 (mCD154) and non-infected cells, following infection with adenovirus vectors containing mCD154, ISF 32 and ISF 35. The shaded area shows the expression of non-transfected CLL B cells, and the unshaded area shows the expression of CLL B cells transfected with the above-described adenovirus vectors.

FIG. 8 is a series of FACS histograms that shows the activation of CLL B cells co-cultured with HeLa cells expressing selected CD154 polypeptides of the present invention, ISF 32 and 35, as compared to murine CD154 (mCD154). This activation was measured by changes in expression of phenotypic surface markers, CD80, CD70, CD86, CD95, CD54 and CD27, that are characteristic of CD40 activation. The shaded area shows surface marker expression of non-activated CLL B cells, the unshaded area under the thin line shows the activation of CLL B cells that were co-cultured with HeLa cells transfected with control adenovirus AD-LacZ containing no CD154, and the unshaded area under the bold line shows the activation of CLL B cells co-cultured with HeLa cells transfected with mCD154, ISF 23 and ISF 35.

FIG. 9 is a series of FACS histograms showing the expression of selected chimeric CD154 polypeptides of the present invention, ISF 5, ISF 12, ISF 24 and ISF 32, as compared to human and murine CD154 following transfection in HeLa cells and CLL B cells. The shaded area shows expression in non-transfected cells, and the unshaded area shows expression in cells transfected with each of the designated ISF constructs. This figure indicates that human and murine CD154, as well as the selected ISF constructs, are expressed in HeLa cells. However, this figure also confirms that CLL B cells typically precludes expression of human CD154, but not murine CD154. CLL B cells express two of the ISF constructs, i.e., ISF 5, that has a domain IV composed completely of murine CD154, and ISF 32, that has a domain IV which is comprised in large part of murine CD154. This indicates that the regulatory element allowing expression of murine CD154 in CLL B cells is localized to a region of domain IV. Accordingly, ISF 12 and ISF 24 were not well expressed by CLL B cells, because domain IV of ISF 12 is composed exclusively of human CD154, while domain IV of ISF 24 includes murine CD154, but also has a region of human CD154 that encompasses the region regulating expression of the molecule by CLL cells.

FIG. 10 is a bar graph plotting the quantity of soluble ligand generated two days after infection of HeLa cells with adenovirus bearing a selected chimeric CD154 polypeptide of the present invention, ISF 35, and human CD154. The quantity of soluble CD154 generated was detected using a human CD154-specific ELISA (enzyme linked immunosorbent assay) and was calculated based on titration of a known amount of soluble CD40 ligand-CD8 fusion protein in the ELISA. The graph shows the resistance of ISF 35 to cleavage into soluble ISF 35, as compared to cleavage of human CD154 into soluble CD154 and the absence of soluble CD154 generated by non-infected cells. ISF 35 is significantly more resistant to cleavage, generating no soluble ISF 35. In contrast, human CD154 is readily cleaved into soluble CD154 at levels >120 ng/ml.

FIG. 11(a) shows the nucleotide sequence of ISF 30 (SEQ. ID. NO. 1) aligned against human CD154. Regions homologous with human CD154 are indicated by bold type. FIG. 11(b) shows the nucleotide sequence of ISF 30 (SEQ. ID. NO. 1) aligned against murine CD154. In each figure, the ISF nucleotide sequence is the upper sequence in the alignment, while the nucleotide sequence for the human or mouse CD154 is the lower sequence. Alignments seen in this figure and remaining FIGS. 12(a), 12(b), 13(a), 13(b), 14(a), 14(b), 15(a), 15(b), 16(a), 16(b), 17(a), 17(b), 18(a), 18(b), 19(a), 19(b), 20(a), 20(b), 21(a), 21(b), 22(a) and 22(b) were calculated using the LALIGN program to find multiple matching subsegments in two sequences, which can be found on the internet at: ch.embnet.org/software/LALIGN form.html.

FIG. 12(a) shows the nucleotide sequence of ISF 32 (SEQ. ID. NO. 3) aligned against human CD154. Regions homologous with human CD154 are indicated by bold type. FIG. 12(b) shows the nucleotide sequence of ISF 32 (SEQ. ID. NO. 3) aligned against murine CD154. In each figure, the ISF nucleotide sequence is the upper sequence in the alignment, while the nucleotide sequence for the human or mouse CD154 is the lower sequence.

FIG. 13(a) shows the nucleotide sequence of ISF 34 (SEQ. ID. NO. 5) aligned against human CD154. Regions homologous with human CD154 are indicated by bold type. FIG. 13(b) shows the nucleotide sequence of ISF 34 (SEQ. ID. NO. 5) aligned against murine CD154. In each figure, the ISF nucleotide sequence is the upper sequence in the alignment, while the nucleotide sequence for the human or mouse CD154 is the lower sequence.

FIG. 14(a) shows the nucleotide sequence of ISF 36 (SEQ. ID. NO. 7) aligned against human CD154. Regions homologous with human CD154 are indicated by bold type. FIG. 14(b) shows the nucleotide sequence of ISF 36 (SEQ. ID. NO. 7) aligned against murine CD154. In each figure, the ISF nucleotide sequence is the upper sequence in the alignment, while the nucleotide sequence for the human or mouse CD154 is the lower sequence.

FIG. 15(a) shows the nucleotide sequence of ISF 38 (SEQ. ID. NO. 9) aligned against human CD154. Regions homologous with human CD154 are indicated by bold type. FIG. 15(b) shows the nucleotide sequence of ISF 38 (SEQ. ID. NO. 9) aligned against murine CD154. In each figure, the ISF nucleotide sequence is the upper sequence in the alignment, while the nucleotide sequence for the human or mouse CD154 is the lower sequence.

FIG. 16(a) shows the nucleotide sequence of ISF 40 (SEQ. ID. NO. 11) aligned against human CD154. Regions homologous with human CD154 are indicated by bold type. FIG. 16(b) shows the nucleotide sequence of ISF 40 (SEQ. ID. NO. 11) aligned against murine CD154. In each figure, the ISF nucleotide sequence is the upper sequence in the alignment, while the nucleotide sequence for the human or mouse CD154 is the lower sequence.

FIG. 17(a) shows the nucleotide sequence of ISF 31 (SEQ. ID. NO. 2) aligned against human CD154. Regions homologous with human CD154 are indicated by bold type. FIG. 17(b) shows the nucleotide sequence of ISF 31 (SEQ. ID. NO. 2) aligned against murine CD154. In each figure, the ISF nucleotide sequence is the upper sequence in the alignment, while the nucleotide sequence for the human or mouse CD154 is the lower sequence.

FIG. 18(a) shows the nucleotide sequence of ISF 33 (SEQ. ID. NO. 4) aligned against human CD154. Regions homologous with human CD154 are indicated by bold type. FIG. 18(b) shows the nucleotide sequence of ISF 33 (SEQ. ID. NO. 4) aligned against murine CD154. In each figure, the ISF nucleotide sequence is the upper sequence in the alignment, while the nucleotide sequence for the human or mouse CD154 is the lower sequence.

FIG. 19(a) shows the nucleotide sequence of ISF 35 (SEQ. ID. NO. 6) aligned against human CD154. Regions homologous with human CD154 are indicated by bold type. FIG. 19(b) shows the nucleotide sequence of ISF 35 (SEQ. ID. NO. 6) aligned against murine CD154. In each figure, the ISF nucleotide sequence is the upper sequence in the alignment, while the nucleotide sequence for the human or mouse CD154 is the lower sequence.

FIG. 20(a) shows the nucleotide sequence of ISF 37 (SEQ. ID. NO. 8) aligned against human CD154. Regions homologous with human CD154 are indicated by bold type. FIG. 20(b) shows the nucleotide sequence of ISF 37 (SEQ. ID. NO. 8) aligned against murine CD154. In each figure, the ISF nucleotide sequence is the upper sequence in the alignment, while the nucleotide sequence for the human or mouse CD154 is the lower sequence.

FIG. 21(a) shows the nucleotide sequence of ISF 39 (SEQ. ID. NO. 10) aligned against human CD154. Regions homologous with human CD154 are indicated by bold type. FIG. 21(b) shows the nucleotide sequence of ISF 39 (SEQ. ID. NO. 10) aligned against murine CD154. In each figure, the ISF nucleotide sequence is the upper sequence in the alignment, while the nucleotide sequence for the human or mouse CD154 is the lower sequence.

FIG. 22(a) shows the nucleotide sequence of ISF 41 (SEQ. ID. NO. 12) aligned against human CD154. Regions homologous with human CD154 are indicated by bold type. FIG. 22(b) shows the nucleotide sequence of ISF 41 (SEQ. ID. NO. 12) aligned against murine CD154. In each figure, the ISF nucleotide sequence is the upper sequence in the alignment, while the nucleotide sequence for the human or mouse CD154 is the lower sequence.

FIG. 23 shows the amino acid sequence of ISF 30 (SEQ. ID. NO. 13) aligned against human and murine CD154. Regions homologous with human CD154 are indicated by bold type. The ISF amino acid sequence is the upper sequence in the alignment, while the amino acid sequence for the human or mouse CD154 is the lower sequence. Alignments for this figure and FIGS. 24-34 were calculated using the "SIM alignment tool for protein sequences" found at http://us.expasy.org/tools/sim-prot.html.

FIG. 24 shows the amino acid sequence of ISF 32 (SEQ. ID. NO. 15) aligned against human and murine CD154. Regions homologous with human CD154 are indicated by bold type. The ISF amino acid sequence is the upper sequence in the alignment, while the amino acid sequence for the human or mouse CD154 is the lower sequence.

FIG. 25 shows the amino acid sequence of ISF 34 (SEQ. ID. NO. 17) aligned against human and murine CD154. Regions homologous with human CD154 are indicated by bold type. The ISF amino acid sequence is the upper sequence in the alignment, while the amino acid sequence for the human or mouse CD154 is the lower sequence.

FIG. 26 shows the amino acid sequence of ISF 36 (SEQ. ID. NO. 19) aligned against human and murine CD154. Regions homologous with human CD154 are indicated by bold type. The ISF amino acid sequence is the upper sequence in the alignment, while the amino acid sequence for the human or mouse CD154 is the lower sequence.

FIG. 27 shows the amino acid sequence of ISF 38 (SEQ. ID. NO. 21) aligned against human and murine CD154. Regions homologous with human CD154 are indicated by bold type. The ISF amino acid sequence is the upper sequence in the alignment, while the amino acid sequence for the human or mouse CD154 is the lower sequence.

FIG. 28 shows the amino acid sequence of ISF 40 (SEQ. ID. NO. 23) aligned against human and murine CD154. Regions homologous with human CD154 are indicated by bold type. The ISF amino acid sequence is the upper sequence in the alignment, while the amino acid sequence for the human or mouse CD154 is the lower sequence.

FIG. 29 shows the amino acid sequence of ISF 31 (SEQ. ID. NO. 14) aligned against human and murine CD154. Regions homologous with human CD154 are indicated by bold type. The ISF amino acid sequence is the upper sequence in the alignment, while the amino acid sequence for the human or mouse CD154 is the lower sequence.

FIG. 30 shows the amino acid sequence of ISF 33 (SEQ. ID. NO. 16) aligned against human and murine CD154. Regions homologous with human CD154 are indicated by bold type. The ISF amino acid sequence is the upper sequence in the alignment, while the amino acid sequence for the human or mouse CD154 is the lower sequence.

FIG. 31 shows the amino acid sequence of ISF 35 (SEQ. ID. NO. 18) aligned against human and murine CD154. Regions homologous with human CD154 are indicated by bold type. The ISF amino acid sequence is the upper sequence in the alignment, while the amino acid sequence for the human or mouse CD154 is the lower sequence.

FIG. 32 shows the amino acid sequence of ISF 37 (SEQ. ID. NO. 20) aligned against human and murine CD154. Regions homologous with human CD154 are indicated by bold type. The ISF amino acid sequence is the upper sequence in the alignment, while the amino acid sequence for the human or mouse CD154 is the lower sequence.

FIG. 33 shows the amino acid sequence of ISF 39 (SEQ. ID. NO. 22) aligned against human and murine CD154. Regions homologous with human CD154 are indicated by bold type. The ISF amino acid sequence is the upper sequence in the alignment, while the amino acid sequence for the human or mouse CD154 is the lower sequence.

FIG. 34 shows the amino acid sequence of ISF 41 (SEQ. ID. NO. 24) aligned against human and murine CD154. Regions homologous with human CD154 are indicated by bold type. The ISF amino acid sequence is the upper sequence in the alignment, while the amino acid sequence for the human or mouse CD154 is the lower sequence.

DETAILED DESCRIPTION OF THE INVENTION

All cited references are incorporated by reference, including any drawings, as if fully set forth herein.

DEFINITIONS

As used herein, the term "CD154" or "chimeric ISF construct" refers to a ligand comprised of at least one domain or subdomain of CD154 from one species and at least one domain or subdomain of CD154 from a different species. Preferably, the at least two species from which the chimeric CD154 is derived are human and murine CD154.

As used herein, the term "subdomain" refers to a sequence of at least two amino acids that is part of a domain of CD154. A "subdomain" also encompasses an amino acid sequence from which one or more amino acids have been deleted, including one or more amino acids truncated from an end of the sequence.

As used herein, the term "cleavage site" refers to a sequence of amino acids that is recognized by proteases, typically matrix metalloproteases (mmp) that cleave CD154 from the surface of the expressing cell. The cleavage site of CD154 is typically found at or around the boundaries of domains III and IV of CD154. According to the invention, one such cleavage site comprises the region approximately between amino acids 108 and 116 of human CD154.

As used herein, the term "corresponding" refers to the sequence of nucleotides or amino acids of CD154 of one species that is homologous to a nucleotide or amino acid sequence of CD154 of another species. This homology is based on the similarity in secondary structure, such as the location of domain boundaries, among CD154 of different species (see Table I below).

As used herein, the phrase "less susceptible to cleavage" refers to the higher resistance of a chimeric CD154 to proteolytic cleavage compared to that of native human CD154, as measured by the amount of soluble CD154 generated by a given number of cells over a period of time. Preferably, a chimeric CD154 of the present invention is "less susceptible to cleavage" because it is cleaved at a rate at least 90% less than that of native CD154.

As used herein, the term "expression vector" refers to a nucleic acid that expresses a recombinant nucleotide sequence and that is capable of infecting cells and replicating itself therein. Typical expression vectors include plasmids used in recombinant DNA technology and various viruses capable of replicating within bacterial or animal cells. A number of expression vectors have been described in the literature. Cantwell et al., *Blood*, In (1996) entitled "Adenovirus Vector Infection of Chronic Lymphocytic Leukemia B Cells;" Woll, P. J. and I. R. Hart, *Ann. Oncol.*, 6 Suppl 1:73 (1995); Smith, K. T., A. J. Shepherd, J. E. Boyd, and G. M. Lees, *Gene Ther.*, 3:190 (1996); Cooper, M. J., *Semin. Oncol.*, 23:172 (1996); Shaughnessy, E., D. Lu, S. Chatterjee, and K. K. Wong, *Semin. Oncol.*, 23:159 (1996); Gloriosa, J. C., N. A. DeLuca, and D. J. Fink, *Annu. Rev. Microbial.*, 49:675 (1995); Flotte, T. R. and B. J. Carter, *Gene Ther.*, 2:357 (1995); Randrianarison-Jewtoukoff, V. and M. Perricaudet, *Biologicals.*, 23:145 (1995); Kohn, D. B., *Curr. Opin. Pediatr.*, 7:56 (1995); Vile, R. G. and S. J. Russell, *Br. Med. Bull.*, 51:12 (1995); Russell, S. J., *Semin. Cancer Biol.*, 5:437 (1994); and Ali, M., N. R. Lemoine, and C. J. Ring, *Gene Ther.*, 1:367 (1994).

Nucleotide Sequences Encoding Chimeric CD154

As noted above, ligands of the TNF superfamily ("TNF ligands") have a similar secondary structure consisting of a number of domains (Kipps et al., WO98/76061 published Jun. 18, 1998). In Table I, the domain boundaries of a number of ligands of the TNF superfamily are shown. Based on the x-ray crystal structure of human TNFα, the predicted secondary structure of the receptor-binding portion of human CD154 has been deduced (Peitsch et al, Int Immunol, 5:233-238, 1993). The secondary structures of the receptor-binding portions of other TNF ligands were deduced by comparison to human TNFα, using computer analysis.

TABLE I

Domain Structure of Ligands from the TNF Superfamily*

|  | Domain I (Cytoplasmic) | Domain II (Transmembrane) | Domain III (Proximal Extracellular) | Domain IV (Distal Extracellular) |
| --- | --- | --- | --- | --- |
| Human CD154 | 1-42 | 42-135 | 135-330 | 330-786 |
| Murine CD154 | 1-42 | 42-135 | 135-327 | 327-783 |
| Bovine CD154 | 1-42 | 42-135 | 135-330 | 330-786 |
| Human TNFα | 1-87 | 87-168 | 168-228 | 228-699 |
| Murine TNFα | 1-87 | 87-168 | 168-237 | 237-705 |
| Porcine TNFα | 1-87 | 87-168 | 168-228 | 228-696 |
| Human Fas Ligand | 1-237 | 237-315 | 315-390 | 390-843 |
| Murine Fas Ligand | 1-237 | 237-309 | 309-384 | 384-837 |
| Human CD70 | 1-45 | 45-117 | 117-132 | 132-579 |

TABLE I-continued

Domain Structure of Ligands from the TNF Superfamily*

|  | Domain I (Cytoplasmic) | Domain II (Transmembrane) | Domain III (Proximal Extracellular) | Domain IV (Distal Extracellular) |
|---|---|---|---|---|
| Human CD30 Ligand | 1-117 | 117-186 | 186-240 | 240-702 |
| Human TRAIL | 1-42 | 42-111 | 111-345 | 345-843 |

*The domains are identified by the nucleotide boundaries of each domain using the first nucleotide of the initial methionine of the cDNA as nucleotide number 1. According to the invention, the nucleotide boundaries shown may vary considerably from those identified and still define domains that are useful in the present invention.

Given the similarities in nucleotide sequences coding for CD154 molecules of different species, such as human, mouse and cow, a nucleotide sequence encoding one domain or subdomain of CD154 from one species is interchangeable with the corresponding nucleotide sequence of CD154 from another species to result in a hybrid polynucleotide sequence that encodes a chimeric CD154.

The nucleotide sequences that are exchanged for corresponding sequences between species are selected for functional reasons, i.e., because the selected sequence encodes a domain or subdomain that either provides or modifies a desired function, or eliminates an undesired function of the target ligand gene.

It is known in the art that at least part of human CD154 is cleaved from the parent molecule and becomes a soluble molecule. As described above, the soluble form is generally undesirable. Thus, exchanging an amino acid, or an amino acid sequence, of human CD154 that comprises a cleavage site recognized by proteolytic enzymes with an amino acid, or amino acid sequence, of non-human CD154, that does not contain this cleavage site, would at least partially ameliorate that problem. Preferably, the non-human CD154 is murine CD154.

According to the invention, an extracellular domain of human CD154 includes at least one amino acid, or a sequence of amino acids, at or near the border of domain III and domain IV that is recognized and cleaved by cleavage proteases. According to the present invention, at least one such cleavage site exists between nucleotides 322-348, amino acids 108-116, of human CD154.

Moreover, according to the invention, an extracellular domain of human CD154 includes at least one amino acid, or a sequence of amino acids, that binds to a human CD154 receptor, e.g., CD40. For this reason, even the soluble form of CD154 is capable of binding CD154 receptors on antigen presenting cells and may actively participate in an immune response. Thus, this extracellular region of human CD154 must be conserved in order to maintain native CD154 receptor binding.

Accordingly, a presently preferred embodiment of the present invention is a chimeric CD154 polynucleotide sequence comprising a first nucleotide sequence encoding an extracellular subdomain of non-human CD154 that corresponds to and replaces a cleavage site of human CD154. According to this invention, replacing a subdomain of human CD154 containing a CD154 cleavage site with the corresponding subdomain of non-human CD154 results in a chimeric CD154 that is markedly less susceptible to cleavage than human CD154.

This first nucleotide sequence is operatively linked to a second nucleotide sequence that encodes an extracellular subdomain of human CD154 involved in binding to a human CD154 receptor, such as the CD40 ligand. In this way, the polynucleotide sequence provided by the present invention encodes a chimeric CD154 that binds to human cells expressing the CD154 receptor.

Moreover, according to the invention, an extracellular domain of murine and human CD154 includes at least one amino acid, or a sequence of amino acids, that allows expression of the molecule on the membranes of murine and human cells. For instance, FIG. 9 shows that both murine and human CD154 are expressed by HeLa cells. However, as described above, murine CD154 is expressed by a greater variety of cells, including human cells, as compared to human CD154. In fact murine CD154 may be expressed in human cells that typically do not express human CD154, such as human CD40+ cells, particularly CLL cells. This differential expression between human and murine CD154 is also confirmed by the data shown in FIG. 9. Thus, exchanging an amino acid, or sequence thereof, of human CD154 that is involved in expression of the human molecule with an amino acid, or sequence thereof, of murine CD154 involved in expression of the non-human molecule would at least partially address this problem.

Accordingly, in the preferred embodiment of the present invention, the chimeric CD154 polynucleotide sequence comprises a first nucleotide sequence that further encodes an extracellular subdomain of murine CD154 that is critical for expression of the murine CD154 molecule by murine and human cells. In this way, the polynucleotide sequence provided by the present invention encodes a chimeric CD154 that is capable of expression by a variety of cell types, including human CD40+ cells that do not typically express human CD154. Although this embodiment involves the use of murine CD154, the present invention contemplates the use of other non-human CD154 that may be expressed by human cells.

Further, according to the invention, an extracellular domain of murine CD154 includes an amino acid, or a sequence of amino acids, involved in detecting the expression of the chimeric CD154 because it binds to murine CD154 specific antibody. In this way, the expression of the chimeric CD154 polynucleotide sequence can be specifically detected, typically by FACS or immunohistochemistry, and thereby be distinguished from expression of native human CD154.

Accordingly, in the preferred embodiment of the present invention, the chimeric CD154 polynucleotide sequence comprises a first nucleotide sequence that further encodes an extracellular subdomain of non-human CD154 that detects the expression of chimeric CD154 by binding to anti-murine CD154 antibodies.

In the preferred embodiment of the present invention, this first nucleotide sequence encodes a subdomain of domain IV of non-human CD154, preferably murine. This subdomain IV of murine CD154 comprises the amino acid sequences that replace the cleavage site of human CD154, that are critical for expression of the murine molecule by murine and human cells, and that are involved in detection of the chimeric CD154 of the present invention. In addition, this first nucleotide sequence may encode a subdomain of domain III of non-human CD154 that is at or immediately adjacent to the border of domains III and domain IV. According to the present invention, this subdomain comprises a portion of a cleavage site of human CD154.

Preferably, the first nucleotide sequence further encodes domains I, II and III of murine CD154, because this construct has been shown to result in improved expression of the chimeric CD154 by human cells. Alternatively, the first nucleotide sequence may encode domain III or a subdomain thereof, of murine CD154; and/or domain II, or a subdomain thereof, of murine CD154; and/or domain 1, or a subdomain thereof of murine CD154.

Further, according to the invention, an extracellular domain of murine and human CD154 includes at least one amino acid, or a sequence of amino acids, that may bind to anti-CD154 antibodies, and thereby neutralize the immune-activating effect of the ligand. This amino acid or amino acid sequence is typically the same or substantially similar to the regions in the tertiary structure of CD154 that bind to CD40, CD154's cognate receptor. As described above, murine CD154 elicits a greater response in terms of anti-CD154 antibody production. As such, it is more sensitive than human CD154 to binding and neutralization by anti-CD154 antibodies, resulting in long-term problems with repeated administration of murine CD154 in humans. That is, administration of murine CD154, or of a CD154 construct wherein the region to which anti-CD154 antibodies bind is murine, results in an immunogenic reaction against the administered CD154 and thus decreased efficacy in stimulating an immune response. Thus, preferably, the region involved in binding anti-CD154 antibodies is human CD154 to prevent or minimize any immunogenic effect upon administration.

Accordingly, a presently preferred embodiment of the present invention is a chimeric CD154 polynucleotide sequence comprising a second nucleotide sequence of human CD154 that further encodes an extracellular subdomain to which anti-CD154 antibodies bind. In this way, the polynucleotide sequence provided by the present invention encodes a chimeric CD154 that is not immunogenic upon administration in humans.

Preferably, the second nucleotide sequence encodes a subdomain of domain IV of human CD154. Thus, a presently preferred polynucleotide sequence encodes a subdomain of domain IV of human CD154 operatively linked to another subdomain of domain IV of murine CD154.

As described above, domain IV is preferably linked to domains I, II and III of murine CD154. Examples of such preferred polynucleotide sequences are provided herein as SEQ ID. NOS. 1, 3, 5, 7, 9 and 11 and encode chimeric CD154 constructs that have been designated ISF 30, 32, 34, 36, 38 and 40, respectively. The homology of these chimeric constructs with murine and human CD154 is represented by the following Table II, and can be seen in FIGS. 11-16.

TABLE II

Even-Numbered ISF Series Nucleotide Maps

| ISF Construct | Fragment 1 Murine CD154 Homology | Fragment 2 Human CD154 Homology | Fragment 3 Murine CD154 Homology | Fragment 4 Human CD154 Homology |
|---|---|---|---|---|
| ISF 30 | 1-447 | 448-543 | 544-666 | 667-783 |
| ISF 32 | 1-447 | 448-567 | 568-666 | 667-783 |
| ISF 34 | 1-447 | 448-567 | 568-654 | 655-783 |
| ISF 36 | 1-447 | 448-567 | 568-618 | 622-783 |
| ISF 38 | 1-447 | 448-543 | 544-654 | 655-783 |
| ISF 40 | 1-447 | 448-543 | 544-618 | 619-783 |

Alternatively, domain IV may be linked to domains I, II and III of human CD154. Examples of such polynucleotide sequences are provided as SEQ ID. NOS. 2, 4, 6, 8, 10 and 12, and encode chimeric CD154 constructs that have been designated ISF 31, 33, 35, 37, 39 and 41, respectively. The homology of these chimeric constructs with murine and human CD154 is represented by the following Table III, and can be seen in FIGS. 17-22.

TABLE III

Odd-Numbered ISF Series Nucleotide Maps*

| ISF Construct | Fragment 1 Human CD154 Homology | Fragment 2 Murine CD154 Homology | Fragment 3 Human CD154 Homology | Fragment 4 Murine CD154 Homology | Fragment 5 Human CD154 Homology |
|---|---|---|---|---|---|
| ISF 31 | 1-321 | 322-423 | 424-519 | 520-642 | 643-759 |
| ISF 33 | 1-321 | 322-423 | 424-543 | 544-642 | 643-759 |
| ISF 35 | 1-321 | 322-423 | 424-543 | 544-630 | 631-759 |
| ISF 37 | 1-321 | 322-423 | 424-543 | 544-594 | 592-759 |
| ISF 39 | 1-321 | 322-423 | 424-519 | 520-630 | 631-759 |
| ISF 41 | 1-321 | 322-423 | 424-519 | 520-594 | 595-759 |

*A 27 nucleotide region present in human CD154 (nucleotides 322-348), roughly corresponding to a portion of domain III and domain IV of human CD154, has been deleted from this series of constructs between nucleotides 321 and 322 of fragments 1 and 2, respectively.

III) Chimeric CD154 Polypeptides

The encoded chimeric CD154 therefore comprises a first subdomain of non-human CD154, and preferably murine CD154 that replaces a cleavage site of human CD154 and a second subdomain of human CD154 that binds to a CD154 receptor. As a result, the chimeric CD154 is less susceptible to cleavage from the surface of cells than human CD154, but nonetheless retains the capability of binding to the cognate receptor of native CD154. This decreased susceptibility to cleavage from the cellular surface is reflected by a cleavage rate of the chimeric CD154 that is at least 90% less than that of human CD154.

Moreover, the first subdomain of murine CD154 is critical for expression of murine CD154 by murine and human cells, and thus allows for expression of the chimeric CD154 by human cells. As a consequence, the chimeric CD154 is capable of being expressed by human CD40+ cells, including CLL cells, that do not typically express human CD154.

In addition, the first subdomain of murine CD154 is capable of detecting the expression of chimeric CD154 because it binds to murine CD154 specific antibody, and thus distinguishes its expression from expression of native human CD154.

The second subdomain of human CD154 preferably comprises one to which anti-CD154 antibodies bind. Given human CD154's decreased sensitivity to these antibodies, the resulting chimeric CD154 is not immunogenic and thus does not result in antibody neutralization.

Preferably, the first subdomain of non-human CD154 comprises a subdomain of domain IV, and a subdomain of domain III at or immediately adjacent to the border of domains III and IV that correspond to a portion of a CD154 cleavage site. The second subdomain of human CD154 also comprises a subdomain of domain IV. In preferred embodiments, domains I-III also comprise murine CD154. Examples of such preferred chimeric constructs are provided as SEQ ID. NOS. 13, 15, 17, 19, 21 and 23, corresponding to ISF 30, 32, 34, 36, 38 and 40. This homology of these chimeric constructs with murine and human CD154 is represented by the following Table IV, and can be seen in FIGS. 23-28:

TABLE IV

Even Number ISF Series Amino Acid Maps

| ISF Construct | Fragment 1 Murine CD154 Homology | Fragment 2 Human CD154 Homology | Fragment 3 Murine CD154 Homology | Fragment 4 Human CD154 Homology |
|---|---|---|---|---|
| ISF 30 | 1-149 | 150-181 | 182-222 | 223-260 |
| ISF 32 | 1-149 | 150-189 | 190-222 | 223-260 |
| ISF 34 | 1-149 | 150-189 | 190-218 | 219-260 |
| ISF 36 | 1-149 | 150-189 | 190-206 | 207-260 |
| ISF 38 | 1-149 | 150-181 | 182-218 | 219-260 |
| ISF 40 | 1-149 | 150-181 | 182-206 | 207-260 |

Alternatively, domains I-III may comprise human CD154. Examples of such preferred constructs are provided as SEQ ID. NOS. 14, 16, 18, 20, 22 and 24, corresponding to ISF 31, 33, 35, 37, 39 and 41. The homology of these chimeric constructs with murine and human CD154 is represented by the following Table V, and can be seen in FIGS. 29-34.

TABLE V

Odd Number ISF Series Amino Acid Maps*

| ISF Construct | Fragment 1 Human CD154 Homology | Fragment 2 Murine CD154 Homology | Fragment 3 Human CD154 Homology | Fragment 4 Murine CD154 Homology | Fragment 5 Human CD154 Homology |
|---|---|---|---|---|---|
| ISF 31 | 1-107 | 108-141 | 142-173 | 174-214 | 215-252 |
| ISF 33 | 1-107 | 108-141 | 142-181 | 182-214 | 215-252 |
| ISF 35 | 1-107 | 108-141 | 142-181 | 182-210 | 211-252 |
| ISF 37 | 1-107 | 108-141 | 142-181 | 182-198 | 199-252 |
| ISF 39 | 1-107 | 108-141 | 142-173 | 174-210 | 211-252 |
| ISF 41 | 1-107 | 108-141 | 142-173 | 174-198 | 199-252 |

*A nine amino acid region present in human CD154 (amino acids 108-116), roughly corresponding to a portion of domain III and domain IV of human CD154, has been deleted from this series of constructs between amino acids 107 and 108 of fragments 1 and 2, respectively.

Genetic Constructs

The present invention also contemplates an expression vector or any other genetic construct that comprises a polynucleotide sequence of the present invention capable of expressing a chimeric CD154 in a target cell.

An expression vector useful in the present invention contains a polynucleotide sequence encoding a chimeric CD154 operatively linked to a suitable transcriptional or translational regulatory nucleotide sequence, such as one derived from a mammalian, microbial, viral, or insect gene. Such regulatory sequences include sequences having a regulatory role in gene expression, such as a transcriptional promoter or enhancer, an operator sequence to control transcription, a sequence encoding a ribosomal binding site within the messenger RNA, and appropriate sequences which control transcription, translation initiation, or transcription termination.

Particularly useful regulatory sequences include the promoter regions from various mammalian, viral, microbial, and insect genes. The promoter region directs an initiation of transcription through and including the polynucleotide sequence encoding the chimeric CD154 of the present invention. Useful promoter regions include the promoter found in the Rous Sarcoma Virus (RSV) long terminal repeat (LTR), human cytomegalovirus (CMV) enhancer/promoter region, lac promoters, promoters isolated from adenovirus, and any other promoter known by one of ordinary skill in the art would understand to be useful for gene expression in eukaryotes, prokaryotes, viruses, or microbial cells. Other promoters that are particularly useful for expressing genes and proteins within eukaryotic cells include mammalian cell promoter sequences and enhancer sequences such as those derived from polyoma virus, adenovirus, simian virus 40 (SV40), and the human cytomegalovirus. Particularly useful are the viral early and late promoters, which are typically found adjacent to the viral origin of replication in viruses such as the SV40. One of ordinary skill in the art will understand that the selection of a particular useful promoter depends on the exact cell lines and the other various parameters of the genetic construct to be used to express a polynucleotide sequence within a particular cell line.

Certain genetic constructs contemplated by the present invention therefore include a polynucleotide sequence operatively linked to either a promoter sequence or a promoter and enhancer sequence and also operatively linked to a polyadenylation sequence that directs the termination and polyadenylation of messenger RNA. Preferably, the polynucleotide sequence is constructed using the CMV promoter and the bovine growth hormone polyadenylation sequence.

Host Cells

The present invention also contemplates various host cells that are transformed or transfected with an expression vector or other genetic construct that contains a polynucleotide sequence of the present invention. These cells may be prokaryotic or eukaryotic cells.

In some preferred embodiments the cells are normal antigen presenting cells of a mammal, such as monocytes, macrophages, B cells, and the like. In other preferred embodiments, the cells may be normal cells that are capable of stimulating bystander antigen presenting cells when a polynucleotide sequence of the present invention is introduced into these cells. The present invention also contemplates somatic cells that are not naturally capable of presenting antigen to the immune system but may be genetically engineered with the genes encoding the molecules required for antigen presentation, and thus allow these cells to act as artificial antigen presenting cells. A polynucleotide sequence encoding a chimeric CD154 may then be introduced into these artificial antigen presenting cells. Various tests are well known in the literature to determine whether a particular cell is able to function as an antigen presenting cell, such as cell proliferation or the production of lymphokines, and therefore this aspect of the present invention may be easily determined.

In addition to the above normal human cells, the present invention also contemplates introducing a polynucleotide sequence encoding a chimeric CD154 into various neoplastic or malignant cells, such as cells of the immune system and solid tumors. Such neoplastic cells that are contemplated include leukemia cells, such as acute monocytic leukemia (AML), acute myelomonocytic leukemia (AMML), chronic lymphocytic leukemia (CLL), chronic myelogenous or chronic myelomonocytic leukemia (CMML). Also contemplated are cells derived from lymphomas, gliomas, breast, cervical, ovarian, lung, bladder, or prostate cancers.

Finally, in a preferred embodiment of the present invention, a polynucleotide sequence encoding a chimeric CD154 is introduced into cells that express its cognate receptor, CD40, on surfaces of the cells.

Methods Utilizing Expression Vectors and Constructs Containing Chimeric CD154 Polynucleotide Sequences Recognizing the interaction of CD154 and its cognate receptor in regulating the immune response, the present invention also contemplates methods of increasing the concentration of a membrane-stabilized ligand capable of binding to CD40, or some other cognate receptor for CD154, by introducing a polynucleotide sequence encoding a chimeric CD154 into a cell, whereby the chimeric CD154 is less susceptible to cleavage from the surface of that cell relative to native CD154. Because the chimeric CD154 is less susceptible to proteolytic cleavage, it has increased capacity to bind to its cognate receptor and induce either a cytolytic response or an immune response.

The present invention is useful for any human cell that participates in an immune reaction either as a target for the immune system or as part of the immune system's response to the foreign target. The methods include ex vivo methods, in vivo methods, and various other methods that involve injection of polynucleotides or vectors into the host cell. The methods also include injection directly into the tumor or tumor bed.

The present invention thus contemplates ex vivo methods comprising isolation of cells from an animal or human subject. A polynucleotide sequence encoding a chimeric CD154 of the present invention is introduced into the isolated cells. The cells are then re-introduced at a specific site or directly into the circulation of the subject. In a preferred embodiment of the present invention, cell surface markers, including molecules such as tumor markers or antigens that identify the cells, may be used to specifically isolate these cells from the subject.

The present invention also contemplates introducing a polynucleotide sequence encoding a chimeric CD154 into the desired cells within the body of an animal or human subject without first removing those cells from the subject. Methods for introducing polynucleotide sequences into specific cells in vivo, or within the subject's body are well known and include use of expression vectors and direct injection of various genetic constructs into the subject. In a typical application, an expression vector containing a polynucleotide sequence of the present invention is introduced into the circulation or at a localized site of the subject to allow the vector to specifically infect the desired cells. In other preferred embodiments the vector is injected directly into the tumor bed present in a subject that contains at least some of the cells into which the polynucleotide sequence of the present invention is to be introduced.

The present invention also contemplates directly injecting into an animal or human subject a genetic construct that includes a polynucleotide sequence encoding a chimeric CD154, and may additionally include a promoter and a polyadenylation sequence. Examples of such useful methods have been described (Vile et al, Ann Oncol, 5:59-65, 1994). The genetic construct may also be directly injected into the muscle or other sites of an animal or human subject or directly into the tumor or tumor bed of the subject.

Methods of Treating Neoplasia

The present invention is also directed to methods of treating neoplasia, comprising inserting into a neoplastic cell a polynucleotide sequence of the present invention, so that the encoded chimeric CD154 is expressed on the surface of the neoplastic cells. The present invention contemplates treating human neoplasia both in vivo and ex vivo.

In a preferred method of treating neoplasia, the method further comprises the steps of first obtaining the neoplastic cells from a subject, inserting therein a polynucleotide sequence of the present invention so that a chimeric CD154 is expressed on the surface of the neoplastic cells, and re-administering the cells back into the subject. One of ordinary skill in the art will understand that numerous methods are applicable for re-administering the transformed neoplastic cells into the subject.

EXAMPLES

1. Expression of Chimeric Accessory Molecule Ligand in Human HeLa Cells and CLL Cells a. Construction of a Genetic Construct and Gene Therapy Vector Containing a Chimeric Accessory Molecule Ligand Gene The chimeric accessory molecule ligand genes of SEQ ID NO. 1-SEQ ID NO. 12 (aka ISF 30-ISF 41) are prepared and cloned as follows:

i. Preparation of Chimeric Accessory Molecule Ligand Gene Utilizing Domains from Two Different Gene Species The chimeric constructs of the present invention were designed by two well-characterized methods of gene fusion and site-directed mutagenesis. Substitution of large domains, for example fusion of the domain IV region of human onto domains I-III of mouse, was accomplished by a gene-fusion technique described by Ho[48]. Smaller gene replacements or amino acid substitutions were performed by a QUICK-CHANGE site-directed mutagenesis protocol described by Stratagene, Inc (La Jolla, Calif.). Chimeric ISF genes were subcloned in the pcDNA3 eukaryotic expression vector (Invitrogen, Inc. La Jolla, Calif.). The chimeric ISF insert is flanked by the heterologous CMV promoter and the bovine growth hormone polyadenylation sequence.

ii. Adenovirus Synthesis

The chimeric ISF-pcDNA3 plasmids were digested with the restriction enzymes NruI and Sma Ito release a DNA fragment containing the CMV promoter from pCDNA3, the chimeric CD154 gene, and the polyadenylation signal from pCDNA3. Following gel purification of this fragment by separation of the digested DNA on a 1% agarose gel, the DNA fragment was ligated into the EcoRV site of the adenoviral shuttle vector MCS (SK) pXCX2. This plasmid is a modification of the plasmid pXCX2 such that the pBluescript polylinker sequence has been cloned into the E1 region, (J. R. Tozer, UCSD, unpublished data, September 1993). Following purification of chimeric ISF-MCS (SK) pXCX2 plasmid, 5 ug of this shuttle plasmid was cotransfected with 5 ug of JM17 plasmid into 293AC2 cells using the calcium phosphate Profection Kit from Promega according to the manufacturer's instructions. Following transfection, the cells were cultured for 5 days to allow for homologous recombination and viral synthesis. Total cells and supernatant were then harvested and freeze-thawed thrice to release cell-associated adenovirus.

Following the initial viral production, a clonal isolate of the virus obtained by plaque purification. Briefly, the freeze-thawed viral supernatant was cleared of debris by centrifugation at 1000 rpm in a tabletop centrifuge for 5 minutes. 293AC2 cells grown to confluency in 6 well tissue culture plates were then infected with serial dilutions of the viral supernatant for 1-2 hours. Following infection, the media was aspirated and cells overlayed with DMEM media containing 4% fetal calf serum and 0.65% agarose held at 56° C. Following 4-6 days incubation, isolated plaques were picked into 1 ml of media and subsequently used for viral amplification.

Figure 3:
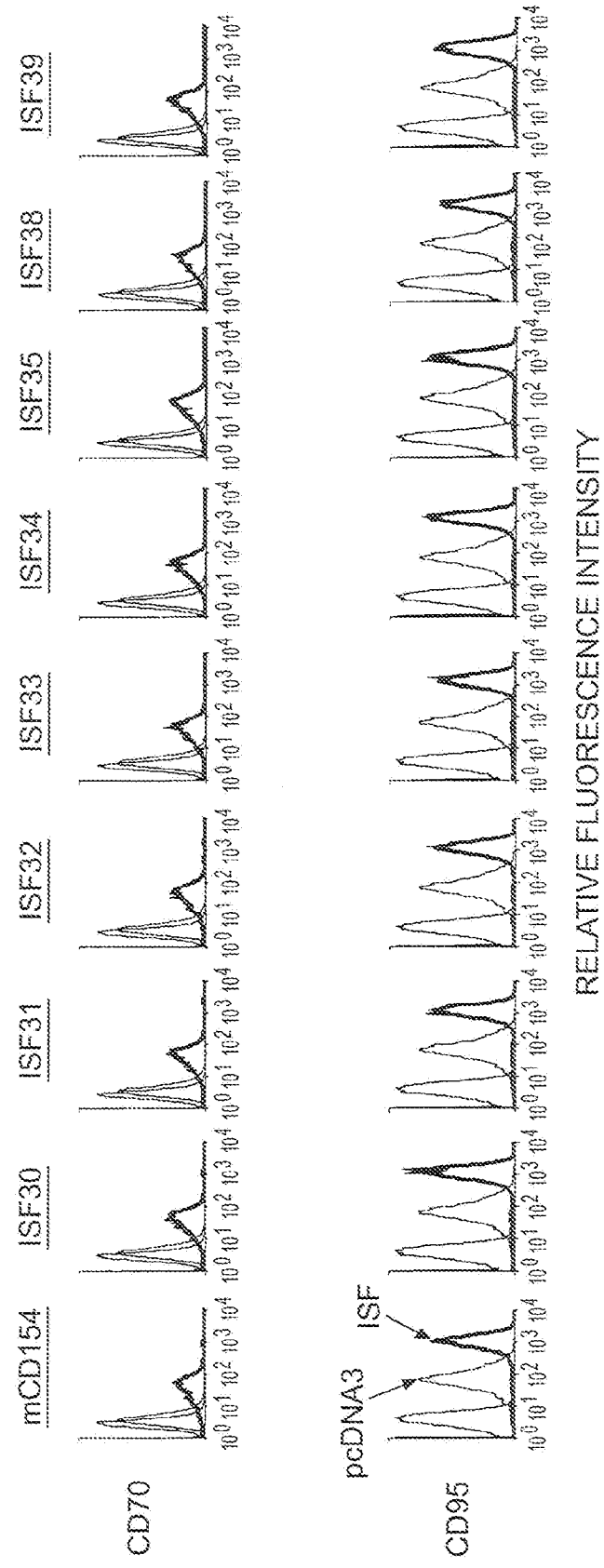

Large-scale adenovirus preparations were prepared by successively infecting increasing quantities of 293AC2. Purified adenovirus was then purified over cesium chloride step gradients. This method makes use of a cesium chloride gradient for concentrating virus particles via a step gradient, with the densities of 1.45 g/cm$^3$ and 1.20 g/cm$^3$, in which 293AC2 expanded virus samples are centrifuged for 2 hours in a SW40 rotor (Beckman, Brea, Calif.) at 25,000 rpm at 4° C. The virus band is isolated using a 27-gauge needle and syringe and desalted using a Sephadex G-25 DNA grade column (Pharmacia, Piscataway, N.J.). The virus is desalted against phosphate-buffered saline containing 10% glycerol and stored at −70° C. The final titer of the virus was determined by anion-exchange HPLC.

b. Expression and Function of a Chimeric Accessory Molecule Ligand Gene in CLL Cells and HeLa Cells i. Expression FIG. 3 shows that expression of many of the panel of ISF constructs. i.e., ISF 30-ISF 39, on HeLa following transfection of these cells with pcDNA3 plasmid containing each respective ISF construct. HeLa cells were transiently transfected with ISF-pcDNA3 plasmid using lipofectamine 2000 (Gibco-BRL), a liposome-based transfection reagent allowing for efficient gene transfer into HeLa. Two days following transfection, cells were analyzed for cell surface expression of the chimeric CD154 by flow cytometry. Briefly, the adherent cells are detached from the wells by aspirating the media and adding detaching solution (PBS containing 10 mM EDTA, pH 8). This detaching solution is used in place of the more common trypsinization buffer to avoid nonspecific cleavage of CD154 at trypsin sensitive sites, thus potentially leading to false negative assessment of expression. Once the cells detach from the plate, the cells are washed once in FACS staining buffer (composed of PBS containing 3% FCS and 0.05% sodium azide), resuspended in FACS buffer to approximately 10$^7$ cells/ml, and 5×10$^5$ (50 ul) cells are plated in 96-well u-bottom plastic microwell plates. PE-conjugated antibody specific for CD154 (antibody clone MR-1, Pharmingen, Inc.) is added for 30 minutes at 4° C. The cells are then washed twice with FACS buffer, resuspended in FACS buffer, and transferred to FACS tubes for data acquisition. To control for nonspecific antibody binding, all samples are stained with appropriate isotype control antibodies. Furthermore, dead cells and debris are excluded from analysis by addition of 10 ng/ml propidium iodide to all staining reactions. The cells are analyzed by flow cytometry for CD154 expression using a FACSCalibur flow cytometer (Becton Dickinson).

The results in FIG. 3 show the chimeric CD154 vectors are all expressed as cell surface ligands that can be detected with CD154-specific antibody, suggesting overall protein tertiary structure is maintained. Moreover, surface expression is equivalent or better than native murine CD154.

ii. Functional Assays of Chimeric Accessory Molecule Ligands

Figure 4:
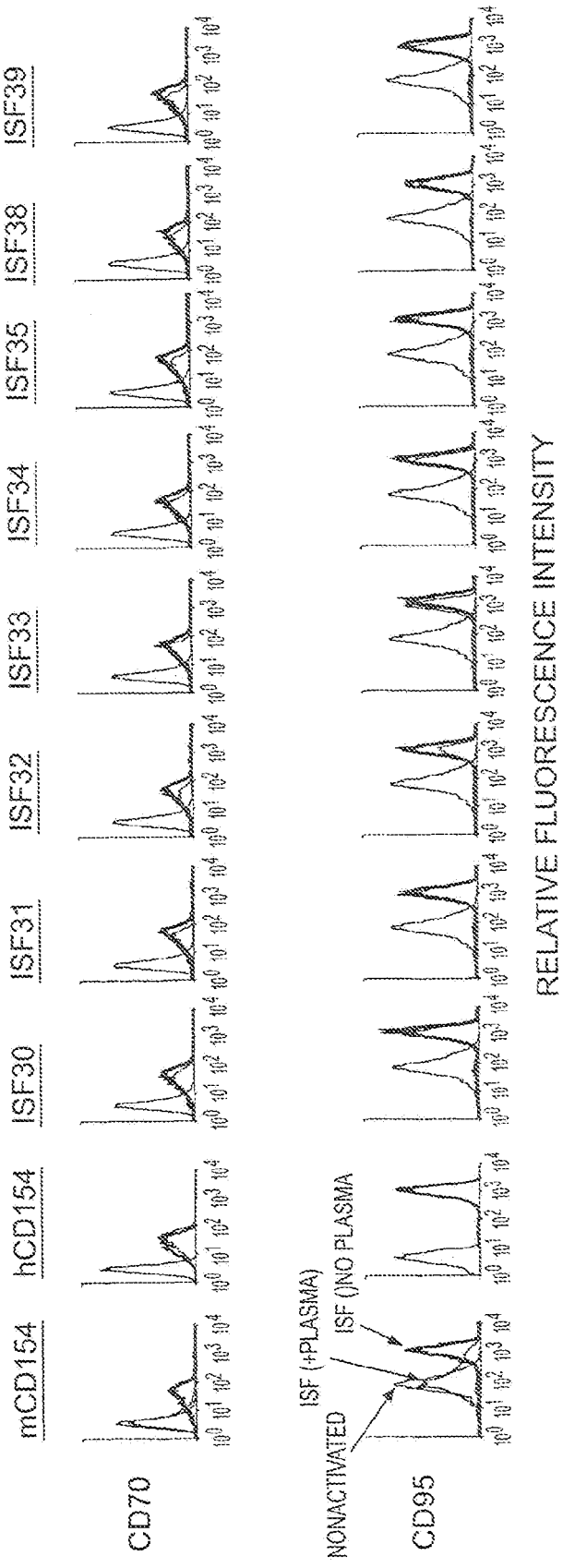

FIG. 4 shows the functional capacity of several constructs of the ISF panel described in FIG. 2 to activate Ramos B cells, a CD40-positive cell line. Ramos cells were overlayed onto the HeLa cells transfected with ISF-pcDNA3 as described above. One day following overlay, the nonadherent Ramos cells were harvested and analyzed for expression of CD70 and CD95 expression by flow cytometry. These two cell surface markers are expressed at higher levels following CD40 activation. (Kato K. et al., *J. Clin. Invest.*, 104:947-955, 1999.) This data shows that all the ISF constructs activate Ramos cells with equivalent intensity as native murine CD154. This is further proof that overall CD154 tertiary protein structure and receptor specificity is maintained in the chimeric CD154 constructs.

1. CD154 Patient-Antibody Neutralization and Binding Data

FIG. 5 shows the sensitivity of the ISF constructs to CLL patient plasma, collected from the phase-I CD154 clinical trial, that contain antibody capable of neutralizing native murine CD154 function. Briefly, Ramos cells were overlayed onto HeLa cells transfected with ISF-pcDNA3 as described in FIG. 3. At the same time, patient plasma containing mCD154 neutralizing antibody was added during the co-incubation. Following one-day incubation, the Ramos cells were harvested and analyzed for CD70 and CD95 surface expression as described in FIG. 4. This data shows the patient plasma inhibits mCD154 activation of Ramos, as expected. In contrast, patient plasma did not inhibit ISF function.

In addition, ISF constructs were tested for binding of CD154-specific antibody in patient plasma as another measure of immunogenicity. Again, HeLa cells transfected with the ISF-pcDNA3 plasmids were incubated with serial dilutions of patient plasma for 30 minutes at 4° C. The cells were then washed of unbound antibody and stained with a fluorescent-labeled antibody specific for human immunoglobulin (Ig). Following this secondary stain, cells were washed and analyzed by FACS. FIG. 6 shows less binding of patient plasma antibodies described in FIG. 5 to representative ISF constructs compared to mCD154. Although a small amount of bound antibody can be detected, this is obviously not deleterious to ISF function based on the result from FIG. 4. Moreover, less antibody binding is detected on ISF 35 than ISF 30. These results are explained by the fact ISF 35 contains more human CD154 regions than ISF 30 (see FIG. 2). Together, results from FIG. 5 and FIG. 6 satisfy criteria of an optimized CD154 construct since the ISF constructs lack immunogenic regions responsible for ligand neutralization by patient generated antibodies.

2. Adenovirus Mediated ISF Expression and Function

Recombinant adenovirus encoding each ISF transgene was tested for its ability to infect HeLa and lead to ISF membrane expression. FIG. 7 shows the expression of selected ISF constructs on HeLa cells infected with increasing multiplicity of infection (M.O.I) ratios of adenovirus in comparison to cells infected with adenovirus encoding murine CD154 (Ad-mCD154). First, this data shows the adenovirus vectors are intact and contain the ISF transgene of interest. Second, this data further confirms the ISF constructs are expressed with at least equivalent intensity as mCD154. As such, the chimeric state of the ISF constructs is not deleterious to expression in a cell line highly permissive to adenovirus infection and CD154 expression.

FIG. 8 shows the expression of ISF constructs on CLL B cells following infection with the adenovirus vectors described above. Unlike HeLa, CLL is difficult to infect with adenovirus and precludes expression of human CD154. As can be seen, the ISF constructs can be expressed on CLL cells following adenovirus infection with similar expression intensity as mCD154. As such, these vectors satisfy another criteria for an optimized CD154 construct, namely, expression in human CD154 expression-resistant cell types.

As another criterion for a preferred CD154 construct, CLL B cells were examined for cell activation following infection with the adenovirus vectors encoding the ISF constructs described in FIG. 8. Two days after infection, CLL cells were stained for modulation of a panel of surface markers characteristic of CD40 activation. FIG. 9 shows ISF expression resulted in changes in expression of these markers. The changes were equivalent or greater than cells infected with Ad-mCD154.

Finally, as seen in FIG. 10, at least one of the chimeric CD154 polypeptides of the present invention is significantly more stable and resistant to proteolytic cleavage as compared to human CD154 that is known to be proteolytically cleaved into a soluble molecule following expression by cells. HeLa cells were either not infected or infected with adenovirus encoding either human CD154 or ISF 35 at a MOI of 10. Two days following infection, the culture supernatant was collected and measured for the presence of soluble ligand using a human CD154-specific ELISA (enzyme linked immunosorbent assay). The quantity of soluble CD154 was calculated based on titration of a known amount of a soluble CD40 ligand-CD8 fusion protein in the ELISA (Ancell Inc.). The quantity of soluble ligand detected in the supernatant is plotted in the bar graph of FIG. 10. This plot shows that ISF 35 is resistant to proteolytic cleavage into soluble ligand since no soluble ISF 35 can be detected. In contrast, human CD154 is readily cleaved into soluble CD154 at levels >120 ng/ml. Moreover, the absence of soluble ISF 35 was not due to lack of expression of ISF 35 by the HeLa cells since FACS analysis of the infected HeLa cells showed cell surface expression of ISF 35 at levels similar to what is shown in FIG. 6.

While preferred method and apparatus embodiments have been shown and described, it will be apparent to one of ordinary skill in the art that numerous alterations may be made without departing from the spirit or scope of the invention. The invention is not to be limited except in accordance with the following claims and their legal equivalents.

What is claimed is:

1. A nucleic acid molecule encoding a chimeric CD154 polypeptide selected from the group of nucleic acid molecules consisting of ISF 30 (SEQ. ID. NO. 1), ISF 32 (SEQ. ID. NO. 3), ISF 34 (SEQ. ID. NO. 5), ISF 36 (SEQ. ID. NO 7), ISF 38 (SEQ. ID. NO. 9) and ISF 40 (SEQ. ID. NO. 11).

2. An expression vector, comprising the nucleic acid molecule of claim 1.

3. The expression vector of claim 2, further comprising viral DNA or bacterial DNA.

4. The expression vector of claim 3, wherein said viral DNA is selected from the group consisting of adenoviral DNA or retroviral DNA.

5. The expression vector of claim 4, wherein at least a portion of the vector comprises adenoviral DNA.

6. The expression vector of claim 2, further comprising a promoter region.

7. The expression vector of claim 6, further comprising a polyadenylation signal region.

8. A genetic construct comprising the nucleic acid molecule of claim 1 operatively linked to a promoter sequence and to a polyadenylation signal sequence.

9. A host cell, comprising an expression vector of claim 2 or a genetic construct of claim 8.

10. The host cell of claim 9, wherein the cell is a mammalian cell.

11. The host cell of claim 10, wherein the cell is a human CD40+ cell.

12. The host cell of claim 9, wherein the cell is a tumor cell.

13. The host cell of claim 9, wherein the cell is an antigen presenting cell.

14. A process for producing a chimeric CD154, comprising culturing a host cell of claim 9 under conditions suitable to effect expression of the protein.

15. A method for increasing the concentration of a ligand capable of binding to a CD154 receptor on the surface of a cell, comprising introducing into the cell an expression vector according to claim 2 encoding a chimeric CD154 according to claim 1, whereby the chimeric CD154 is less susceptible to cleavage from the surface of the cells than human CD154.

16. A nucleic acid molecule having a nucleotide sequence selected from the group consisting of SEQ. ID NOS. 1, 3, 5, 7, 9, and 11.

17. A nucleic acid molecule having a nucleotide sequence that encodes an amino acid sequence selected from the group consisting of SEQ. ID. NOS. 13, 15, 17, 19, 21, and 23.

\* \* \* \* \*

SEQUENCE LISTING

<160> NUMBER OF SEQ ID NOS: 28

<210> SEQ ID NO 1
<211> LENGTH: 783
<212> TYPE: DNA
<213> ORGANISM: Artificial sequence
<220> FEATURE:
<223> OTHER INFORMATION: Chimeric DNA construct ISF30

<400> SEQUENCE: 1

```
atgatagaaa catacagcca accttccccc agatccgtgg caactggact tccagcgagc      60
atgaagattt ttatgtattt acttactgtt ttccttatca cccaaatgat tggatctgtg     120 cttttttgctg tgtatcttca tagaagattg gataaggtcg aagaggaagt aaaccttcat    180
gaagattttg tattcataaa aaagctaaag agatgcaaca aaggagaagg atctttatcc    240
ttgctgaact gtgaggagat gagaaggcaa tttgaagacc ttgtcaagga tataacgtta    300
aacaaagaag agaaaaaaga aaacagcttt gaaatgcaaa gaggtgatga ggatcctcaa    360
attgcagcac acgttgtaag cgaagccaac agtaatgcag catccgttct acagtgggcc    420
aagaaaggat attataccat gaaaagcaac ttggtaaccc tggaaaatgg gaaacagctg    480
acggttaaaa gacaaggact ctattatatc tatgctcaag tcaccttctg ctctaatcgg    540
gagccttcga gtcaacgccc attcatcgtc ggcctctggc tgaagcccag cagtggatct    600
gagagaatct tactcaaggc ggcaaatacc cacagttcct cccagctttg cgagcagcag    660
tctgttcact tgggcggagt gtttgaatta caaccaggtg cttcggtgtt tgtcaatgtg    720
actgatccaa gccaagtgag ccatggcact ggcttcacgt cctttggctt actcaaactc    780
tga                                                                   783
```

<210> SEQ ID NO 2
<211> LENGTH: 759
<212> TYPE: DNA
<213> ORGANISM: Artificial sequence
<220> FEATURE:
<223> OTHER INFORMATION: Chimeric DNA construct ISF31

<400> SEQUENCE: 2

```
atgatcgaaa catacaacca aacttctccc cgatctgcgg ccactggact gcccatcagc      60
atgaaaattt ttatgtattt acttactgtt tttcttatca cccagatgat tgggtcagca     120 cttttttgctg tgtatcttca tagaaggctg gacaagatag aagatgaaag gaatcttcat    180
```

```
gaagattttg tattcatgaa acgatacag agatgcaaca caggagaaag atccttatcc    240
ttactgaact gtgaggagat taaaagccag tttgaaggct tgtgaagga tataatgtta    300 aacaaagagg agacgaagaa agatgaggat cctcaaattg cagcacacgt tgtaagcgaa    360
gccaacagta atgcagcatc cgttctacag tgggccaaga aaggatatta taccatgaaa    420
agcaacttgg taaccctgga aaatgggaaa cagctgacgg ttaaaagaca aggactctat    480
tatatctatg ctcaagtcac cttctgctct aatcggagc cttcgagtca acgcccattc    540
atcgtcggcc tctggctgaa gcccagcagt ggatctgaga gaatcttact caaggcggca    600
aatacccaca gttcctccca gctttgcgag cagcagtctg ttcacttggg cggagtgttt    660
gaattacaac caggtgcttc ggtgtttgtc aatgtgactg atccaagcca agtgagccat    720
ggcactggct tcacgtcctt tggcttactc aaactctga                          759

<210> SEQ ID NO 3
<211> LENGTH: 783
<212> TYPE: DNA
<213> ORGANISM: Artificial sequence
<220> FEATURE:
<223> OTHER INFORMATION: Chimeric DNA construct ISF32

<400> SEQUENCE: 3
atgatagaaa catacagcca accttccccc agatccgtgg caactggact tccagcgagc     60
atgaagattt ttatgtattt acttactgtt ttccttatca cccaaatgat tggatctgtg    120 cttttttgctg tgtatcttca tagaagattg gataaggtcg aagaggaagt aaaccttcat    180
gaagattttg tattcataaa aaagctaaag agatgcaaca aaggagaagg atctttatcc    240
ttgctgaact gtgaggagat gagaaggcaa tttgaagacc ttgtcaagga tataacgtta    300
aacaaagaag agaaaaaaga aaacagcttt gaaatgcaaa gaggtgatga ggatcctcaa    360
attgcagcac acgttgtaag cgaagccaac agtaatgcag catccgttct acagtgggcc    420
aagaaaggat attataccat gaaaagcaac ttggtaaccc tggaaaatgg gaaacagctg    480
acggttaaaa gacaaggact ctattatatc tatgctcaag tcaccttctg ctctaatcgg    540
gaggcttcga gtcaagcccc attcatcgtc ggcctctggc tgaagcccag cagtggatct    600
gagagaatct tactcaaggc ggcaaatacc cacagttcct cccagctttg cgagcagcag    660
tctgttcact gggcggagt gtttgaatta caaccaggtg cttcggtgtt tgtcaatgtg    720
actgatccaa gccaagtgag ccatggcact ggcttcacgt cctttggctt actcaaactc    780
tga                                                                  783

<210> SEQ ID NO 4
<211> LENGTH: 759
<212> TYPE: DNA
<213> ORGANISM: Artificial sequence
<220> FEATURE:
<223> OTHER INFORMATION: Chimeric DNA construct ISF33

<400> SEQUENCE: 4
atgatcgaaa catacaacca aacttctccc cgatctgcgg ccactggact gcccatcagc     60
atgaaaattt ttatgtattt acttactgtt tttcttatca cccagatgat tgggtcagca    120 cttttttgctg tgtatcttca tagaaggctg acaagatag aagatgaaag gaatcttcat    180
gaagattttg tattcatgaa acgatacag agatgcaaca caggagaaag atccttatcc    240
ttactgaact gtgaggagat taaaagccag tttgaaggct tgtgaagga tataatgtta    300 aacaaagagg agacgaagaa agatgaggat cctcaaattg cagcacacgt tgtaagcgaa    360
```

-continued

```
gccaacagta atgcagcatc cgttctacag tgggccaaga aaggatatta taccatgaaa    420
agcaacttgg taaccctgga aaatgggaaa cagctgacgg ttaaaagaca aggactctat    480
tatatctatg ctcaagtcac cttctgctct aatcgggagg cttcgagtca agccccattc    540
atcgtcggcc tctggctgaa gcccagcagt ggatctgaga gaatcttact caaggcggca    600
aatacccaca gttcctccca gctttgcgag cagcagtctg ttcacttggg cggagtgttt    660
gaattacaac aggtgcttc ggtgtttgtc aatgtgactg atccaagcca agtgagccat    720
ggcactggct tcacgtcctt tggcttactc aaactctga                           759
```

<210> SEQ ID NO 5
<211> LENGTH: 783
<212> TYPE: DNA
<213> ORGANISM: Artificial sequence
<220> FEATURE:
<223> OTHER INFORMATION: Chimeric DNA construct ISF34

<400> SEQUENCE: 5

```
atgatagaaa catacagcca accttccccc agatccgtgg caactggact tccagcgagc     60
atgaagattt ttatgtattt acttactgtt ttccttatca cccaaaatgat tggatctgtg    120
cttttttgctg tgtatcttca tagaagattg ataaggtcg aagaggaagt aaaccttcat    180
gaagattttg tattcataaa aaagctaaag agatgcaaca aaggagaagg atctttatcc    240
ttgctgaact gtgaggagat gagaaggcaa tttgaagacc ttgtcaagga tataacgtta    300
aacaaagaag agaaaaaaga aaacagcttt gaaatgcaaa gaggtgatga ggatcctcaa    360
attgcagcac acgttgtaag cgaagccaac agtaatgcag catccgttct acagtgggcc    420
aagaaaggat attataccat gaaagcaac ttggtaaccc tggaaaatgg aaacagctg     480
acggttaaaa gacaaggact ctattatatc tatgctcaag tcaccttctg ctctaatcgg    540
gaggcttcga gtcaagcccc attcatcgtc ggcctctggc tgaagcccag cagtggatct    600
gagagaatct tactcaaggc ggcaaatacc cacagttcct cccagctttg cgagcagcag    660
tctattcact gggcggagt gtttgaatta caaccaggtg cttcggtgtt tgtcaatgtg    720
actgatccaa gccaagtgag ccatggcact ggcttcacgt cctttggctt actcaaactc    780
tga                                                                  783
```

<210> SEQ ID NO 6
<211> LENGTH: 759
<212> TYPE: DNA
<213> ORGANISM: Artificial sequence
<220> FEATURE:
<223> OTHER INFORMATION: Chimeric DNA construct ISF35

<400> SEQUENCE: 6

```
atgatcgaaa catacaacca aacttctccc cgatctgcgg ccactggact gcccatcagc     60
atgaaaattt ttatgtattt acttactgtt tttcttatca cccagatgat tgggtcagca    120
cttttttgctg tgtatcttca tagaaggctg acaagatag aagatgaaag gaatcttcat    180
gaagattttg tattcatgaa aacgatacag agatgcaaca caggagaaag atccttatcc    240
ttactgaact gtgaggagat taaaagccag tttgaaggct tgtgaagga tataatgtta    300
aacaaagagg agacgaagaa agatgaggat cctcaaattg cagcacacgt tgtaagcgaa    360
gccaacagta atgcagcatc cgttctacag tgggccaaga aaggatatta taccatgaaa    420
agcaacttgg taaccctgga aaatgggaaa cagctgacgg ttaaaagaca aggactctat    480
tatatctatg ctcaagtcac cttctgctct aatcgggagg cttcgagtca agccccattc    540
```

| | |
|---|---:|
| atcgtcggcc tctggctgaa gcccagcagt ggatctgaga gaatcttact caaggcggca | 600 |
| aatacccaca gttcctccca gctttgcgag cagcagtcta ttcacttggg cggagtgttt | 660 |
| gaattacaac caggtgcttc ggtgtttgtc aatgtgactg atccaagcca agtgagccat | 720 |
| ggcactggct tcacgtcctt tggcttactc aaactctga | 759 |

<210> SEQ ID NO 7
<211> LENGTH: 783
<212> TYPE: DNA
<213> ORGANISM: Artificial sequence
<220> FEATURE:
<223> OTHER INFORMATION: Chimeric construct ISF36

<400> SEQUENCE: 7

| | |
|---|---:|
| atgatagaaa catacagcca accttccccc agatccgtgg caactggact tccagcgagc | 60 |
| atgaagattt ttatgtattt acttactgtt ttccttatca cccaaatgat tggatctgtg | 120 |
| cttttttgctg tgtatcttca tagaagattg gataaggtcg aagaggaagt aaaccttcat | 180 |
| gaagattttg tattcataaa aaagctaaag agatgcaaca aggagaagg atctttatcc | 240 |
| ttgctgaact gtgaggagat gagaaggcaa tttgaagacc ttgtcaagga tataacgtta | 300 |
| aacaaagaag agaaaaaaga aaacagcttt gaaatgcaaa gaggtgatga ggatcctcaa | 360 |
| attgcagcac acgttgtaag cgaagccaac agtaatgcag catccgttct acagtggggcc | 420 |
| aagaaaggat attataccat gaaaagcaac ttggtaaccc tggaaaatgg gaaacagctg | 480 |
| acggttaaaa acaaggact ctattatatc tatgctcaag tcaccttctg ctctaatcgg | 540 |
| gaggcttcga gtcaagcccc attcatcgtc ggcctctggc tgaagcccag cagtggatct | 600 |
| gagagaatct tactcaaggc ggcaaatacc cacagttccg ccaagccttg cgggcagcag | 660 |
| tctattcact gggcggagt gtttgaatta caaccaggtg cttcgtgttt tgtcaatgtg | 720 |
| actgatccaa gccaagtgag ccatggcact ggcttcacgt cctttggctt actcaaactc | 780 |
| tga | 783 |

<210> SEQ ID NO 8
<211> LENGTH: 759
<212> TYPE: DNA
<213> ORGANISM: Artificial sequence
<220> FEATURE:
<223> OTHER INFORMATION: Chimeric DNA construct ISF37

<400> SEQUENCE: 8

| | |
|---|---:|
| atgatcgaaa catacaacca aacttctccc cgatctgcgg ccactggact gcccatcagc | 60 |
| atgaaaattt ttatgtattt acttactgtt tttcttatca cccagatgat tgggtcagca | 120 |
| cttttttgctg tgtatcttca tagaaggctg acaagatag aagatgaaag gaatcttcat | 180 |
| gaagattttg tattcatgaa aacgatacag agatgcaaca caggagaaag atccttatcc | 240 |
| ttactgaact gtgaggagat taaaagccag tttgaaggct tgtgaagga tataatgtta | 300 |
| aacaaagagg agacgaagaa agatgaggat cctcaaattg cagcacacgt tgtaagcgaa | 360 |
| gccaacagta atgcagcatc cgttctacag tgggccaaga aaggatatta taccatgaaa | 420 |
| agcaacttgg taaccctgga aaatgggaaa cagctgacgg ttaaaagaca aggactctat | 480 |
| tatatctatg ctcaagtcac cttctgctct aatcggagg cttcgagtca agccccattc | 540 |
| atcgtcggcc tctggctgaa gcccagcagt ggatctgaga gaatcttact caaggcggca | 600 |
| aatacccaca gttccgccaa gccttgcggg cagcagtcta ttcacttggg cggagtgttt | 660 |
| gaattacaac caggtgcttc ggtgtttgtc aatgtgactg atccaagcca agtgagccat | 720 |

```
ggcactggct tcacgtcctt tggcttactc aaactctga                    759
```

<210> SEQ ID NO 9
<211> LENGTH: 783
<212> TYPE: DNA
<213> ORGANISM: Artificial sequence
<220> FEATURE:
<223> OTHER INFORMATION: Chimeric DNA construct ISF38

<400> SEQUENCE: 9

```
atgatagaaa catacagcca accttccccc agatccgtgg caactggact tccagcgagc    60
atgaagattt ttatgtattt acttactgtt ttccttatca cccaaatgat tggatctgtg   120
cttttttgctg tgtatcttca tagaagattg ataaggtcg aagaggaagt aaaccttcat   180
gaagattttg tattcataaa aaagctaaag agatgcaaca aggagaagg atctttatcc   240
ttgctgaact gtgaggagat gagaaggcaa tttgaagacc ttgtcaagga tataacgtta   300
aacaaagaag agaaaaaaga aaacagcttt gaaatgcaaa gaggtgatga ggatcctcaa   360
attgcagcac acgttgtaag cgaagccaac agtaatgcag catccgttct acagtgggcc   420
aagaaaggat attataccat gaaagcaac ttggtaaccc tggaaaatgg gaaacagctg   480
acggttaaaa gacaaggact ctattatatc tatgctcaag tcaccttctg ctctaatcgg   540
gagccttcga gtcaacgccc attcatcgtc ggcctctggc tgaagcccag cagtggatct   600
gagagaatct tactcaaggc ggcaaatacc cacagttcct cccagctttg cgagcagcag   660
tctattcact gggcggagt gtttgaatta caaccaggtg cttcggtgtt tgtcaatgtg   720
actgatccaa gccaagtgag ccatggcact ggcttcacgt cctttggctt actcaaactc   780
tga                                                                783
```

<210> SEQ ID NO 10
<211> LENGTH: 759
<212> TYPE: DNA
<213> ORGANISM: Artificial sequence
<220> FEATURE:
<223> OTHER INFORMATION: Chimeric DNA construct ISF39

<400> SEQUENCE: 10

```
atgatcgaaa catacaacca aacttctccc cgatctgcgg ccactggact gcccatcagc    60
atgaaaattt ttatgtattt acttactgtt tttcttatca cccagatgat tgggtcagca   120
cttttttgctg tgtatcttca tagaaggctg acaagatag aagatgaaag gaatcttcat   180
gaagattttg tattcatgaa aacgatacag agatgcaaca caggagaaag atccttatcc   240
ttactgaact gtgaggagat taaaagccag tttgaaggct tgtgaagga tataatgtta   300
aacaaagagg agacgaagaa agatgaggat cctcaaattg cagcacacgt tgtaagcgaa   360
gccaacagta atgcagcatc cgttctacag tgggccaaga aaggatatta ccatgaaa    420
agcaacttgg taaccctgga aaatgggaaa cagctgacgg ttaaaagaca aggactctat   480
tatatctatg ctcaagtcac cttctgctct aatcgggagc cttcgagtca acgccattc   540
atcgtcggcc tctggctgaa gcccagcagt ggatctgaga gaatcttact caaggcggca   600
atacccaca gttcctccca gctttgcgag cagcagtcta ttcacttggg cggagtgttt   660
gaattacaac caggtgcttc ggtgtttgtc aatgtgactg atccaagcca agtgagccat   720
ggcactggct tcacgtcctt tggcttactc aaactctga                         759
```

<210> SEQ ID NO 11
<211> LENGTH: 783
<212> TYPE: DNA

<213> ORGANISM: Artificial sequence
<220> FEATURE:
<223> OTHER INFORMATION: Chimeric DNA construct ISF40

<400> SEQUENCE: 11

```
atgatagaaa catacagcca accttccccc agatccgtgg caactggact tccagcgagc      60
atgaagattt ttatgtattt acttactgtt tccttatca cccaaatgat tggatctgtg     120
cttttttgctg tgtatcttca tagaagattg gataaggtcg aagaggaagt aaaccttcat    180
gaagattttg tattcataaa aaagctaaag agatgcaaca aggagaagg atctttatcc     240
ttgctgaact gtgaggagat gagaaggcaa tttgaagacc ttgtcaagga tataacgtta    300
aacaaagaag agaaaaaaga aaacagcttt gaaatgcaaa gaggtgatga ggatcctcaa    360
attgcagcac acgttgtaag cgaagccaac agtaatgcag catccgttct acagtgggcc    420
aagaaaggat attataccat gaaaagcaac ttggtaaccc tggaaaatgg gaaacagctg    480
acggttaaaa acaaggact ctattatatc tatgctcaag tcaccttctg ctctaatcgg    540
gagccttcga gtcaacgccc attcatcgtc ggcctctggc tgaagcccag cagtggatct    600
gagagaatct tactcaaggc ggcaaatacc cacagttccg ccaagccttg cgggcagcag    660
tctattcact gggcggagt gtttgaatta caaccaggtg cttcggtgtt tgtcaatgtg    720
actgatccaa gccaagtgag ccatggcact ggcttcacgt cctttggctt actcaaactc    780
tga                                                                  783
```

<210> SEQ ID NO 12
<211> LENGTH: 759
<212> TYPE: DNA
<213> ORGANISM: Artificial sequence
<220> FEATURE:
<223> OTHER INFORMATION: Chimeric DNA construct ISF41

<400> SEQUENCE: 12

```
atgatcgaaa catacaacca aacttctccc cgatctgcgg ccactggact gcccatcagc      60
atgaaaattt ttatgtattt acttactgtt tttcttatca cccagatgat tgggtcagca    120
cttttttgctg tgtatcttca tagaaggctg gacaagatag aagatgaaag gaatcttcat    180
gaagattttg tattcatgaa aacgatacag agatgcaaca caggagaaag atccttatcc    240
ttactgaact gtgaggagat taaaagccag tttgaaggct tgtgaagga tataatgtta    300
aacaaagagg agacgaagaa agatgaggat cctcaaattg cagcacacgt tgtaagcgaa    360
gccaacagta atgcagcatc cgttctacag tgggccaaga aaggatatta ccatgaaaa    420
agcaacttgg taaccctgga aaatgggaaa cagctgacgg ttaaaagaca aggactctat    480
tatatctatg ctcaagtcac cttctgctct aatcgggagc cttcgagtca acgcccattc    540
atcgtcggcc tctggctgaa gcccagcagt ggatctgaga atcttact caaggcggca    600
aatacccaca gttccgccaa gccttgcggg cagcagtcta ttcactgggg cggagtgttt    660
gaattacaac aggtgcttc ggtgtttgtc aatgtgactg atccaagcca agtgagccat    720
ggcactggct tcacgtcctt tggcttactc aaactctga                          759
```

<210> SEQ ID NO 13
<211> LENGTH: 260
<212> TYPE: PRT
<213> ORGANISM: Artificial sequence
<220> FEATURE:
<223> OTHER INFORMATION: Chimeric CD154 polypeptide encoded by the
      DNA sequence of SEQ ID NO:1

<400> SEQUENCE: 13

Met Ile Glu Thr Tyr Ser Gln Pro Ser Arg Ser Val Ala Thr Gly
1               5                   10                  15

Leu Pro Ala Ser Met Lys Ile Phe Met Tyr Leu Leu Thr Val Phe Leu
                20                  25                  30

Ile Thr Gln Met Ile Gly Ser Val Leu Phe Ala Val Tyr Leu His Arg
            35                  40                  45

Arg Leu Asp Lys Val Glu Glu Val Asn Leu His Glu Asp Phe Val
    50                  55                  60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
                100                 105                 110

Gln Arg Gly Asp Glu Asp Pro Gln Ile Ala Ala His Val Val Ser Glu
            115                 120                 125

Ala Asn Ser Asn Ala Ala Ser Val Leu Gln Trp Ala Lys Lys Gly Tyr
    130                 135                 140

Tyr Thr Met Lys Ser Asn Leu Val Thr Leu Glu Asn Gly Lys Gln Leu
145                 150                 155                 160

Thr Val Lys Arg Gln Gly Leu Tyr Tyr Ile Tyr Ala Gln Val Thr Phe
                165                 170                 175

Cys Ser Asn Arg Glu Pro Ser Ser Gln Arg Pro Phe Ile Val Gly Leu
                180                 185                 190

Trp Leu Lys Pro Ser Ser Gly Ser Glu Arg Ile Leu Leu Lys Ala Ala
            195                 200                 205

Asn Thr His Ser Ser Gln Leu Cys Glu Gln Gln Ser Val His Leu
    210                 215                 220

Gly Gly Val Phe Glu Leu Gln Pro Gly Ala Ser Val Phe Val Asn Val
225                 230                 235                 240

Thr Asp Pro Ser Gln Val Ser His Gly Thr Gly Phe Thr Ser Phe Gly
                245                 250                 255

Leu Leu Lys Leu
            260

<210> SEQ ID NO 14
<211> LENGTH: 252
<212> TYPE: PRT
<213> ORGANISM: Artificial sequence
<220> FEATURE:
<223> OTHER INFORMATION: Chimeric CD154 polypeptide encoded by the
      DNA sequence of SEQ ID NO:2

<400> SEQUENCE: 14

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
                20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

```
Asp Ile Met Leu Asn Lys Glu Glu Thr Lys Lys Asp Glu Asp Pro Gln
            100                 105                 110
Ile Ala Ala His Val Val Ser Glu Ala Asn Ser Asn Ala Ala Ser Val
        115                 120                 125
Leu Gln Trp Ala Lys Lys Gly Tyr Tyr Thr Met Lys Ser Asn Leu Val
    130                 135                 140
Thr Leu Glu Asn Gly Lys Gln Leu Thr Val Lys Arg Gln Gly Leu Tyr
145                 150                 155                 160
Tyr Ile Tyr Ala Gln Val Thr Phe Cys Ser Asn Arg Glu Pro Ser Ser
                165                 170                 175
Gln Arg Pro Phe Ile Val Gly Leu Trp Leu Lys Pro Ser Ser Gly Ser
            180                 185                 190
Glu Arg Ile Leu Leu Lys Ala Ala Asn Thr His Ser Ser Ser Gln Leu
        195                 200                 205
Cys Glu Gln Gln Ser Val His Leu Gly Gly Val Phe Glu Leu Gln Pro
    210                 215                 220
Gly Ala Ser Val Phe Val Asn Val Thr Asp Pro Ser Gln Val Ser His
225                 230                 235                 240
Gly Thr Gly Phe Thr Ser Phe Gly Leu Leu Lys Leu
                245                 250
```

<210> SEQ ID NO 15
<211> LENGTH: 260
<212> TYPE: PRT
<213> ORGANISM: Artificial sequence
<220> FEATURE:
<223> OTHER INFORMATION: Chimeric CD154 polypeptide encoded by the
      DNA sequence of SEQ ID NO:3

<400> SEQUENCE: 15

```
Met Ile Glu Thr Tyr Ser Gln Pro Ser Pro Arg Ser Val Ala Thr Gly
1               5                   10                  15
Leu Pro Ala Ser Met Lys Ile Phe Met Tyr Leu Leu Thr Val Phe Leu
            20                  25                  30
Ile Thr Gln Met Ile Gly Ser Val Leu Phe Ala Val Tyr Leu His Arg
        35                  40                  45
Arg Leu Asp Lys Val Glu Glu Val Asn Leu His Glu Asp Phe Val
    50                  55                  60
Phe Ile Lys Lys Leu Lys Arg Cys Asn Lys Gly Glu Gly Ser Leu Ser
65                  70                  75                  80
Leu Leu Asn Cys Glu Glu Met Arg Arg Gln Phe Glu Asp Leu Val Lys
                85                  90                  95
Asp Ile Thr Leu Asn Lys Glu Glu Lys Lys Glu Asn Ser Phe Glu Met
            100                 105                 110
Gln Arg Gly Asp Glu Asp Pro Gln Ile Ala Ala His Val Val Ser Glu
        115                 120                 125
Ala Asn Ser Asn Ala Ala Ser Val Leu Gln Trp Ala Lys Lys Gly Tyr
    130                 135                 140
Tyr Thr Met Lys Ser Asn Leu Val Thr Leu Glu Asn Gly Lys Gln Leu
145                 150                 155                 160
Thr Val Lys Arg Gln Gly Leu Tyr Tyr Ile Tyr Ala Gln Val Thr Phe
                165                 170                 175
Cys Ser Asn Arg Glu Ala Ser Ser Gln Ala Pro Phe Ile Val Gly Leu
            180                 185                 190
Trp Leu Lys Pro Ser Ser Gly Ser Glu Arg Ile Leu Leu Lys Ala Ala
        195                 200                 205
```

```
Asn Thr His Ser Ser Gln Leu Cys Glu Gln Gln Ser Val His Leu
        210                 215                 220
Gly Gly Val Phe Glu Leu Gln Pro Gly Ala Ser Val Phe Val Asn Val
225                 230                 235                 240
Thr Asp Pro Ser Gln Val Ser His Gly Thr Gly Phe Thr Ser Phe Gly
                245                 250                 255
Leu Leu Lys Leu
        260

<210> SEQ ID NO 16
<211> LENGTH: 252
<212> TYPE: PRT
<213> ORGANISM: Artificial sequence
<220> FEATURE:
<223> OTHER INFORMATION: Chimeric CD154 polypeptide encoded by the
      DNA sequence of SEQ ID NO:4

<400> SEQUENCE: 16

Met Ile Glu Thr Tyr Asn Gln Thr Ser Pro Arg Ser Ala Ala Thr Gly
1               5                   10                  15
Leu Pro Ile Ser Met Lys Ile Phe Met Tyr Leu Leu Thr Val Phe Leu
            20                  25                  30
Ile Thr Gln Met Ile Gly Ser Ala Leu Phe Ala Val Tyr Leu His Arg
        35                  40                  45
Arg Leu Asp Lys Ile Glu Asp Glu Arg Asn Leu His Glu Asp Phe Val
    50                  55                  60
Phe Met Lys Thr Ile Gln Arg Cys Asn Thr Gly Glu Arg Ser Leu Ser
65                  70                  75                  80
Leu Leu Asn Cys Glu Glu Ile Lys Ser Gln Phe Glu Gly Phe Val Lys
                85                  90                  95
Asp Ile Met Leu Asn Lys Glu Glu Thr Lys Lys Asp Glu Asp Pro Gln
            100                 105                 110
Ile Ala Ala His Val Val Ser Glu Ala Asn Ser Asn Ala Ala Ser Val
        115                 120                 125
Leu Gln Trp Ala Lys Lys Gly Tyr Tyr Thr Met Lys Ser Asn Leu Val
    130                 135                 140
Thr Leu Glu Asn Gly Lys Gln Leu Thr Val Lys Arg Gln Gly Leu Tyr
145                 150                 155                 160
Tyr Ile Tyr Ala Gln Val Thr Phe Cys Ser Asn Arg Glu Ala Ser Ser
                165                 170                 175
Gln Ala Pro Phe Ile Val Gly Leu Trp Leu Lys Pro Ser Ser Gly Ser
            180                 185                 190
Glu Arg Ile Leu Leu Lys Ala Ala Asn Thr His Ser Ser Ser Gln Leu
        195                 200                 205
Cys Glu Gln Gln Ser Val His Leu Gly Gly Val Phe Glu Leu Gln Pro
    210                 215                 220
Gly Ala Ser Val Phe Val Asn Val Thr Asp Pro Ser Gln Val Ser His
225                 230                 235                 240
Gly Thr Gly Phe Thr Ser Phe Gly Leu Leu Lys Leu
                245                 250

<210> SEQ ID NO 17
<211> LENGTH: 260
<212> TYPE: PRT
<213> ORGANISM: Artificial sequence
<220> FEATURE:
<223> OTHER INFORMATION: Chimeric CD154 polypeptide encoded by the
      DNA sequence of SEQ ID NO:5
```

<400> SEQUENCE: 17

```
Met Ile Glu Thr Tyr Ser Gln Pro Ser Pro Arg Ser Val Ala Thr Gly
  1               5                  10                  15

Leu Pro Ala Ser Met Lys Ile Phe Met Tyr Leu Leu Thr Val Phe Leu
             20                  25                  30

Ile Thr Gln Met Ile Gly Ser Val Leu Phe Ala Val Tyr Leu His Arg
         35                  40                  45

Arg Leu Asp Lys Val Glu Glu Val Asn Leu His Glu Asp Phe Val
     50                  55                  60

Phe Ile Lys Lys Leu Lys Arg Cys Asn Lys Gly Glu Gly Ser Leu Ser
 65                  70                  75                  80

Leu Leu Asn Cys Glu Glu Met Arg Arg Gln Phe Glu Asp Leu Val Lys
                 85                  90                  95

Asp Ile Thr Leu Asn Lys Glu Glu Lys Lys Glu Asn Ser Phe Glu Met
             100                 105                 110

Gln Arg Gly Asp Glu Asp Pro Gln Ile Ala Ala His Val Val Ser Glu
         115                 120                 125

Ala Asn Ser Asn Ala Ala Ser Val Leu Gln Trp Ala Lys Lys Gly Tyr
    130                 135                 140

Tyr Thr Met Lys Ser Asn Leu Val Thr Leu Glu Asn Gly Lys Gln Leu
145                 150                 155                 160

Thr Val Lys Arg Gln Gly Leu Tyr Tyr Ile Tyr Ala Gln Val Thr Phe
                165                 170                 175

Cys Ser Asn Arg Glu Ala Ser Ser Gln Ala Pro Phe Ile Val Gly Leu
            180                 185                 190

Trp Leu Lys Pro Ser Ser Gly Ser Glu Arg Ile Leu Leu Lys Ala Ala
        195                 200                 205

Asn Thr His Ser Ser Ser Gln Leu Cys Glu Gln Gln Ser Ile His Leu
210                 215                 220

Gly Gly Val Phe Glu Leu Gln Pro Gly Ala Ser Val Phe Val Asn Val
225                 230                 235                 240

Thr Asp Pro Ser Gln Val Ser His Gly Thr Gly Phe Thr Ser Phe Gly
                245                 250                 255

Leu Leu Lys Leu
            260
```

<210> SEQ ID NO 18
<211> LENGTH: 252
<212> TYPE: PRT
<213> ORGANISM: Artificial sequence
<220> FEATURE:
<223> OTHER INFORMATION: Chimeric CD154 polypeptide encoded by the DNA sequence of SEQ ID NO:6

<400> SEQUENCE: 18

```
Met Ile Glu Thr Tyr Asn Gln Thr Ser Pro Arg Ser Ala Ala Thr Gly
  1               5                  10                  15

Leu Pro Ile Ser Met Lys Ile Phe Met Tyr Leu Leu Thr Val Phe Leu
             20                  25                  30

Ile Thr Gln Met Ile Gly Ser Ala Leu Phe Ala Val Tyr Leu His Arg
         35                  40                  45

Arg Leu Asp Lys Ile Glu Asp Glu Arg Asn Leu His Glu Asp Phe Val
     50                  55                  60

Phe Met Lys Thr Ile Gln Arg Cys Asn Thr Gly Glu Arg Ser Leu Ser
 65                  70                  75                  80
```

```
Leu Leu Asn Cys Glu Glu Ile Lys Ser Gln Phe Glu Gly Phe Val Lys
                85                  90                  95

Asp Ile Met Leu Asn Lys Glu Thr Lys Lys Asp Glu Asp Pro Gln
            100                 105                 110

Ile Ala Ala His Val Val Ser Glu Ala Asn Ser Asn Ala Ala Ser Val
            115                 120                 125

Leu Gln Trp Ala Lys Lys Gly Tyr Tyr Thr Met Lys Ser Asn Leu Val
            130                 135                 140

Thr Leu Glu Asn Gly Lys Gln Leu Thr Val Lys Arg Gln Gly Leu Tyr
145                 150                 155                 160

Tyr Ile Tyr Ala Gln Val Thr Phe Cys Ser Asn Arg Glu Ala Ser Ser
                165                 170                 175

Gln Ala Pro Phe Ile Val Gly Leu Trp Leu Lys Pro Ser Ser Gly Ser
            180                 185                 190

Glu Arg Ile Leu Leu Lys Ala Ala Asn Thr His Ser Ser Ser Gln Leu
            195                 200                 205

Cys Glu Gln Gln Ser Ile His Leu Gly Gly Val Phe Glu Leu Gln Pro
    210                 215                 220

Gly Ala Ser Val Phe Val Asn Val Thr Asp Pro Ser Gln Val Ser His
225                 230                 235                 240

Gly Thr Gly Phe Thr Ser Phe Gly Leu Leu Lys Leu
                245                 250

<210> SEQ ID NO 19
<211> LENGTH: 260
<212> TYPE: PRT
<213> ORGANISM: Artificial sequence
<220> FEATURE:
<223> OTHER INFORMATION: Chimeric CD154 polypeptide encoded by the
      DNA sequence of SEQ ID NO:7

<400> SEQUENCE: 19

Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg
            35                  40                  45

Arg Leu Asp Lys Val Glu Glu Glu Val Asn Leu His Glu Asp Phe Val
    50                  55                  60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
            100                 105                 110

Gln Arg Gly Asp Glu Asp Pro Gln Ile Ala Ala His Val Val Ser Glu
            115                 120                 125

Ala Asn Ser Asn Ala Ala Ser Val Leu Gln Trp Ala Lys Lys Gly Tyr
130                 135                 140

Tyr Thr Met Lys Ser Asn Leu Val Thr Leu Glu Asn Gly Lys Gln Leu
145                 150                 155                 160

Thr Val Lys Arg Gln Gly Leu Tyr Tyr Ile Tyr Ala Gln Val Thr Phe
                165                 170                 175

Cys Ser Asn Arg Glu Ala Ser Ser Gln Ala Pro Phe Ile Val Gly Leu
            180                 185                 190
```

```
Trp Leu Lys Pro Ser Ser Gly Ser Glu Arg Ile Leu Leu Lys Ala Ala
            195                 200                 205

Asn Thr His Ser Ser Ala Lys Pro Cys Gly Gln Gln Ser Ile His Leu
            210                 215                 220

Gly Gly Val Phe Glu Leu Gln Pro Gly Ala Ser Cys Phe Val Asn Val
225                 230                 235                 240

Thr Asp Pro Ser Gln Val Ser His Gly Thr Gly Phe Thr Ser Phe Gly
            245                 250                 255

Leu Leu Lys Leu
            260

<210> SEQ ID NO 20
<211> LENGTH: 252
<212> TYPE: PRT
<213> ORGANISM: Artificial sequence
<220> FEATURE:
<223> OTHER INFORMATION: Chimeric CD154 polypeptide encoded by the
      DNA sequence of SEQ ID NO:8

<400> SEQUENCE: 20

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Asp Glu Asp Pro Gln
            100                 105                 110

Ile Ala Ala His Val Val Ser Glu Ala Asn Ser Asn Ala Ala Ser Val
        115                 120                 125

Leu Gln Trp Ala Lys Lys Gly Tyr Tyr Thr Met Lys Ser Asn Leu Val
    130                 135                 140

Thr Leu Glu Asn Gly Lys Gln Leu Thr Val Lys Arg Gln Gly Leu Tyr
145                 150                 155                 160

Tyr Ile Tyr Ala Gln Val Thr Phe Cys Ser Asn Arg Glu Ala Ser Ser
                165                 170                 175

Gln Ala Pro Phe Ile Val Gly Leu Trp Leu Lys Pro Ser Ser Gly Ser
            180                 185                 190

Glu Arg Ile Leu Leu Lys Ala Ala Asn Thr His Ser Ser Ala Lys Pro
        195                 200                 205

Cys Gly Gln Gln Ser Ile His Leu Gly Gly Val Phe Glu Leu Gln Pro
    210                 215                 220

Gly Ala Ser Val Phe Val Asn Val Thr Asp Pro Ser Gln Val Ser His
225                 230                 235                 240

Gly Thr Gly Phe Thr Ser Phe Gly Leu Leu Lys Leu
                245                 250

<210> SEQ ID NO 21
<211> LENGTH: 260
<212> TYPE: PRT
<213> ORGANISM: Artificial sequence
<220> FEATURE:
```

-continued

```
<223> OTHER INFORMATION: Chimeric CD154 polypeptide encoded by the
      DNA sequence of SEQ ID NO:9

<400> SEQUENCE: 21

Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg
        35                  40                  45

Arg Leu Asp Lys Val Glu Glu Val Asn Leu His Glu Asp Phe Val
    50                  55                  60

Phe Ile Lys Lys Leu Lys Arg Cys Asn Lys Gly Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
            100                 105                 110

Gln Arg Gly Asp Glu Asp Pro Gln Ile Ala Ala His Val Val Ser Glu
        115                 120                 125

Ala Asn Ser Asn Ala Ala Ser Val Leu Gln Trp Ala Lys Lys Gly Tyr
    130                 135                 140

Tyr Thr Met Lys Ser Asn Leu Val Thr Leu Glu Asn Gly Lys Gln Leu
145                 150                 155                 160

Thr Val Lys Arg Gln Gly Leu Tyr Tyr Ile Tyr Ala Gln Val Thr Phe
                165                 170                 175

Cys Ser Asn Arg Glu Pro Ser Ser Gln Arg Pro Phe Ile Val Gly Leu
            180                 185                 190

Trp Leu Lys Pro Ser Ser Gly Ser Glu Arg Ile Leu Leu Lys Ala Ala
        195                 200                 205

Asn Thr His Ser Ser Ser Gln Leu Cys Glu Gln Gln Ser Ile His Leu
    210                 215                 220

Gly Gly Val Phe Glu Leu Gln Pro Gly Ala Ser Val Phe Val Asn Val
225                 230                 235                 240

Thr Asp Pro Ser Gln Val Ser His Gly Thr Gly Phe Thr Ser Phe Gly
                245                 250                 255

Leu Leu Lys Leu
        260

<210> SEQ ID NO 22
<211> LENGTH: 252
<212> TYPE: PRT
<213> ORGANISM: Artificial sequence
<220> FEATURE:
<223> OTHER INFORMATION: Chimeric CD154 polypeptide encoded by the
      DNA sequence of SEQ ID NO:10

<400> SEQUENCE: 22

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
```

```
                65                  70                  75                  80
Leu Leu Asn Cys Glu Glu Ile Lys Ser Gln Phe Glu Gly Phe Val Lys
                    85                  90                  95
Asp Ile Met Leu Asn Lys Glu Thr Lys Lys Asp Glu Asp Pro Gln
                    100                 105                 110
Ile Ala Ala His Val Val Ser Glu Ala Asn Ser Asn Ala Ala Ser Val
                    115                 120                 125
Leu Gln Trp Ala Lys Lys Gly Tyr Tyr Thr Met Lys Ser Asn Leu Val
            130                 135                 140
Thr Leu Glu Asn Gly Lys Gln Leu Thr Val Lys Arg Gln Gly Leu Tyr
145                 150                 155                 160
Tyr Ile Tyr Ala Gln Val Thr Phe Cys Ser Asn Arg Glu Pro Ser Ser
                    165                 170                 175
Gln Arg Pro Phe Ile Val Gly Leu Trp Leu Lys Pro Ser Ser Gly Ser
                    180                 185                 190
Glu Arg Ile Leu Leu Lys Ala Ala Asn Thr His Ser Ser Ser Gln Leu
                    195                 200                 205
Cys Glu Gln Gln Ser Ile His Leu Gly Gly Val Phe Glu Leu Gln Pro
            210                 215                 220
Gly Ala Ser Val Phe Val Asn Val Thr Asp Pro Ser Gln Val Ser His
225                 230                 235                 240
Gly Thr Gly Phe Thr Ser Phe Gly Leu Leu Lys Leu
                    245                 250

<210> SEQ ID NO 23
<211> LENGTH: 260
<212> TYPE: PRT
<213> ORGANISM: Artificial Sequence
<220> FEATURE:
<223> OTHER INFORMATION: Chimeric CD154 polypeptide encoded by the
      DNA sequence of SEQ ID NO:11

<400> SEQUENCE: 23

Met Ile Glu Thr Tyr Ser Gln Pro Ser Pro Arg Ser Val Ala Thr Gly
1               5                   10                  15
Leu Pro Ala Ser Met Lys Ile Phe Met Tyr Leu Leu Thr Val Phe Leu
                    20                  25                  30
Ile Thr Gln Met Ile Gly Ser Val Leu Phe Ala Val Tyr Leu His Arg
            35                  40                  45
Arg Leu Asp Lys Val Glu Glu Val Asn Leu His Glu Asp Phe Val
50                  55                  60
Phe Ile Lys Lys Leu Lys Arg Cys Asn Lys Gly Glu Gly Ser Leu Ser
65                  70                  75                  80
Leu Leu Asn Cys Glu Glu Met Arg Arg Gln Phe Glu Asp Leu Val Lys
                    85                  90                  95
Asp Ile Thr Leu Asn Lys Glu Glu Lys Lys Glu Asn Ser Phe Glu Met
                    100                 105                 110
Gln Arg Gly Asp Glu Asp Pro Gln Ile Ala Ala His Val Val Ser Glu
            115                 120                 125
Ala Asn Ser Asn Ala Ala Ser Val Leu Gln Trp Ala Lys Lys Gly Tyr
        130                 135                 140
Tyr Thr Met Lys Ser Asn Leu Val Thr Leu Glu Asn Gly Lys Gln Leu
145                 150                 155                 160
Thr Val Lys Arg Gln Gly Leu Tyr Tyr Ile Tyr Ala Gln Val Thr Phe
                    165                 170                 175
Cys Ser Asn Arg Glu Pro Ser Ser Gln Arg Pro Phe Ile Val Gly Leu
```

```
                    180                 185                 190
Trp Leu Lys Pro Ser Ser Gly Ser Glu Arg Ile Leu Leu Lys Ala Ala
            195                 200                 205

Asn Thr His Ser Ser Ala Lys Pro Cys Gly Gln Gln Ser Ile His Leu
            210                 215                 220

Gly Gly Val Phe Glu Leu Gln Pro Gly Ala Ser Val Phe Val Asn Val
225                 230                 235                 240

Thr Asp Pro Ser Gln Val Ser His Gly Thr Gly Phe Thr Ser Phe Gly
                245                 250                 255

Leu Leu Lys Leu
            260

<210> SEQ ID NO 24
<211> LENGTH: 252
<212> TYPE: PRT
<213> ORGANISM: Artificial sequence
<220> FEATURE:
<223> OTHER INFORMATION: Chimeric CD154 polypeptide encoded by the
      DNA sequence of SEQ ID NO:12

<400> SEQUENCE: 24

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Asp Glu Asp Pro Gln
            100                 105                 110

Ile Ala Ala His Val Val Ser Glu Ala Asn Ser Asn Ala Ala Ser Val
        115                 120                 125

Leu Gln Trp Ala Lys Lys Gly Tyr Tyr Thr Met Lys Ser Asn Leu Val
    130                 135                 140

Thr Leu Glu Asn Gly Lys Gln Leu Thr Val Lys Arg Gln Gly Leu Tyr
145                 150                 155                 160

Tyr Ile Tyr Ala Gln Val Thr Phe Cys Ser Asn Arg Glu Pro Ser Ser
                165                 170                 175

Gln Arg Pro Phe Ile Val Gly Leu Trp Leu Lys Pro Ser Ser Gly Ser
            180                 185                 190

Glu Arg Ile Leu Leu Lys Ala Ala Asn Thr His Ser Ser Ala Lys Pro
        195                 200                 205

Cys Gly Gln Gln Ser Ile His Leu Gly Gly Val Phe Glu Leu Gln Pro
    210                 215                 220

Gly Ala Ser Val Phe Val Asn Val Thr Asp Pro Ser Gln Val Ser His
225                 230                 235                 240

Gly Thr Gly Phe Thr Ser Phe Gly Leu Leu Lys Leu
                245                 250

<210> SEQ ID NO 25
<211> LENGTH: 1834
<212> TYPE: DNA
```

<213> ORGANISM: Homo sapiens

<400> SEQUENCE: 25

```
actttgacag tcttctcatg ctgcctctgc caccttctct gccagaagat accatttcaa      60
ctttaacaca gcatgatcga aacatacaac caaacttctc cccgatctgc ggccactgga     120
ctgcccatca gcatgaaaat ttttatgtat ttacttactg ttttcttat cacccagatg      180
attgggtcag cacttttgc tgtgtatctt catagaaggt tggacaagat agaagatgaa      240
aggaatcttc atgaagattt tgtattcatg aaaacgatac agagatgcaa cacaggagaa     300
agatccttat ccttactgaa ctgtgaggag attaaaagcc agtttgaagg ctttgtgaag     360
gatataatgt aaacaaaga ggagacgaag aaagaaaaca gctttgaaat gcaaaaaggt     420
gatcagaatc ctcaaattgc ggcacatgtc ataagtgagg ccagcagtaa aacaacatct     480
gtgttacagt gggctgaaaa aggatactac accatgagca caacttggt aaccctggaa      540
aatgggaaac agctgaccgt taaaagacaa ggactctatt atatctatgc ccaagtcacc     600
ttctgttcca atcgggaagc ttcgagtcaa gctccattta tagccagcct ctgcctaaag     660
tccccggta gattcgagag aatcttactc agagctgcaa atacccacag ttccgccaaa      720
ccttgcgggc aacaatccat tcacttggga ggagtatttg aattgcaacc aggtgcttcg     780
gtgtttgtca atgtgactga tccaagccaa gtgagccatg gcactggctt cacgtccttt     840
ggcttactca aactctgaac agtgtcacct tgcaggctgt ggtggagctg acgctgggag     900
tcttcataat acagcacagc ggttaagccc acccctgtt aactgcctat ttataacct      960
aggatcctcc ttatggagaa ctatttatta tacactccaa ggcatgtaga actgtaataa    1020
gtgaattaca ggtcacatga aaccaaaacg ggccctgctc cataagagct tatatatctg    1080
aagcagcaac cccactgatg cagacatcca gagagtccta tgaaaagaca aggccattat    1140
gcacaggttg aattctgagt aaacagcaga taacttgcca agttcagttt tgtttctttg    1200
cgtgcagtgt ctttccatgg ataatgcatt tgatttatca gtgaagatgc agaagggaaa    1260
tggggagcct cagctcacat tcagttatgg ttgactctgg gttcctatgg ccttgttgga    1320
gggggccagg ctctagaacg tctaacacag tggagaaccg aaaccccccc ccccccccg     1380
ccaccctctc ggacagttat tcattctctt tcaatctctc tctctccatc tctctctttc    1440
agtctctctc tctcaaccte ttcttccaa tctctctttc tcaatctctc tgtttccctt     1500
tgtcagtctc ttccctcccc cagtctctct tctcaatccc cctttctaac acacacacac    1560
acacacacac acacacacac acacacacac acacacacac agagtcaggc cgttgctagt    1620
cagttctctt ctttccaccc tgtccctatc tctaccacta tagatgaggg tgaggagtag    1680
ggagtgcagc cctgagcctg cccactcctc attacgaaat gactgtattt aaaggaaatc    1740
tattgtatct acctgcagtc tccattgttt ccagagtgaa cttgtaatta tcttgttatt    1800
tatttttga ataataaaga cctcttaaca ttaa                                 1834
```

<210> SEQ ID NO 26
<211> LENGTH: 261
<212> TYPE: PRT
<213> ORGANISM: Homo sapiens

<400> SEQUENCE: 26

```
Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30
```

| Ile | Thr | Gln | Met | Ile | Gly | Ser | Ala | Leu | Phe | Ala | Val | Tyr | Leu | His | Arg |
| | | | 35 | | | | 40 | | | | 45 | | | | |

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 27
<211> LENGTH: 783
<212> TYPE: DNA
<213> ORGANISM: Mus musculus

<400> SEQUENCE: 27

| atgatagaaa | catacagcca | accttccccc | agatccgtgg | caactggact | tccagcgagc | 60 |
| atgaagattt | ttatgtattt | acttactgtt | ttccttatca | cccaaatgat | tggatctgtg | 120 |
| ctttttgctg | tgtatcttca | tagaagattg | gataaggtcg | aagaggaagt | aaaccttcat | 180 |
| gaagattttg | tattcataaa | aaagctaaag | agatgcaaca | aaggagaagg | atctttatcc | 240 |
| ttgctgaact | gtgaggagat | gagaaggcaa | tttgaagacc | ttgtcaagga | tataacgtta | 300 |
| aacaaagaag | agaaaaaaga | aaacagcttt | gaaatgcaaa | gaggtgatga | ggatcctcaa | 360 |
| attgcagcac | acgttgtaag | cgaagccaac | agtaatgcag | catccgttct | acagtgggcc | 420 |
| aagaaaggat | attataccat | gaaaagcaac | ttggtaatgc | ttgaaaatgg | gaaacagctg | 480 |
| acggttaaaa | gagaaggact | ctattatgtc | tacactcaag | tcaccttctg | ctctaatcgg | 540 |
| gagccttcga | gtcaacgccc | attcatcgtc | ggcctctggc | tgaagcccag | cagtggatct | 600 |
| gagagaatct | tactcaaggc | ggcaaatacc | cacagttcct | cccagctttg | cgagcagcag | 660 |
| tctgttcact | gggcggagt | gtttgaatta | caagctggtg | cttctgtgtt | tgtcaacgtg | 720 |
| actgaagcaa | gccaagtgat | ccacagagtt | ggcttctcat | cttttggctt | actcaaactc | 780 |
| tga | | | | | | 783 |

```
<210> SEQ ID NO 28
<211> LENGTH: 260
<212> TYPE: PRT
<213> ORGANISM: Mus musculus

<400> SEQUENCE: 28

Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg
        35                  40                  45

Arg Leu Asp Lys Val Glu Glu Val Asn Leu His Glu Asp Phe Val
    50                  55                  60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
                100                 105                 110

Gln Arg Gly Asp Glu Asp Pro Gln Ile Ala Ala His Val Val Ser Glu
            115                 120                 125

Ala Asn Ser Asn Ala Ala Ser Val Leu Gln Trp Ala Lys Lys Gly Tyr
130                 135                 140

Tyr Thr Met Lys Ser Asn Leu Val Met Leu Glu Asn Gly Lys Gln Leu
145                 150                 155                 160

Thr Val Lys Arg Glu Gly Leu Tyr Tyr Val Tyr Thr Gln Val Thr Phe
                165                 170                 175

Cys Ser Asn Arg Glu Pro Ser Ser Gln Arg Pro Phe Ile Val Gly Leu
            180                 185                 190

Trp Leu Lys Pro Ser Ser Gly Ser Glu Arg Ile Leu Leu Lys Ala Ala
        195                 200                 205

Asn Thr His Ser Ser Ser Gln Leu Cys Glu Gln Gln Ser Val His Leu
    210                 215                 220

Gly Gly Val Phe Glu Leu Gln Ala Gly Ala Ser Val Phe Val Asn Val
225                 230                 235                 240

Thr Glu Ala Ser Gln Val Ile His Arg Val Gly Phe Ser Ser Phe Gly
                245                 250                 255

Leu Leu Lys Leu
            260
```